United States Patent [19]
Ohno

[11] Patent Number: 5,558,865
[45] Date of Patent: Sep. 24, 1996

[54] HIV IMMUNOTHERAPEUTICS

[75] Inventor: Tsuneya Ohno, Boston, Mass.

[73] Assignee: Nissin Shokuhin Kabushiki Kaisha, Osaka, Japan

[21] Appl. No.: 111,080

[22] Filed: Aug. 24, 1993

Related U.S. Application Data

[63] Continuation-in-part of Ser. No. 39,457, filed as PCT/US92/07111, Aug. 24, 1992, abandoned, which is a continuation-in-part of Ser. No. 748,562, Aug. 22, 1991, abandoned.

[51] Int. Cl.$^6$ .............. C12N 5/12; A61K 39/42; C07K 16/12
[52] U.S. Cl. .............. 424/148.1; 435/240.27; 424/141.1; 424/130.1; 424/139.1; 530/388.35; 530/387.9; 530/388.1; 530/387.1
[58] Field of Search .............. 424/148.1, 141.1, 424/130.1, 139.1; 435/240.27; 530/388.35, 387.9, 388.1, 387.1

[56] References Cited

U.S. PATENT DOCUMENTS 5,019,387   5/1991   Haynes et al. .............. 424/188.1

FOREIGN PATENT DOCUMENTS

| 295803A1 | 12/1988 | European Pat. Off. |
| 032700A2 | 8/1989 | European Pat. Off. |
| 339504A2 | 11/1989 | European Pat. Off. |
| 465979A1 | 1/1992 | European Pat. Off. |
| WO88/09181 | 12/1988 | WIPO |
| WO89/04370 | 5/1989 | WIPO |
| WO90/03984 | 4/1990 | WIPO |
| WO90/12868 | 11/1990 | WIPO |
| WO91/06575 | 11/1990 | WIPO |
| WO90/15078 | 12/1990 | WIPO |
| WO91/07493 | 5/1991 | WIPO |
| WO91/07494 | 5/1991 | WIPO |
| WO91/09625 | 7/1991 | WIPO |
| WO91/11198 | 8/1991 | WIPO |
| WO91/13148 | 9/1991 | WIPO |
| WO91/17764 | 11/1991 | WIPO |
| WO91/19797 | 12/1991 | WIPO |

OTHER PUBLICATIONS

Akerblom et al., "Neutralizing cross–reactive and non–neutralizing monoclonal antibodies to HIV–1 gp 120", *AIDS*, 4: 953–960 (1990).
Banapour et al., "The AIDS–Associated Retrovirus is Not Sensitive to Lysis or Inactivation by Human Serum", *Virology*, 152: 268–271 (1986).
Bartholomew et al., "Lysis of Oncornaviruses by Human Serum", *J. Exp. Med.*, 147: 844–853 (1978).
Broliden et al., "Identification of Amino Acids in the V3 Region of gp120 for Virus Neutralization by HIV–1 Specific Antibodies," *Immunology*, 73: 371–376 (1991).
Cheng–Mayer et al., "Human Immunodeficiency Virus Can Productively Infect Cultured Human Glial Cells", *Proc. Natl. Acad. Sci., USA*, 84: 3526–3530 (1987).

(List continued on next page.)

Primary Examiner—Lila Feisee
Attorney, Agent, or Firm—Marshall, O'Toole, Gerstein, Murray & Borun

[57] ABSTRACT

The present invention provides monoclonal antibodies that are specifically immunoreactive with an HIV-1 gp120 protein or its precursor gp160 protein comprising the amino acid sequence set out in SEQ ID NO: 1, G-P-G-R, and characterized by their ability to neutralize, in vitro, the infection of H9 cells by live HIV-1 strains MN and III$_B$ as determined by reverse transcriptase, p24, MT-2 and syncytium formation assays. Presently preferred antibody NM-01 isolated from mouse/mouse hybridoma ATCC HB 10726 is further characterized by its capacity to mediate complement-dependent virolysis of HIV-1 particles and antibody-dependent cellular cytotoxicity of HIV-1 infected cells. Antibodies consisting essentially of a human antibody variable region comprising a sequence of amino acids of at least one complementarity determining region of the monoclonal antibody produced by the hybridoma cell line ATCC HB 10726 are specifically disclosed. Pharmaceutical compositions of the invention are projected to be useful in the passive immunization treatment of animals, especially humans, susceptible to or infected with HIV-1.

8 Claims, 28 Drawing Sheets

OTHER PUBLICATIONS

Chothia et al., "Canonical Structures for the Hypervariable Regions of Immunoglobulins", *J. Mol. Biol.*, 196: 901–917 (1987).

Cooper et al., "Lysis of RNA Tumor Viruses by Human Serum: Direct Antibody–Independent Triggering of the Classical Complement Pathway", *J. Exp. Med.*, 144: 970–984 (1976).

Durda et al., "HIV–1 Neutralizing Monoclonal Antibodies Induced by a Synthetic Peptide", *AIDS Res. Human Restrov.*, 6: 1115–1123 (1990).

Emini et al., "Prevention of HIV–1 Infection in Chimpanzees by gp120 V3 Domain–Specific Monoclonal Antibody", *Nature*, 355: 728–730 (1992).

Epp et al., "Crystal and Molecular Structure of a Dimer Composed of the Variable Portions of the Bence–Jones Protein REI", *Eur J. Biochem*, 45: 513–524 (1974).

Foote et al., "Antibody Framework Residues Affecting the Conformation of the Hypervariable Loops", *J. Mol. Biol.*, 224: 487–499 (1992).

Fung et al., "Monoclonal Antibodies that Neutralize HIV–1 Virions and Inhibit Syncytium Formation by Infected Cells", *Bio/Technology*, 5:940–946 (1987).

Goding, "Antibody Production by Hybridomas", *J. Immunol. Meth.* 39: 285–308 (1980).

Gorny et al., "Production of Site–Selected Neutralizing Human Monoclonal Antibodies Against the Third Variable Domain of the Human Immunodeficiency Virus Type 1 Envelope glycoprotein", *Proc. Natl. Acad. Sci.*, USA, 88: 3238–3242 (1991).

Gorny et al., "Neutralization of Diverse Human Immunodeficieny Virus Type 1 Variants by an Anti–V3 Human Monoclonal Antibody," *J. Virol.*, 66(12): 7538–7542 (Dec. 1992).

Goudsmit et al., "Human Immunodeficiency Virus Type 1 Neutralization Epitome With Conserved Architecture Elicits Early Type–Specific Antibodies in Experimentally Infected Chimpanzees", *Proc. Natl. Acad. Sci.*, USA, 85: 4478–4482 (1988).

Haigwood et al., "Evidence for Neutralizing Antibodies Directed Against Conformational Epitopes of HIV–1 gp120", *Vaccines*, 90: 313–320 (1990).

Halstead et al., "Antibody–Enhanced Dengue Virus Infection in Primate Leukocytes", *Nature* 265: 739–741 (1977).

Ho et al., "Conformational Epitope on gp120 Important in CD4 Binding and Human Immunodeficiency Virus Type 1 Neutralization Identified by a Human Monoclonal Antibody", *J. Virol.* 65(1): 489–493 (1991).

Ho et al., "Second Conserved Domain of gp120 Is Important for HIV Infectivity and Antibody Neutralization", *Science*, 239: 1021–1023 (1988).

Holley et al., "Prediction of Optimal Peptide Mixtures to Induce Broadly Neutralizing Antibodies to Human Immunodeficiency Virus Type 1", *Proc. Natl. Acad. Sci.*, USA, 88: 6800–6804 (1991).

Jackson et al., "Passive Immunoneutralisation of Human Immunodeficiency Virus in Patients with Advanced AIDS", *The Lancet*: 647–652 (1988).

Javaherian et al., "Principal Neutralizing Domain of the Human Immunodeficiency Virus Type 1 Envelope Protein", *Proc. Natl. Acad. Sci.*, USA, 86: 6768–6772 (1989).

Javaherian et al., "Broadly Neutralizing Antibodies Elicited by the Hypervariable Neutralizing Determinant of HIV–1", *Science*, 250: 1590–1593 (1990).

Johnson et al., "HIV–Infected Cell Fusion Assay" Techniques in HIV–1 Research, Techniques in HIV–1 Research, Stockton Press, New York pp. 92–97 (1990).

Kabat et al., "Sequences of Proteins of Immunological Interest," 5th Edition, U.S. Department of Health and Human Services, U.S. Government Printing Office (1991).

Karpas et al., "Effects of Passive Immunization in Patients with the Acquired Immunodeficiency Syndrome–Related Complex and Acquired Immunodeficiency Syndrome", *Proc. Natl. Acad. Sci.*, USA, 85: 9234–9237 (1988).

LaRosa et al., "Conserved Sequence and Structural Elements in the HIV–1 Principal Neutralizing Determinant", *Science*, 249: 932–935 (1990).

Lasky et al., "Neutralization of the AIDS Retrovirus by Antibodies to a Recombinant Envelope Glycoprotein", *Science*, 233: 209–212 (1986).

Liou et al., "A Chimeric Mouse–Human Antibody that Retains Specificity for HIV gp120 and Mediates the Lysis of HIV–Infected Cells", *J. of Immun.*, 143(12): 3967–3975 (1989).

Matsushita et al., "Characterization of a Human Immunodeficiency Virus Neutralizing Monoclonal Antibody and Mapping of the Neutralizing Epitope", *J. Virol.*, 62: 2107–2114 (1988).

McCune, "HIV–1: The Infective Process in Vivo", *Cell*, 64: 351–363 (1991).

Mosmann, "Rapid Colorimetric Assay for Cellular Growth and Survival: Application to Proliferation and Cytotoxicity Assays", *J. Immunol Meth.*, 65: 55–63 (1983).

Nakamura et al., "Complement–Dependent Virolysis of HIV–1 with Monoclonal Antibody NM–01" *AIDS Research and Human Retroviruses*, 9(7):619–626 (1993).

Ohno et al., "A broadly neutralizing monoclonal antibody that recognizes the $V_3$ region of human immunodeficiency virus type 1 glycoprotein gp120", *Proc. Natl. Acad. Sci.* USA, 88:10726–10729 (Dec. 1991).

Oi et al., "Immunoglobulin–Producing Hybrid Cell Lines", *Selected Methods Cell Immunology*, pp. 351–372 (1979).

Orlandi et al., "Cloning Immunoglobulin Variable Domains for Expression by the Po;ymerase Chain Reaction", *Proc. Natl. Acad. Sci.*, USA, 86: 3833–3837 (1989).

Palker et al., "Type–specific Neutralization of the Human Immunodeficiency Virus with Antibodies to Env–encoded Synthetic Peptides", *Proc. Natl. Acad. Sci.*, USA, 85: 1932–1936 (1988).

Pauwels et al., "Rapid and Automated Tetrazolium–Based Colorimetric Assay for the Detection of Anti–HIV Compounds", *J. Virol Meth.*, 20: 309–321 (1988).

Peiris et al., "Monoclonal Anti–Fc Receptor IgG Blocks Antibody Enhancement of Viral Replication in Macrophages", *Nature*, 289: 189–191 (1981).

Pirofski et al., "Variable Region Gene Utilization and Mutation in a Group of Neutralizing Murine Anti–Human Immunodeficiency Virus Type I Principal Neutralizing Determinant Antibodies", *AIDS Research and Human Retroviruses*, 9(1):41–49 (1993).

Poiesz et al., "Detection and Isolation of Type C Retrovirus Particles from Fresh and Cultured Lymphocytes of a Patent with Cutaneous T–Cell Lymphoma", *Proc. Natl. Sci.*, USA, 77: 7415–7419 (1980).

Putney et al., "HTLV–III/LAV–Neutralizing Antibodies to an *E. Coli*–Produced Fragment of the Virus Envelope", *Science*,234: 1392–1395 (1986).

Richman, "Plaque Reduction and Cytotoxicity Assays of HIV Sensitivity to Antiviral Compounds", *AIDS Research and Reference Reagent Program*, Courier No. 90–01, pp. 6–9 (1990).

Riechmann et al., "Reshaping Human Antibodies for Therapy", *Nature*, 332: 323–327 (1988).

Rusche et al., "Antibodies That Inhibit Fusion of Human Immunodeficiency Virus–Infected Cells Bind a 24–Amino Acid Sequence of the Viral Envelope, gp120", *Proc. Natl. Acad. Sci.*, USA, 85: 3198–3202 (1988).

Saul et al., "Preliminary Refinement and Structural Analysis of the Fab Fragment from Human Immunoglobulin New at 2.0 A Resolution", *J. Biol. Chem.*, 253: 585–597 (1978).

Schlesinger et al., "Growth of 17D Yellow Fever Virus in a Macrophage–Like Cell Line U937: Role of Fc and Viral Receptors in Antibody–Mediated Infection", *J. Immunol.*, 127: 659–665 (1981).

Scott et al., "Human Monoclonal Antibody That Recognizes the V3 Region of Human Immunodeficiency Virus gp120 and Neutralizes the Human T–Lymphoctropic Virus Type III$_{MN}$ Strain", *Proc. Natl. Acad. Sci.*, USA, 87: 8597–8601 (1990).

Sherwin et al., "Complement–Mediated Lysis of Type–C Virus: Effect of Primate and Human Sera on Various Retroviruses", *Int. J. Cancer*, 21: 6–11 (1978).

Spear et al., "Neutralization of Human Immunodeficiency Virus Type 1 by Complement Occurs by Viral Lysis", *J. Virol.*, 64 (12): 5869–5873 (1990).

Takeda et al., "Antibody–Enhanced Infection by HIV–1 Via Fc Receptor–Mediated Entry", *Science*, 242: 580–583 (1988).

Tempest et al., "Reshaping a Human Monoclonal Antibody to Inhibit Human Respiratory Syncytial Virus Infection In Vivo", *Bio/Technology*, 9: 266–271 (1991).

Tramontano et al., "Framework Residue 71 is a Major Determinant of the Position and Conformation of the Second Hypervariable Region in the V$_H$ Domains of Immunoglobulins", *J. Mol. Biol.*, 215: 175–182 (1990).

Weiss et al., Eds. *Molecular Biology of Tumor Viruses, RNA Tumor Viruses*, Cold Spring Harbor Laboratory, New York, pp. 1216–1220 (1982).

Weiss et al., "Variable and Conserved Neutralization Antigens of Human Immunodeficiency Virus", *Nature*, 324: 572–575 (1986).

Welsh et al., "Inactivation and Lysis of Oncornaviruses by Human Serum", *Virology*, 74: 432–440 (1976).

Waldmann Science vol. 252 1657, (1991).

Hird et al. Genes and Cancer Carney and Sikora p. 183 ed (1990).

Harris et al. TibTech vol. 11 p. 42 (1993).

Morrison et al. Clin Chem. 34/9 1668–(1988).

Queen et al. PNAS vol. 86 p. 10029 (1989).

FIGURE 14

```
                10             20            30             40
                 —              —             —              —
(V-H)
NM-01    QIQLKESGPA    VIKPSQSLSL    TCIVSGFSIT    SSSYCWHWIR
BAT123   EVQLQESGPG    LVKPSQSLSL    TCTVTGYSIT    SD YAWNWIR
F58/H3   QIQLQQSGAE    LASPGASVTL    SCKASGYTFT    DHIMNWVKKR
P4/D10   QIQLQQSGAE    LASPGASVTL    SCKASGYTFT    DHIMNWVKKR 50             60            70             80
                 —              —             —              —
NM-01    QPPGKGLEWM    GRICYEGSID    YSPSIKSRST    ISRDTSLNRF
BAT123   QFPGNKLEWM    GYISYSGSTT    YNPSLKSRIS    ITRDTSKNLF
F58/H3   PGQGLEWIGR    IFPVSGETNY    NQKFMGKATF    SVDRSSSTVS
P4/D10   PGQGLEWIGR    IFPVSGETNY    NQKFMGKATF    SVDRSSSSTVS 90            100           110            120
                 —              —             —              —
NM-01    FIQLSSVTNE    DTAMYYCSRE    NHGTTTSMDY    WGQGTSVTVS
BAT123   FLQLSSVTSE    DTATYYCARG    SFGDWGQGTL    VTVSA
F58/H3   MVLNSLTSED    PAVYYCDLIY    YDYEEDYYFD    YWGQGTTLTV
P4/D10   MVLNSLTSED    PAVYYCDLIY    YDYEEDYYFD    YWGQGTTLTV
```

FIGURE 15

| (V-L) | 10 | 20 | 30 | 40 |
|---|---|---|---|---|
| NM-01 | DIVLTQSPAS | LAVSLGQRAT | ISQRASESVD | SYGNSFMHWY |
| BAT123 | DIVLTQSPAS | LAVSLGQRAT | ISCKASQSVD | YDGDSYMNWY |
| F58/H3 | DIVLTQSPAS | LAVSLGQRAT | ISCRASESVD | DYGISFMHWY |
| P4/D10 | DIVLTQSPAS | LAVSLGQRAT | ISCRASESVD | DYGISFMHWY |

| | 50 | 60 | 70 | 80 |
|---|---|---|---|---|
| NM-01 | QQKPGQSPKL | LIYVASNLES | GVPARFSGSG | SRTDFTLTID |
| BAT123 | QQKPGQPPKL | LIYAASNVES | GIPARFYGSG | SGTDFTNTIH |
| F58/H3 | QQKLGQPPKL | LIYRASNLES | GIPARFSGSG | SGTEFTLTIN |
| P4/D10 | QQKLGQPPKL | LIYRASNLES | GIPARFSGSG | SGTEFTLTIN |

| | 90 | 100 | 110 | 120 |
|---|---|---|---|---|
| NM-01 | PVEADDAATY | YCQQNNEDPL | TFGAGTKLEL | KRADAAPTVS |
| BAT123 | PVEEEDAATY | YCQQSIDDPS | TFGGGTKLEI | KRADAAPTVS |
| F58/H3 | PVETDDVATY | YCQQSNKDPL | TFGAGTKLEL | KRADAAPTVS |
| P4/D10 | PVETDDVATY | YCQQSNKDPL | TFGAGTKLEL | KRADAAPTVS |

FIGURE 16

|  | 10 | 20 | 30 | 40 |
|---|---|---|---|---|
| MuVH | QIQLKESGPA | VIKPSQSLSL | TCIVSGFSIT | SSSYCWHWIR |
| HuVH | QVQLQESGPG | LVRPSQTLSL | TCTVSGFSIT | SSSYCWHWVR |

|  | 50 | 60 | 70 | 80 |
|---|---|---|---|---|
| MuVH | QPPGKGLEWM | GRICYEGSID | YSPSIKSRST | ISRDTSLNRF |
| HuVH | QPPGRGLEWI | GRICYEGSID | YSPSIKSRVT | MLRDTSKNQF |

|  | 90 | 100 | 110 | 120 |
|---|---|---|---|---|
| MuVH | FIQLSSVTNE | DTAMYYCSRE | NHGTTTSMDY | WGQGTSVTVS |
| HuVH | SLRLSSVTAA | DTAVYYCARE | NHGTTTSMDY | WGQGSLVTVS |

FIGURE 17

```
            10          20          30          40
             -           -           -           -
MuVK   DIVLTQSPAS  LAVSLGQRAT  ISCRASESVD  SYGNSFMHWY
HuVK   DIQMTQSPSS  LSASVGDRVT  ITCRASESVD  SYGNSFMHWY
HuVKF  DIQMTQSPSS  LSASVGDRVT  ITCRASESVD  SYGNSFMHWY 50          60          70          80
             -           -           -           -
MuVK   QQKPGQPPKL  LIYVASNLES  GVPARFSGSG  SRTDFTLTID
HuVK   QQTPGKAPKL  LIYVASNLES  GVPSRFSGSG  SGTDYTFTIS
HuVKF  QQTPGKAPKL  LIYVASNLES  GVPSRFSGSG  SGTDFTFTIS 90         100         110
             -           -           -
MuVK   PVEADDAATY  YCQQNNEDPL  TFGAGTKLEL  K
HuVK   SLQPEDIATY  YCQQNNEDPL  TFGQGTKLQI  T
HuVKF  SLQPEDIATY  YCQQNNEDPL  TFGQGTKLQI  T
```

HIV IMMUNOTHERAPEUTICS

BACKGROUND

This application is a continuation-in-part of U.S. patent application Ser. No. 08/039,457, filed on Apr. 22, 1993 now abandoned, which corresponds to International Patent Application No. PCT/US92/07111 filed on Aug. 24, 1992 which is in turn a continuation-in-part of U.S. patent application Ser. No. 07/748,562 filed on Aug. 22, 1991, now abandoned.

The present invention relates, in general, to materials and methods useful in the prevention and treatment of Human Immunodeficiency Virus (HIV-1) infection. More particularly, the invention relates to monoclonal antibodies useful in passive immunization of HIV-1 susceptible or infected animals, especially humans.

The infective process of HIV-1 in vivo has recently been the subject of a review article by McCune, Cell, 64, pp. 351–363 (1991). Briefly, HIV-1 infects a variety of cell lineages, such as T-cells, monocytes/macrophages and neuronal cells, which express the CD4 receptor. Because the vast majority of $CD4^+$ cells in the body are "resting" or quiescent and divide only in response to specific signals, infection with HIV-1 results in $CD4^+$ cells harboring transcriptionally inactive virus. Stimulation of the immune system of infected animals, including active immunization, may result in polyclonal activation and the signaling of resting $CD^{4+}$ cells to go into the S phase of the cell cycle. The replicating cells then actively produce viral particles, provoking spread of the infection. Considering this negative effect of stimulating the immune system of an HIV-1-infected animal, it is possible that the most effective method of preventing or treating HIV-1 infection is passive immunization, that is, administering anti-HIV-1 antibodies to a susceptible or infected animal.

Jackson et al., Lancet, 2, pp. 647–652 (1988) reports that a single administration of anti-HIV-I antibodies in the form of plasma to human patients afflicted with advanced acquired immunodeficiency syndrome (AIDS, the syndrome of progressive immune system deterioration associated with HIV-I infection) temporarily resulted in: fewer symptoms, a transient increase in T lymphocytes, a reduction in the frequency of opportunistic infections and a decline in the rate at which HIV-1 could be cultured from plasma or lymphocytes of the patients. See also, Karpas et al., Proc, Natl, Acad. Sci. USA, 85, pp. 9234–9237 (1988). Moreover, Emini et al., Nature, 355, pp. 728–730 (1992) reports that the administration of an antibody specifically reactive with HIV-1 to a chimpanzee before the animal was exposed to HIV-1 resulted in the chimpanzee remaining free of signs of viral infection. These studies indicate that antibodies capable of neutralizing HIV-1 can be useful in the prevention/treatment of HIV-1 infection.

The HIV-1 major external envelope glycoprotein, gp120, binds to the cellular CD4 receptor and facilitates the internalization of the virus. Several epitopes of the glycoprotein have been associated with the development of neutralizing antibodies. Ho et al., Science, 239, pp. 1021–1023 (1988) reports that amino acids 254–274 of gp120 elicit polyclonal antisera capable of group-specific neutralization of three different isolates of HIV-1. Conformation-dependent epitopes, epitopes not consisting of primary sequences of amino acids, on gp 120 have also been implicated in eliciting antibodies that neutralize diverse strains of the virus by Haigwood et al., Vaccines 90, pp. 313–320 (1990) and Ho et al., J. Virol., 65(1), pp. 489–493 (1991). The so-called "principal neutralizing determinant" (PND) of HIV-1 gp120 has been localized to the "$V_3$ loop" of gp120. See Putney et al., Science, 234, pp. 1392–1395 (1986); Rusche et al., Proc. Natl. Acad. Sci. USA, 85, pp. 3198–3202 (1988); Goudsmit et al., Proc, Natl, Acad. Sci, USA, 85, pp. 4478–4482 (1988); Palker et al., Proc, Natl. Acad. Sci, USA, 85, pp. 1932–1936 (1988); and Holley et al., Proc. Natl, Acad. Sci. USA, 85, pp. 6800–6804 (1991). The V3 loop consists of a hypervariable domain which is established by disulfide bonding between cysteine residues flanking the domain. The V3 loop of HIV-1$_{MN}$, for example, is formed by a disulfide bond between the cysteine residues at positions 302 and 336 of gp120.

Recombinant and synthetic protein fragments including the series of amino acid residues of the V3 loop from various HIV isolates have been reported to elicit isolate- or type-specific neutralizing antibodies in rodents by Lasky et al., Science, 233, pp. 209–212 (1986); Palker et al., supra; Matsushita et al., J. Virol., 62, pp. 2107–2114 (1988); and Javaherian et al., Proc. Natl. Acad, Sci. USA, 86, pp. 6768–6772 (1989). More recent studies [Puthey et al., supra and LaRosa et al., Science, 249, pp. 932–935 (1990)] have demonstrated that the S-turn structure of the $V_3$ loop is the site recognized by the isolate-specific antibodies. Scott et al., Proc. Natl. Acad. Sci. USA, 87, pp. 8597–8601 (1990) report that the PND can also induce a type-specific antibody in humans. The hypervariability of the PND may account for the type-specific neutralizing activity generated by the epitope.

Several studies have suggested that antibodies prepared against recombinant gp120, purified gp120 or synthetic peptides from $V_3$ domain can neutralize diverse HIV-1 isolates. Javaherian et al., Science, 250, pp. 1590–1593 (1990) and Weiss et al., Nature, 324, pp. 572–575 (1986) each describe neutralization of both MN and III$_B$ isolates by polyclonal sera from rabbits respectively immunized with a peptide corresponding to the PND of MN isolates and with a recombinant gp120 derived from a III$_B$ isolate. See also, Haynes et al., U.S. Pat. No. 5,019,387.

Akerblom et al., AIDS, 4, pp. 953–960 (1990) describes monoclonal antibody preparations that neutralize III$_B$ and eleven primary HIV-1 isolates. See also, Patent Cooperation Treaty (PCT) Publication No. WO 91/11198 of Wahren et al., published on Aug. 8, 1991. The strain homology of the Akerblom primary isolates is not determined, however, and the eleven isolates may also be III$_B$. Durda et al., AIDS Res, Hum. Retrov., 6, pp. 1115–1123 (1990) report a monoclonal antibody that blocks syncytia formation by both MN- and III$_B$-infected cells, but does not neutralize MN infectivity as determined by a "LAV capture immunoassay," an assay which is purported to give results that would correlate with reverse transcriptase activity. Patent Cooperation Treaty Patent Publication No. WO 90/15078 of Scott et al., published on Dec. 13, 1990, describes monoclonal antibodies which inhibit syncytium formation by cells infected with vaccinia virus expressing the PND of MN or "MN-like" isolates. None of the assertedly "broadly neutralizing" antibodies are demonstrated, by means of standard reverse transcriptase, p24 or MT-2 assays, to neutralize multiple strains of live HIV-1. See also, PCT Publication Nos. WO 88/09181, WO 90/12868, WO 91/09625 of Tanox Biosystems, Inc., published on Dec. 1, 1988, Nov. 1, 1990 and Jul. 11, 1991, respectively; PCT Publication No. WO 91/19797 of New York University, published on Dec. 26, 1991; and Liou et al., J. Immunol., 143(12), pp. 3967–3975 (1989).

The foregoing publications indicate that monoclonal antibodies reactive with the HIV-1 PND developed to date exhibit different levels of group reactivity, but may not have broad neutralizing activity. The different patterns of type- and group-specific reactivity indicated by these studies may be related to both the amino acid sequence and the conformation of the loop region of gp120.

Several studies have suggested that the CD4 receptor may not represent the only cellular receptor responsible for viral infectivity. The results of these studies raise the possibility that administering the heretofore described antibodies which block infection of $CD4^+$ cells to a patient may afford only limited protection against HIV-1 infection. Cheng-Mayer et al., *Proc. Natl, Acad, Sci. USA*, 84, pp. 3526–3530 (1987) report HIV-1 infection of glial cells involving a receptor other than the CD4 molecule. Moreover, Takeda et al., *Science*, 242, pp. 580–583 (1988), indicate that antibody/HIV-1 complexes can infect monocytes by receptor-mediated endocytosis and enhance virus replication. Similar antibody-dependent enhancement of infection has been described in Halsted et al., *Nature.*, 265, pp. 739–741 (1977); Peiris et al., *Nature*, 289, pp. 189–191 (1981); and Schlesinger et al., J. Immunol., 127, pp. 659–665 (1981).

Previous work has shown that certain animal viruses are inactivated by complement, particularly C1q, through an antibody-independent mechanism. See Weiss, in *Molecular Biology of Tumor Viruses, RNA Tumor Viruses*, Weiss et al., Eds., Cold Spring Harbor Laboratory, New York, pp. 1219–1220 (1982); Welsh et al., *Virology*, 74, pp. 432–440 (1976); Bartholomew et al., *J. Exp. Med.*, 147, pp. 844–853 (1978); Cooper et al., *J. Exp. Med.*, 144, pp. 970–984 (1976); and Sherwin et al., *Int. J. Cancer*, 21, pp. 6–11 (1978). While Banapour et al., *Virology*, 152, pp. 268–271 (1986) describe unheated serum preparations as having no effect on the density of HIV-1 or its ability to infect peripheral blood mononuclear cells, Spear et al., *J. Virol.*, 64(12), pp. 5869–5873 (1990) report that HIV-1 treated with a combination of complement and pooled sera from HIV-1 sero-positive patients exhibits reduced infectivity.

There thus continues to exist a need in the art for new monoclonal antibody substances (including, e.g., murine-derived antibodies, humanized antibodies, and immunologically active antibody fragments) which are specifically immunoreactive with HIV-1. Ideally, such antibodies would be characterized by the ability to effect neutralization of multiple HIV-1 strains (e.g., $III_B$ and MN) as determined by standard reverse transcriptase, p24, MT-2 and syncytium formation assays involving suitable cultured host cells (e.g., H9 cells). In view of projected use in passive immunization of infected and non-infected patients, such monoclonal antibodies would optimally be capable of participating in (i.e., mediating) complement-dependent virolysis of HIV-1 particles and antibody-dependent cytolysis of HIV-1 infected cells.

BRIEF SUMMARY

The present invention provides toonotional antibodies which are specifically reactive with that portion of HIV-1 gp120 or gp160 protein comprising the amino acid sequence glycine-proline-glycine-arginine (G-P-G-R) set out in SEQ ID NO: 1, and are characterized by their capacity to neutralize the infection of H9 cells in culture by live HIV-1 strains MN and $III_B$ as determined by reverse transcriptase, p24, MT-2 and syncytium formation assays. The products of the invention may be further characterized by their capacity to mediate complement-dependent virolysis of HIV-1 particles and/or antibody-dependent cellular cytotoxicity of HIV-1 infected cells.

Monoclonal antibodies of the present invention may be used in diagnostic methods and/or kits to determine the presence of HIV-1 in a fluid (e.g., blood). Monoclonal antibodies according to the present invention, preferably IgG antibodies, are also particularly suitable for use in anti-HIV-1 treatment of animals, especially humans, susceptible to or infected with HIV-1. Immunologically effective amounts of the monoclonal antibodies are administered to a patient infected with HIV-1 or at risk of infection with the virus to develop passive immunity to HIV-1 infection, and preferably, to effect complement-dependent virolysis of HIV-1 particles and/or antibody-dependent cellular cytotoxicity of HIV-1 infected cells in the patient.

Chimeric or "humanized" antibodies (including CDR-grafted antibodies), antibody fragments, and especially bi-specific antibodies based on the claimed monoclonal antibodies are within the contemplation of the present invention, as are recombinant antibody-related products produced in procaryotic or eucaryotic cells. For example, antibody fragments, such as Fab and F(ab')$_2$ fragments, can be produced in culture by host cells such as *E. coli*, yeast, insect and mammalian cells upon determination of structural (sequence) information for the variable regions of the antibodies of the invention. Sequence information for the variable regions also enables preparation of CDR-grafted antibodies. Moreover, chimeric antibodies (e.g., mouse/human antibodies) may be prepared using transformed mouse myeloma cells or hybridoma cells and hi-specific antibodies may be produced by hybrid hybridoma cells. Specifically contemplated are antibodies which consist essentially of a human antibody variable region comprising a sequence of amino acids of at least one complementarity determining region of an antibody characterized by the ability to specifically bind to a sequence of amino acids of HIV-1 gp 120 or gp 160 consisting essentially of the sequence set out in SEQ ID NO: 1 and the ability to neutralize, in vitro, the infection of H9 cells by live HIV-1 strains MN and $III_B$ in reverse transcriptase, p24, MT-2 and syncytium formation assays. DNA sequences encoding such antibodies, host cells producing such antibodies and recombinant methods for producing such antibodies are contemplated.

Also within the contemplation of the present invention is the use, in anti-HIV-1 treatment, of a combination of the products of the present invention and other immunological agents and/or chemical therapeutic agents. Potential agents for combined administration include complement, antibodies which bind to various neutralizing and non-neutralizing domains of HIV-1 proteins, and chemical agents such as AZT.

As set forth in the following detailed description, monoclonal antibodies of the present invention were generated by immunization of an appropriate host with live HIV-1, thus presenting gp120 in its native conformation.

Specifically illustrating the present invention are the murine monoclonal antibody (designated NM-01) produced by hybridoma cell line HB 10726 which was received for deposit with the American Type Culture Collection, 12301 Parklawn Drive, Rockville, Md. 20852, on Apr. 9, 1991 and was assigned ATCC Accession No. HB 10726, and the humanized versions of antibody NM-01 designated NM-01 HuVH/HuVK, NM-01 HuVH/HuVKF, NM-01 HuVHM/HuVK, NM-01 HuVHS/HuVK, NM-01 HuVHS/HuVKF and NM-01 HuVHM/HuVKF produced by the cell lines which were deposited with the European Collection of Animal Cell Cultures (ECACC) on Aug. 20, 1993, PHLS Centre for Applied Microbiology & Research, Porten Down, Salisbury, Great Britain SP40JG and were assigned ECACC Accession Nos. 93082022, 93082019, 93082020, 93082023, 93082018 and 93082021, respectively.

Numerous aspects and advantages of the present invention will be apparent upon consideration of the illustrative examples and descriptions of practice of the present invention in the following detailed description thereof, reference being made to the drawing wherein:

BRIEF DESCRIPTION OF THE DRAWINGS

FIGS. 14 and 15 are alignments of the amino acid sequences of the variable regions of the light and heavy chains, respectively, of a monoclonal antibody of the present invention, NM-01, with the amino acid sequences of the light and heavy chains of three different anti-HIV-1 monoclonal antibodies.

FIGS. 16 and 17 are alignments of the amino acid sequences of the variable regions of the light and heavy chains, respectively, of murine monoclonal antibody NM-01 with the amino acid sequences of the light and heavy chains of a humanized NM-01 antibody of the invention designated HuVH/HuVKF.

EXAMPLES

Figure 1:
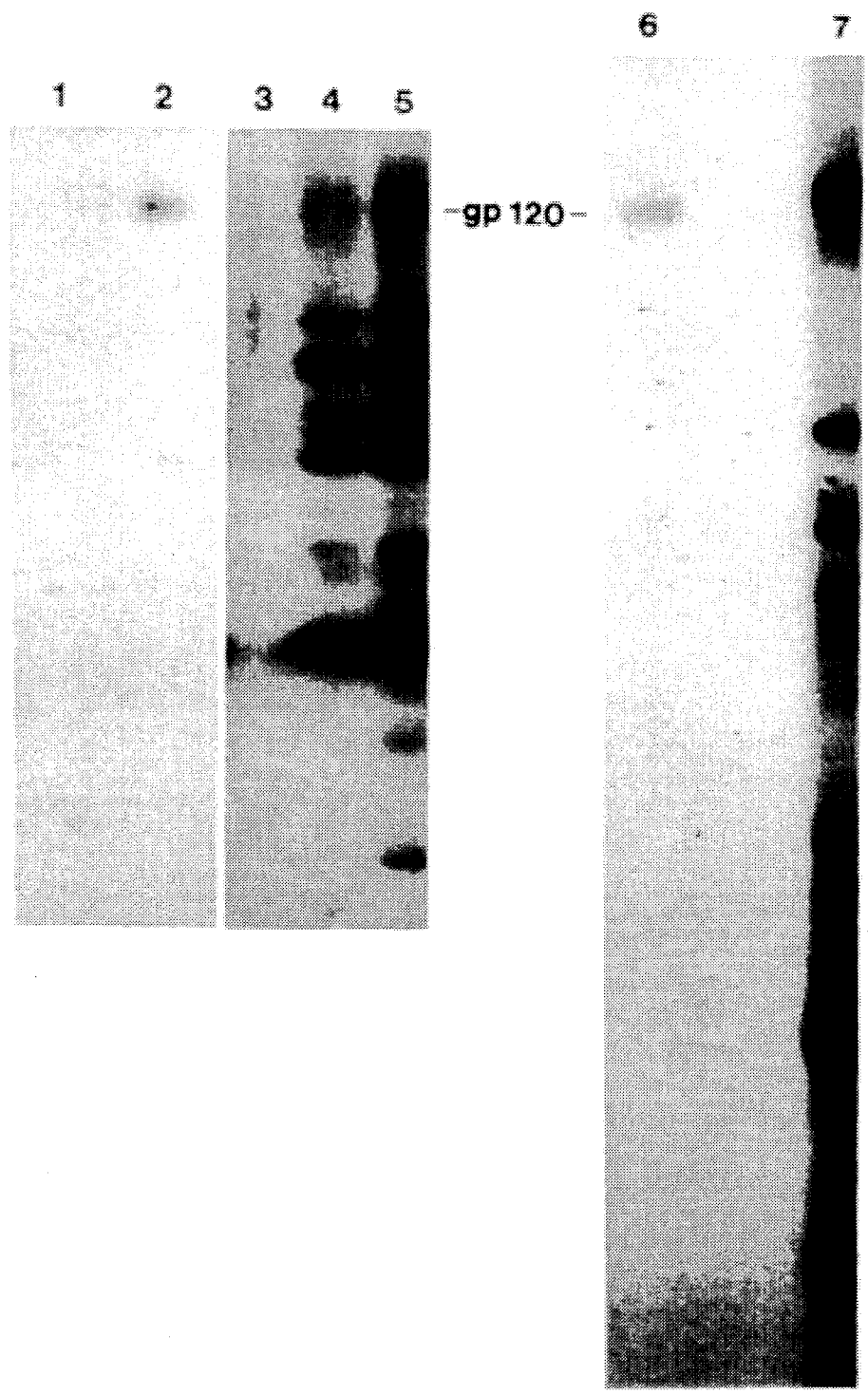
FIG. 1 is an composite autoradiogram of noninfected H9 cell, HIV-1$_{MN}$ and HIV-1$_{MB}$ proteins immunoblotted with a monoclonal antibody of the invention and immune sera from an sero-positive AIDS patient.

The following examples illustrate practice of the invention in the production of a hybridoma cell line HB 10726, the isolation therefrom of monoclonal antibodies immuno-reactive with HIV-1 gp120 (or its precursor gp160) proteins as well as peptides comprising the amino acid sequence G-P-G-R set out in SEQ ID NO: 1, the characterization of such monoclonal antibodies.

More particularly, Example 1 is directed to the production of hybridoma cell line HB 10726 and the isolation of monoclonal antibody NM-01 therefrom. Example 2 relates to the mapping of the viral epitope recognized by antibody NM-01. Example 3 describes the characterization of the reactivity of the monoclonal antibody with diverse HIV-1 isolates. Example 4 relates to the screening of antibody NM-01 for the capacity to neutralize infection of H9 cells by various live HIV-1 strains as demonstrated by reverse transcriptase and p24 assays. Example 5 is directed to the further screening of the antibody for the capacity to neutralize infectivity of live HIV-1 isolates as demonstrated by MT-2 and syncytium formation assays. Example 6 relates to peptide blockage of HIV-1 infectivity neutralization properties of monoclonal antibody NM-01. Example 7 describes analysis of the capacity of monoclonal antibody NM-01 to mediate complement-dependent lysis of HIV-1. Example 8 relates to the determination of the effect of the combination of monoclonal antibody NM-01 and complement on HIV-1 infectivity of susceptible cells in culture. Example 9 describes the DNA and deduced amino acid sequences of the heavy and light chain variable regions of monoclonal antibody NM-01 . Example 10 relates to the preparation of chimeric and humanized versions of monoclonal antibody NM-01 and assays for the immunological and biological activity thereof.

Example 1

Hybridoma cell line HB 10726 was produced using standard immunological techniques such as described in Oi and Herzenberg, *Selected Methods Cell Immunology*, pp. 351–372 (1979) and Godcling, *J. Immunol. Meth.*, 39, pp. 285–308 (1980) and set out specifically below.

A. Purification of Live HIV-1$_{MN}$

Three hundred ml of HIV-1$_{MN}$-infected H9 cell culture was collected and centrifuged at 1500 rpm for 5 minutes at 4° C. to pellet the cells. The virus-containing supernatant was removed and saved, while the precipitate was recentrifuged at 2100 rpm for 20 minutes. The second supernatant was collected and pooled with the first, and the supernatant was ultracentrifuged in a SW 27 rotor at 25,000 rpm for 90 minutes at 4° C. to pellet the viral particles. The resulting supernatant was discarded. The viral pellet was resuspended in approximately 10 ml TNE buffer (100 mM NaCl, 10 mM Tris-Hcl, pH 7.7, 1 mM EDTA). An ultracentrifuge tube was prepared containing a bottom layer of 10 ml 50% sucrose TNE, a middle layer of 10 ml 25% sucrose TNE and a top layer of 10 ml virus sample, and was ultracentrifuged at 25,000 rpm at 4° C. for 90 minutes. The virus precipitated as a white band between the layers of sucrose TNE and was collected with a pasteur pipet. Twenty ml TNE/15 mM EDTA (100 mM NaCl, 10 mM Tris-HCl, pH 7.7, 15 mM EDTA) was added to the virus and the viral sample was spun again at 25,000 rpm at 4° C. for 90 minutes. The resulting pellet comprised purified live HIV-1$_{MN}$.

Immunization and Hybridoma Preparation

One hundred μg live HIV-1$_{MN}$ was used to immunize each of three two-month old Balb/c mice by intraperitoneal injection. The mice were each boosted 3 weeks later with 30 μg virus and again after another 3 weeks with 100 μg of the viral preparation. The mice were sacrificed 3 days after the second boost and hybridoma cell lines were prepared by fusing splenocytes with P3-X63-Ag8-U1 cells (ATCC CRL 1597). Hybridoma cells lines were also prepared from the spleens of mice immunized with chronically infected H9 cells (10 mice), acutely infected H9 cells (9 mice) and infected H9 cell membranes (3 mice). Chronically infected H9 cells are cells 2 to 3 weeks after infection having reverse transcriptase assay (RT) counts of 100,000 cpm to 150,000 cpm, while acutely infected H9 cells are cells 10 to 12 days after infection having RT counts of 200,000 cpm to 250,000 cpm.

The hybridoma cell lines were prepared by the following method. A mixture of spleen cells from immunized mice was spun at 800 g for 5 minutes. The supernatant was aspirated from the cell pellet and 1 ml warm (37° C.) 50% PEG-1500 per $10^8$ cells was added to the pellet over a period of 1 minute (add 0.25 ml, stir gently with the piper tip for 15 seconds and repeat). The mixture was stirred for an additional minute with the same piper tip without breaking up cell clumps. One ml of "incomplete media" [RPMI 1640 (JRH Biosciences) supplemented with 25 mM HEPES (Sigma Co.), 10,000 U/ml penicillan and 10,000 mg/ml streptomycin] was then added over a period of 1 minute in the same manner (0.25 ml every 15 seconds) and another 1 ml was added over another minute. Next, 7 ml incomplete media was stirred in over a period of 2–3 minutes (1 ml every 20 seconds) resulting in a suspension of fine cell clumps. The final suspension was centrifuged at 500 g on a clinical centrifuge for 5 minutes and the supernatant was removed. The precipitate was resuspended by swirling (not vortexing or piperring solution up and down) in "complete media" ["incomplete media" as above supplemented with 15% fetal calf serum (FBS)] to a concentration of $2 \times 10^6$ cells per ml media. Next, 0.1 ml of this suspension ($2 \times 10^5$ total cells) was plated per well of 96-well plates. The plates were incubated at 37° C., 7% $CO_2$. The day of fusion was considered Day 0.

C. HAT Selection and Initial Screening of Hybridomas

Twenty-four hours after fusion (Day 1), 0.1 ml HAT media ($10^{-4}$M hypoxanthine, $5 \times 10^{-7}$M aminopterin and $1.6 \times 10^4$M thymidine) was added to each well. On Days 2, 3, 5, 8, 11, 14, 17 and 21, 0.1 ml of media was removed from each well and replaced with fresh 0.1 ml HAT media. On Days 2 through 5, the wells appeared to contain only dead cells. Hybridomas began to appear between Days 5 and 10. The hybridomas were easily visible as colonies of very refractible cells surrounded by cellular debris.

D. Hybridoma Screening

Several assays were utilized for screening the hybridoma supernatants. Hybridomas secreting antibodies reactive with HIV-1 were initially identified by screening membranes prepared from non-infected and MN-infected H9 cells by ELISA with hybridoma culture supernatants. This initial screen was followed by immunofluorescence and radioimmunoassay screening to supplement the ELISA data with antibody binding data to live infected cells.

Cell membranes for the ELISA were prepared from infected or noninfected H9 cells. The cells were suspended in a 250 mM sucrose/10 mM Tris-HCl buffer at pH 7.4 containing 1 mM EDTA. The suspension was homogenized in a Dounce homogenizer placed in an ice bath until no viable cells were seen by Trypan Blue exclusion. The mixture was centrifuged for 2 minutes at 50 g. The resulting pellet was rehomogenized and recentrifuged. The two supernatants were combined and centrifuged at 20,000 g for 20 minutes. The pellet was again homogenized in the same buffer and centrifuged for 20 minutes and the pellet resuspended in 7 ml of the original 250 mM sucrose-EDTA buffer. This solution was then layered over a 2M sucrose/10 mM Tris-HCl buffer containing 1 mM EDTA and centrifuged for 1 hour at 80,000 g. A fluffy white interface resulted which was collected and resuspended in the 250 mM sucrose buffer. Protein content was determined by BCA assay (Pierce Chemical Company). The suspension was aliquoted and stored at −70° C.

For the ELISA, the cell membranes were added at a concentration of 400 ng/well to 96 well plates and were dried overnight at 25° C. The plates were washed with 0.5% Triton-X®/phosphate buffered saline (PBS), blocked with 5% fetal bovine serum (FBS)/PBS and washed again. Hybridoma supernatant (40μl) was diluted in 50 μl PBS and added to the wells overnight at 4° C. After washing, rabbit anti-mouse IgG (H+L) conjugated to horseradish peroxidase (HRP) (Zymed) was added to the wells for 2 hours at 25° C. The wells were washed with 0.5% Triton-X®/PBS and then incubated in the presence of ABTS (Bio-Rad substrate kit) for 20 minutes before monitoring OD at 405 and 650 nm.

The supernatants of hybridomas generated from the spleen cells of mice immunized with chronically infected cells and acutely infected cells screened positive to both noninfected cell membrane and infected cell membrane in the ELISA, indicating that the antibodies produced by the hybridomas are not HIV-1-specific. Of 1039 hybridomas generated from the spleen cells of mice immunized with infected cell membranes, 5 of their supernatants reacted strongly with infected cell membrane and reacted very weakly with uninfected cell membrane. Western blots were performed on the supernatants from these hybridoma cell lines and it was determined that three of the monoclonal antibodies produced bound to HIV-1 p55, one bound to HIV-1 p55 and p24, and the last did not produce a band in the Western blot (data not shown). The results of the ELISA are presented in Table 1 as ratios of values obtained for infected cell membranes compared to uninfected cell membranes.

One thousand one hundred and eighty-seven hybridomas were generated from the spleen cells of mice immunized with live HIV-$1_{MN}$. Four hybridoma cell lines were selected for further screening based on the results of an ELISA showing that antibodies in the four supernatants reacted strongly with infected cell membrane and very weakly with noninfected cell membrane.

The supernatants of the four hybridomas were subjected to limited dilution cloning and were screened by radioimmunoassay (RIA). Rabbit anti-mouse IgG labelled with $^{125}$I (R ∝ M IgG-$^{125}$I) was purified on a Sephadex G-50 column (NEN-DuPont). Uninfected H9 cells or H9 cells ($7.5 \times 10^5$ cells in 150 μl) infected with HIV-$1_{MN}$ were placed in 15 ml tubes. Fifty μl supernatant from each hybridoma was added to each of the tubes containing the noninfected and infected cells, an Cl the mixtures were incubated overnight at 4° C. The cells were washed 2 times with 2 ml PBS/50% Tween-20® with vortexing between washes. Fifty μl of the R ∝ M IgG-$^{125}$I (750,000 cpm) in PBS/5% FBS was added and the mixture was again incubated overnight at 4° C. After incubation, the cells were washed 3 times with PBS/50% Tween-20®. One hundred μl PBS/5% Triton-X® was added to disinfect the cells and 100 μl 1M NaOH was added to help transfer the label to scintillation vials. The samples were counted and the results of the RIA are presented in Table 1 below as ratios between the cpm values obtained for infected cells compared to cpm values for uninfected cells.

TABLE 1

| Hybridoma Cell Line | ELISA Ratio cpm inf/cpm uninf | | | RIA |
|---|---|---|---|---|
| | Run 1 | Run 2 | Run 3 | |
| 349 | 11.29 | 13.19 | 12.53 | 4.59 |
| 451 | 4.10 | 4.32 | 4.31 | 2.39 |
| 525 | 4.07 | 4.66 | 4.82 | 3.68 |
| HB 10726 | 5.76 | — | — | 9.81 |

Next, the four hybridoma cell lines were screened by immunofluorescence (IFA). Two ml of either uninfected or HIV-1 infected H9 cells (approximately $1 \times 10^6$ cells/ml) were placed a 10 ml sterile centrifuge tube with 10 ml PBS (without $Ca^{++}$ or $Mg^{++}$). The cells were washed once with 10 ml PBS by filling the tube, vortexing, spinning at 100 rpm for 5 minutes and aspirating all but about 100 μl supernatant leaving a "milky" cell suspension. While working in a laminar flow hood, 51 mm 10-well slides (Cell Line Association) were coated with cell suspension by flooding each well and then drawing the suspension back into the pipet tip. The coated slides were allowed to air dry and were then fixed in methanol at room temperature for 10 minutes. Supernatant from each of the four hybridomas was tested undiluted and at a 1:50 titer (supernatant diluted in 0.02% skim milk) for reactivity with slide preparations of uninfected and infected cells. Fifteen μl of undiluted or diluted supernatant was added to each slide well. The slides were incubated at 37° C. for 30 minutes and submersed in PBS with stirring for 5 minutes. The slides were then quickly rinsed in distilled water and air dried in a laminar flow hood. Sixteen μl goat-anti-mouse IgG (H+L) F(ab)$_2$ fragment (Cappel Biomedical) diluted 1:80 in 0.02% skim milk was added to each well. The slides were again incubated at 37° C. for 30 minutes and then submersed in PBS. The slides were rinsed in 0.01% Evans-blue solution in PBS for 5 seconds and rinsed 2 times in distilled water. The slides were examined by immunofluorescence and the results of the screening are presented in Table 2 wherein mouse IgG (MIgG), 5C5 antibody (anti-III$_B$, and Grp. 5 supernatant (from a hybridoma generated from the spleens of mice immunized with infected cell membranes) are control antibodies.

TABLE 2

| Antibodies | IFA with live cells | | |
|---|---|---|---|
| | Uninf-H9 | III$_B$-H9 | MN-H9 |
| MIgG | − | − | − |
| 5C5 | − | + | − |
| Grp. 5 | +++ | +++ | +++ |
| 349 | − | − | +(+/−) |
| 451 | − | − | +/− |
| 525 | − | − | +(+/−) |
| HB 10726 | − | ++ | ++ |

The hybridoma cell line, HB 10726, was selected as the most promising antibody on the basis of the RIA and immunofluorescence dam. The cell line did not have the highest binding ratio in the ELISA, but since the RIA and immunofluorescence results represent binding to live infected cells while the ELISA represents binding to dried cells membranes, the RIA data is more significant. The cell line was subcloned twice and the monoclonal antibody it produced was designated NM-01. Mice were intraperitoneally injected with the cell line by standard procedures and monoclonal antibody NM-01 was concentrated from the ascites fluid by protein A affinity column purification (Pierce). The isotype of antibody NM-01 was determined to be IgG$_{2b}$ by type specific antisera (Bio-Rad). The antibody (1.8 mg/ml) was diluted in RPMI 1640 medium with 15% FBS and utilized in the following examples.

Example 2

In order to characterize the viral epitope recognized by monoclonal antibody NM-01, the antibody was first screened by Western blot analysis for reactivity with purified MN and III$_B$ virion proteins and then by ELISA for reactivity with overlapping peptides corresponding to the amino acid sequence of the V3 loop region of HIV-1 gp120.

A. Western Blot Analysis

MN and III$_B$ virions purified from culture supernatants of infected H9 cells were disrupted in 1.3% SDS/3%/3-mercaptoethanol and then subjected to electrophoresis in a 0.1% SDS/10% polyacrylamide gel. After transfer of the proteins to nitrocellulose paper, strips were incubated overnight with monoclonal antibody NM-01 in blocking buffer (0.02M Tris-HCl, pH 7.4, 0.1M NaCl, 0.05% normal goat serum and 5% nonfat dry milk) at 4° C. and then washed in 0.02M Tris-HCl, pH 7.4, 0.1M NaCl and 0.3% Tween®. The strips were then incubated with biotinylated goat anti-mouse IgG (Zymed) for 1 hour, washed and reacted with $^{125}$I-Streptavidin (Amersham, Arlington Heights, Ill.) for an additional hour at 4° C. monoclonal antibody NM-01 reactivity was monitored by autoradiography.

The autoradiographic results are presented in FIG. 1 wherein: lanes 1 and 3 of the gel contained uninfected H9 cell membrane; lane 4 contained HIV-1$_{MN}$ infected H9 cell membrane; lanes 2 and 5 contained HIV-1$_{MN}$ virus; and lanes 6 and 7 contained HIV-1$_{IIIB}$ virus. Antibody NM-01 was reacted with the proteins in lanes 1, 2 and 6 while HIV-1 sero-positive patient serum was reacted with the proteins in lanes 3–5 and 7.

Monoclonal antibody NM-01 exhibited reactivity with MN and III$_B$ viral proteins having an apparent molecular weight of 120 kD, but did not react with any other viral antigens, indicating that the antibody recognizes an epitope of gp120.

For comparison, monoclonal antibodies F58/H3 and P4/D10 described in the Wahren et al. PCT Publication No. WO91/11198 were obtained from the ECACC (Accession Nos. 90011607 and 90011608, respectively) and were tested for binding to recombinant HIV-1$_{MN}$ gp120 (Agmed, Inc., Bedford, Mass.), recombinant HIV-1$_{IIIB}$ gp120 (DuPont-NEN, Boston, Mass.), native HIV-1$_{MN}$ gp120 and native HIV-1$_{IIIB}$ gp120 in a Western blot along with monoclonal antibody NM-01 . The Western blot was performed essentially as described above except that rabbit anti-mouse secondary antibody was utilized in a colorimetric assay to detect binding of the antibodies. Monoclonal antibody NM-01 reacted with native MN and III$_B$ gp120 and with both MN and III$_B$-derived recombinant gp120. Monoclonal antibodies F58/H3 and P4/D10, however, only reacted with native HIV-1$_{IIIB}$ gp120 and recombinant gp120 derived from HIV-1$_{IIIB}$.

B. Epitope Mapping by ELISA

To identify the specific epitope of gp120 recognized by antibody NM-01, the antibody was screened by ELISA for reactivity with overlapping peptides corresponding to the V$_3$ loop region of gp120. The peptides, synthesized by Multiple Peptide Systems, San Diego, Calif., corresponded to amino acids 302–316, 312–326 and 322–336 of HIV-1$_{MN}$ gp120.

The three peptides (250 ng/50 µl 0.1M borate buffer, pH 8.0, per well) were incubated overnight at 37° C. in Immulon 2 plates (Dynatech). The plates were washed with PBS and blocked with PBS/0.1% Tween®/0.1% Bovine Serum Albumin (BSA) for 1 hour at room temperature. The blocking agent was removed and differing amounts of antibody NM-01 or mouse IgG (MIgG), diluted in 100 µl HAT media, were added to the plates. The antibody was allowed to react for 2 hours at room temperature. The plates were then washed 10 times with tap water. An HRP-conjugated rabbit anti-mouse second antibody, diluted 1:1000, was brought up in PBS/0.05% Tween®/0.5% BSA, and 100 µl were added per well. The plates were incubated 1 hour at room temperature and then washed 10 times with tap water. ABTS substrate (Bio-Rad) was added for 20 minutes, and the plates were counted at 650 nm. SEQ ID NOs: 2–4 set out the amino acid sequences of the peptides and Table 3 sets out the results of the assay utilizing the overlapping peptides wherein the antibody MIgG and HAT medium were negative controls.

TABLE 3

| | | | Antibody NM-01 | | |
|---|---|---|---|---|---|
| Peptide | MIgG 500 ng | HAT medium | 4.75 ng | 9.50 ng | 19.0 ng |
| SEQ ID NO: 2 (aa 302–316) CTRPNYNKRKRIHIG | .049 | .025 | .024 | .024 | .024 |
| SEQ ID NO: 3 (aa 312–326) RIHIGPGRAFYTTKN | .043 | .029 | .781 | .827 | 1.141 |
| SEQ ID NO: 4 (aa 322–336) YTTKNIIGTIRQAHC | .042 | .029 | .030 | .028 | .030 |

While there was no detectable reactivity over background of monoclonal antibody NM-01 with the peptides corresponding to amino acids 302–316 or 322–336 of the V$_3$ loop, binding of the antibody to the peptide representing amino acids 312–326 was apparent. A control antibody, mouse IgG, did not bind to the peptides.

Example 3

The demonstration that monoclonal antibody NM-01 binds to the V$_3$ loop region of HIV-1$_{MN}$ gp 120 prompted further studies on the extent of this reactivity with other HIV-1 isolates. The antibody was screened by ELISA for reactivity with peptides corresponding to the V$_3$ loop region of HIV-1 isolates III$_B$, RF, CDC4, NY/5, Z6, Z2 and ELI. The amino acid sequences of the peptides are set out below in Table 4 and in the sequence listing as SEQ ID NOs: 5–12, respectively.

TABLE 4

| Isolate | Peptide amino acid Sequence | |
|---|---|---|
| MN | RIHIGPGRAFYTTKN | (SEQ ID: NO: 5) |
| III$_B$ | IRIGPGRAFVTIGK | (SEQ ID: NO: 6) |
| RF | NTRKSIKGPGRVIYATGQ | (SEQ ID: |

TABLE 4-continued

| Isolate | Peptide amino acid Sequence | |
|---|---|---|
| | | NO: 7) |
| CDC4 | CHTRKRVTLGPGRVWYTTGE | (SEQ ID: NO: 8) |
| NY/5 | CNTKKGIAIGPGRTLYAREK | (SEQ ID: NO: 9) |
| Z6 | CNTRQSTPIGLGQALYTTRGRTK | (SEQ ID: NO: 10) |
| Z2 | CNIRQRTSIGLGQALYTTKTRS | (SEQ ID: NO: 11) |
| ELI | CNTRQRTPIGLGQSLYTTRSRS | (SEQ ID: NO: 12) |

Figure 2:
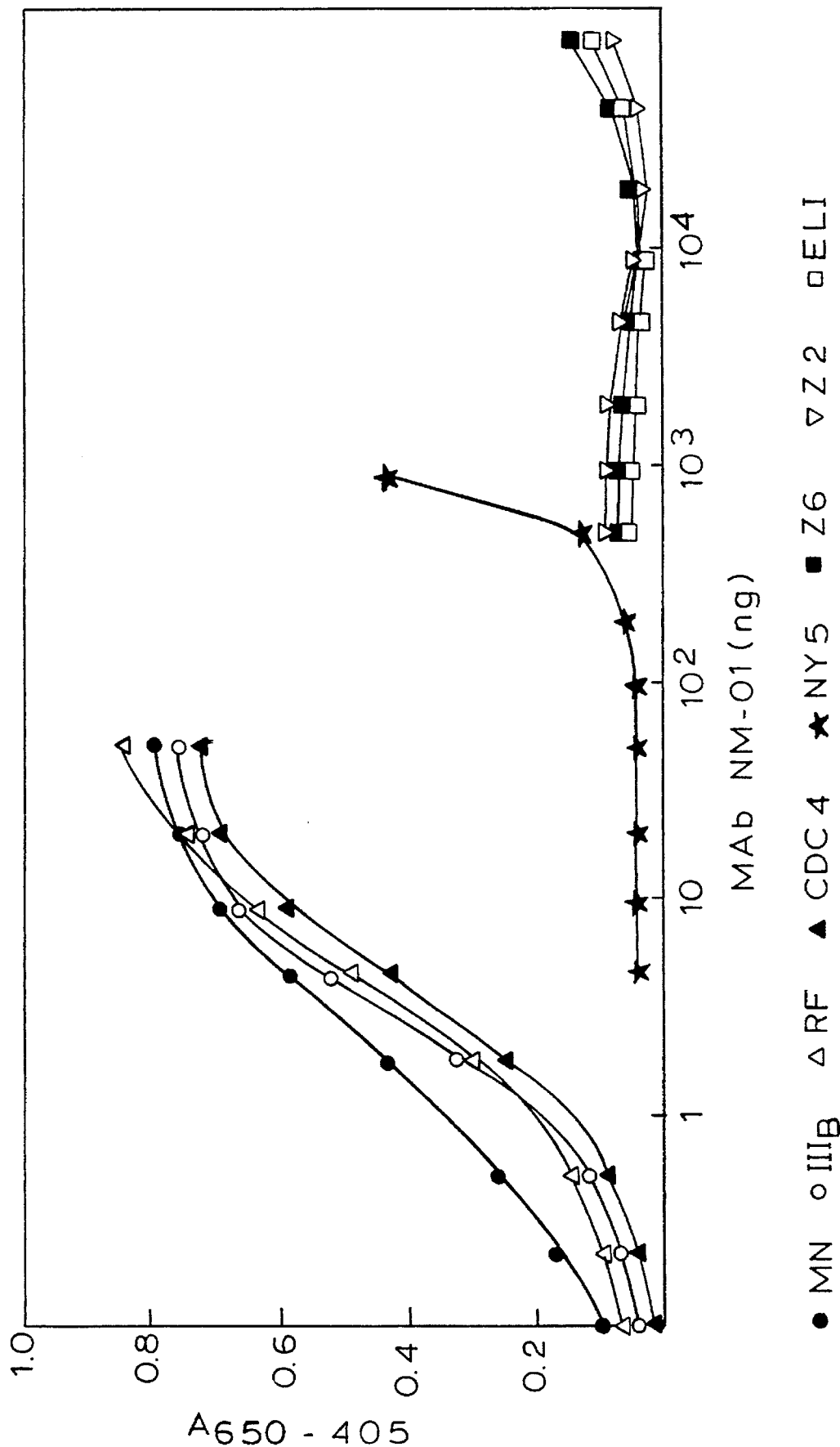
FIG. 2 graphically represents the results of immunoreactivity testing of an antibody of the invention with peptides corresponding to the V$_3$ loop region of different HIV-1 strains.

The peptides (250 ng/0.1M borate buffer, pH 8.0, synthesized by American Biotechnologies, Cambridge, Mass.) were incubated overnight at 4° C. in Immulon 2 plates (Dynatech). The plates were washed with PBS, blocked with 0.1% Tween®/0.1% BSA/PBS for 2 hours at 25° C. and then incubated with monoclonal antibody NM-01 for 1 hour at 37° C. After washing with tap water, the plates were incubated with HRP-conjugated rabbit anti-mouse secondary antibody for 1 hour at 25° C. and then with ABTS substrate (Bio-Rad) for 20 minutes. Reactivity was determined by monitoring OD at 650–405 nm. The results of the assay are presented in FIG. 2.

Monoclonal antibody NM-01 reacted with loop peptides from the MN (closed circle), III$_B$ (open circle), RF (open triangle) and CDC4 (closed triangle) isolates. The binding of the antibody to the III$_B$, RF and CDC4 peptides was comparable to that obtained with the MN peptide. The antibody also showed a lesser affinity for the NY/5 peptide (star). Monoclonal antibody NM-01 is also putatively reactive with the RF-like peptide set out in SEQ ID NO: 13. In contrast, there was little, if any, reactivity with loop peptides from Z6 (closed square), Z2 (inverted open triangle) and ELI (open square) isolates. These results indicate that monoclonal antibody NM-01 recognizes, in particular, an epitope of the V$_3$ loop of gp120 of HIV-1 isolates having the amino acid sequence set in SEQ ID NO: 1, G-P-G-R.

Monoclonal antibodies F58/H3 and P4/D10 were also tested for reactivity to the MN, III$_B$, RF-like, CDC4, NY/5, Z2, Z6 and ELI V$_3$ loop peptides. In constrast to monoclonal antibody NM-01, both monoclonal antibodies F58/H3 and P4/D10 only reacted with III$_B$ peptide and to a lesser extent with the RF-like peptide set out in SEQ ID NO: 14.

Figure 5:
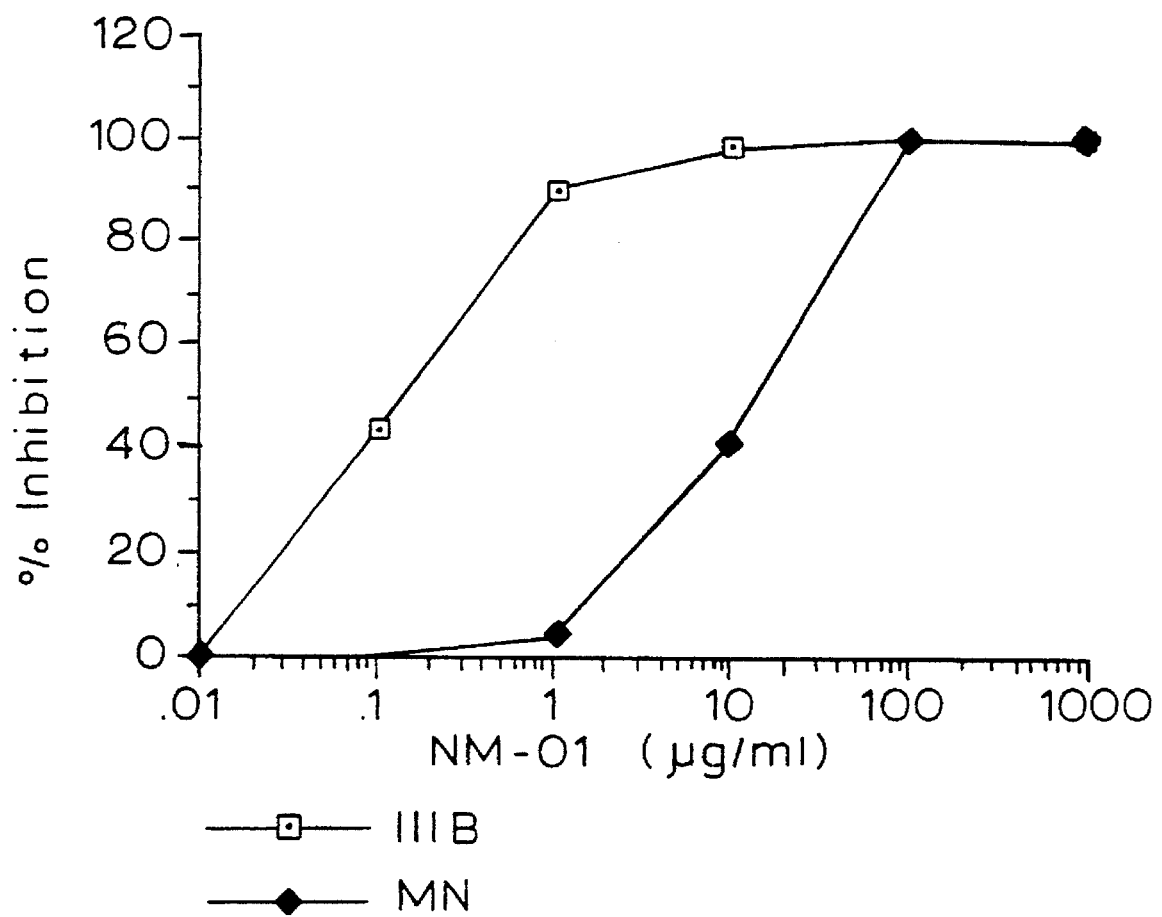

Another anti-HIV-1 gp 120 monoclonal antibody, monoclonal antibody BAT123, is described in Liou et at., supra as being reactive with MN-like and III$_B$-like and III$_B$-like V$_3$ loop peptides and unreactive with an RF-like peptide (SEQ ID NO: 13) (see FIG. 5A on page 3972 of the Liou et at., supra). These reported reactivities are different from those of monoclonal antibody NM-01 as described in the foregoing paragraph. While both antibodies NM-01 and BAT123 bind relatively well to III$_B$ peptide, an approximately fifty-fold increase in the concentration of BAT123 is required to obtain binding to an MN peptide that is similar to the binding of NM-01. Moreover, NM-01 is reactive with the RF peptide set out in Table 4 and SEQ ID NO: 7 and the RF-like peptide set out in SEQ ID NO: 14, while BAT123 does not bind to the RF-like peptide of SEQ ID NO: 13 even at antibody concentrations of 10,000 µg/ml.

In a competition assay, binding of monoclonal antibodies NM-01, F58/H3 and P4; /D10 was measured in the presence of each of the overlapping III$_B$ loop peptides (which are portions of SEQ ID NO: 7): IRIQRGPG (Peptide 1), RIQRGPGR (Peptide 2), IQRGPGRA (Peptide 3), QRGPGRAF (Peptide 4), RGPGRAFV (Peptide 5) and GPGRAFVT (Peptide 6). The assay was performed as follows. One hundred μl recombinant $III_B$ gp120 (0.5 μg/ml in PBS) was coated on an Immuno 4 plate (Dynatech) and incubated at room temperature overnight. The plate was then blocked with 250 μl blocking buffer (5% normal rabbit serum in PBS) for 1 hour at 37° C. Monoclonal antibodies NM-01, F58/H3 and P4/D10 were diluted to 10 μg/ml with blocking buffer and the six $III_B$ loop peptides each were diluted to 100 μg/ml with blocking buffer. Each of the antibodies was then separately mixed with each peptide in 1:1 volume to give a final antibody concentration of 5 μg/ml and peptide concentration of 50 μg/ml. The mixtures of antibody and peptide were allowed incubate at room temperature for 40 minutes and were then transferred into a well (100 μl/well) on the blocked, gp120-coated plate for assay. Control wells contained no peptide and 5 μg/ml of an antibody. The plates were incubated for 40 minutes at 37° C. and then washed four times with washing buffer (0.005% Tween-20 in PBS). Rabbit anti-mouse/HRP linked antibody (100 μl/well) was used as secondary antibody at 1:1000 dilution in blocking buffer and was incubated for 1 hour at 37° C. The plate was then washed again and developed using 100 μl /well TMB (tetra methyl benzidine). Development was stopped with 100° l/well $H_2SO_4$ (0.36N) and the plate was read at 450 nm–650 nm.

Figure 3:
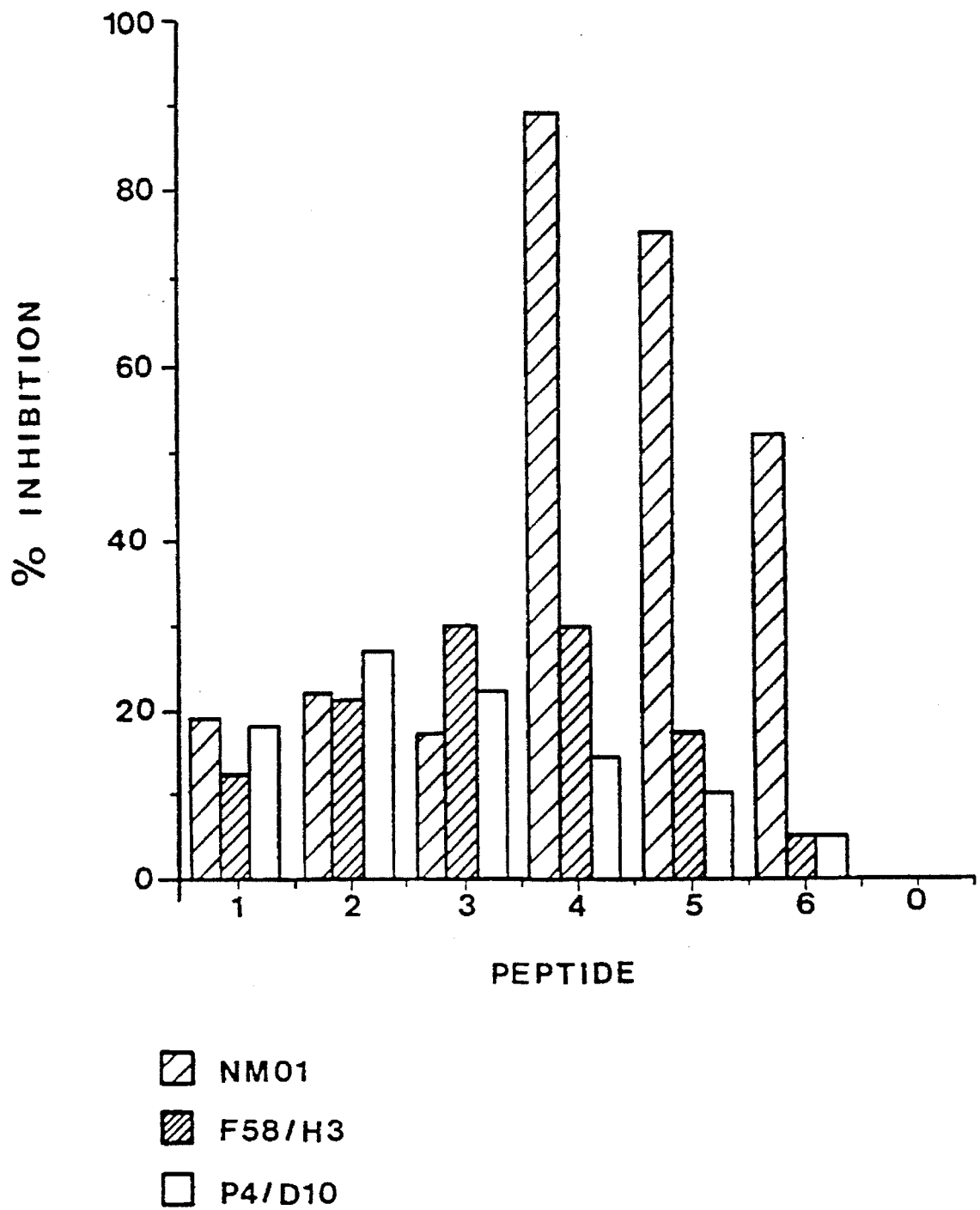
FIG. 3 is a bar graph showing effects of peptides corresponding to the V$_3$ loop region on binding of an antibody of the invention and two other anti-HIV antibodies to gp120.

The results of the competition assay are presented in FIG. 3. In this assay, Peptide 4 was the strongest inhibitor of monoclonal antibody NM-01 binding to recombinant $III_B$ gp120, while Peptides 3 and 4 were the strongest inhibitors of monoclonal antibody F58/H3 binding and Peptide 2 was the strongest inhibitor of monoclonal antibody P4/D10 binding.

Example 4

Monoclonal antibody NM-01 was tested for the ability to neutralize infection of H9 cells by live HIV-1 strains MN, $III_B$, and RF as measured by reverse transcriptase assay and HIV-1 strains MN and $III_B$ as measured by p24 assay.

Reverse Transcriptase and p24 Assays

Figure 4A:
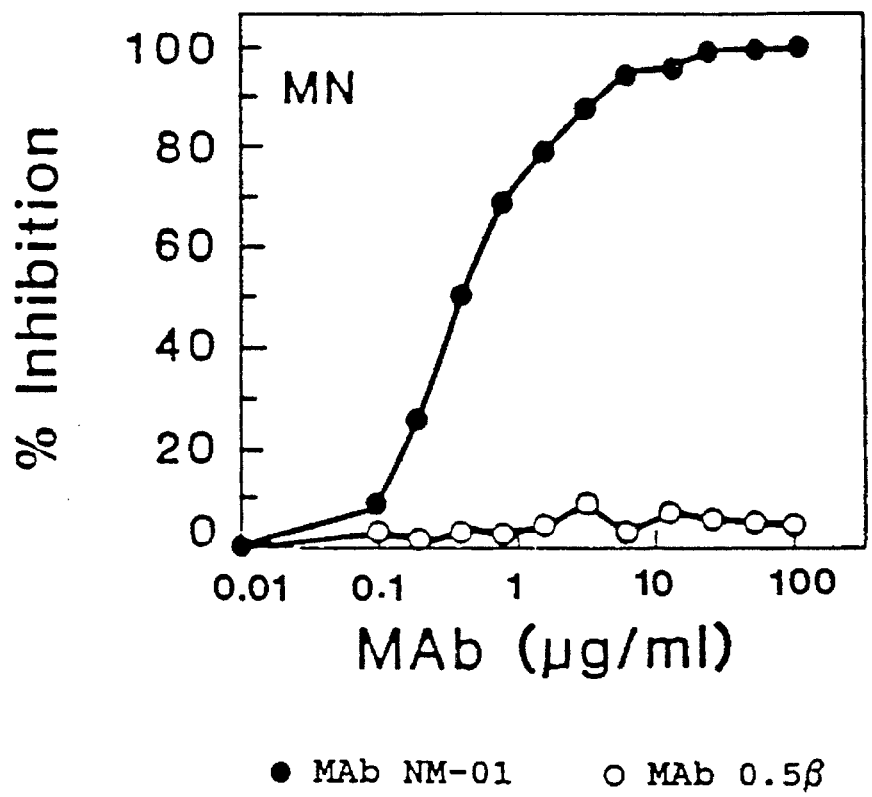
FIGS. 4A to 4C, 5, 6A to 6B, 7A to 7B, 8 and 9A to 9B graphically report the results of the screening by reverse transcriptase, p24, MT-2 and syncytia formation assays, respectively, of a monoclonal antibody of the invention for the ability to neutralize infection of H9 cells by live HIV-1 strains.

Dilutions of monoclonal antibody NM-01 were incubated with 40 $TCID_{50}$ of MN or 100 $TCID_{50}$ of $III_B$ live virus in 96-well plates for 1.5 hour at 37° C. monoclonal antibody 0.5 β (AIDS Research and Reference Reagent Program Catalog, National Institute of Allergy and Infectious Diseases) was used as both a positive and negative control in the RT studies; it binds to gp120 of HIV-$1_{IIIB}$. H9 cells (2.5× $10^4$) were then added to each well and the plates were incubated for another hour at 37° C. The H9 cell suspension was then diluted in RPMI 1640/15% FBS and incubated in a 24 well plate at 37° C. Virus production was determined by reverse transcriptase (RT) assay performed on day 7 as described in Poiesz et al., *Proc. Natl. Acad. Sci. USA*, 77, pp. 7415–7419 (1980) and by p24 assay performed on day 5 (Dupont HIV-1 p24 Core Profile ELISA). Results of the two assays are presented in FIGS. 4A to 4B and 5, respectively.

Figure 4B:
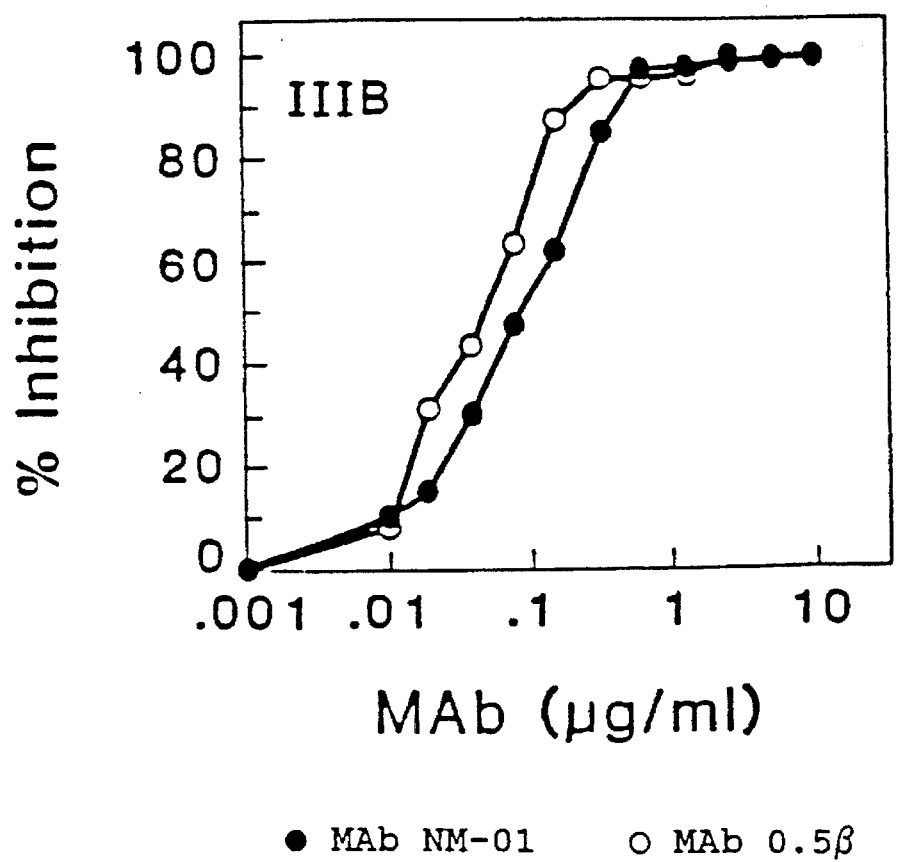
Figure 4C:
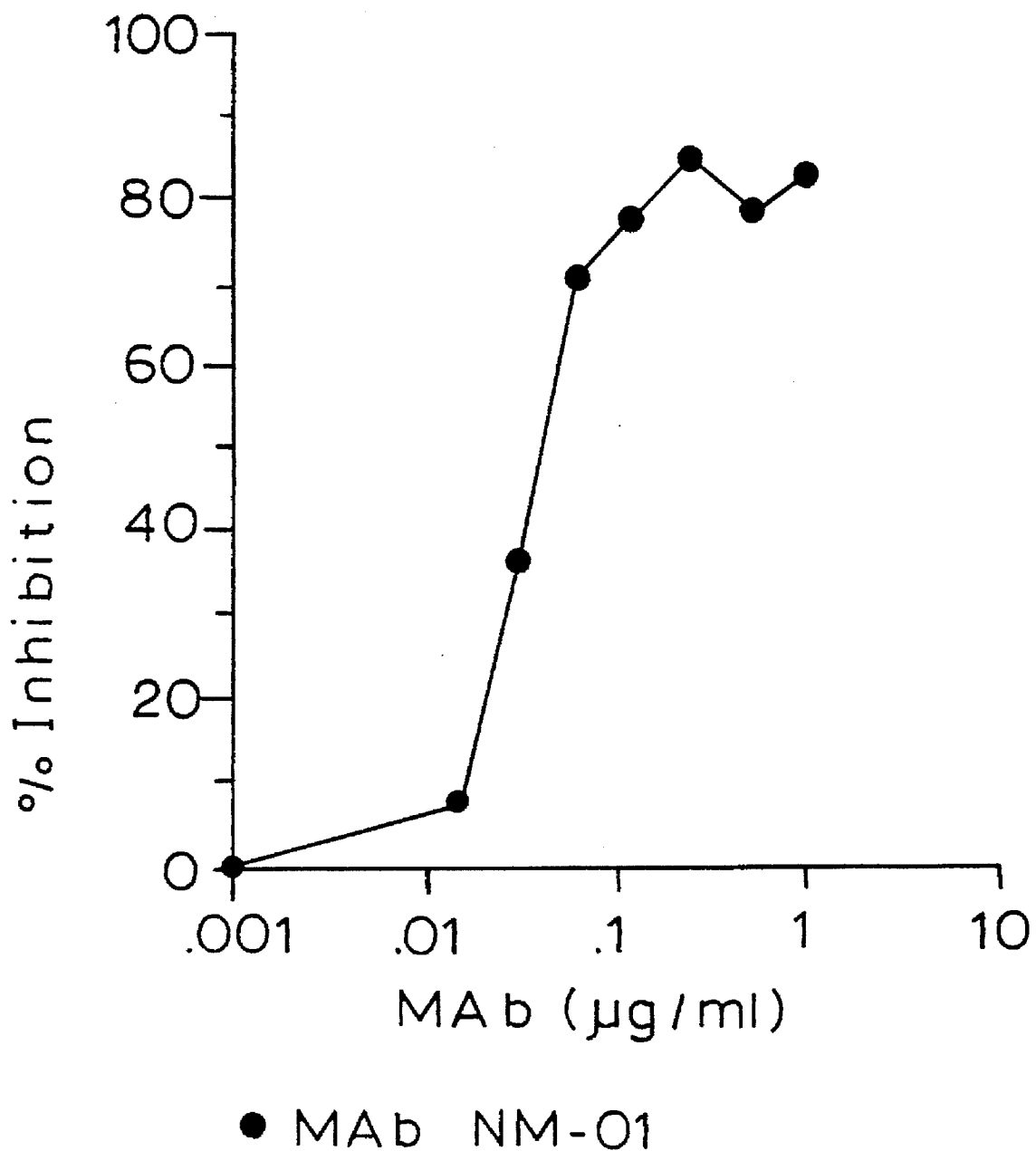

Monoclonal antibody NM-01 (closed circles in FIG. 4A) completely neutralized infectivity of live MN virus, as determined by RT assay, at concentrations of 10–100 μg/ml. Moreover, the use of the antibody at a concentration of <1 μ/ml resulted in 50% inhibition of viral infectivity ($ID_{50}$). These findings were in contrast to the absence of detectable neutralization with monoclonal antibody 0.5 β (open circles, FIG. 4A). Monoclonal antibody NM-01 also neutralized live $III_B$ virus at an $ID_{50}$ of approximately 0.1 μg/ml (FIG. 4B). Monoclonal antibody 0.5 β neutralized $III_B$ slightly more effectively than monoclonal antibody NM-01 FIG. 4B). Similar results were obtained for HIV-1 MN and $III_B$ in the p24 assay. See FIG. 5. In the reverse transcriptase assay, monoclonal antibody NM-01 also inhibited live RF virus at an $ID_{50}$ of about 0.05 μg/ml (FIG. 4C).

These data indicate that monoclonal antibody NM-01 neutralizes infectivity of at least three different strains of HIV-1.

Figure 6A:
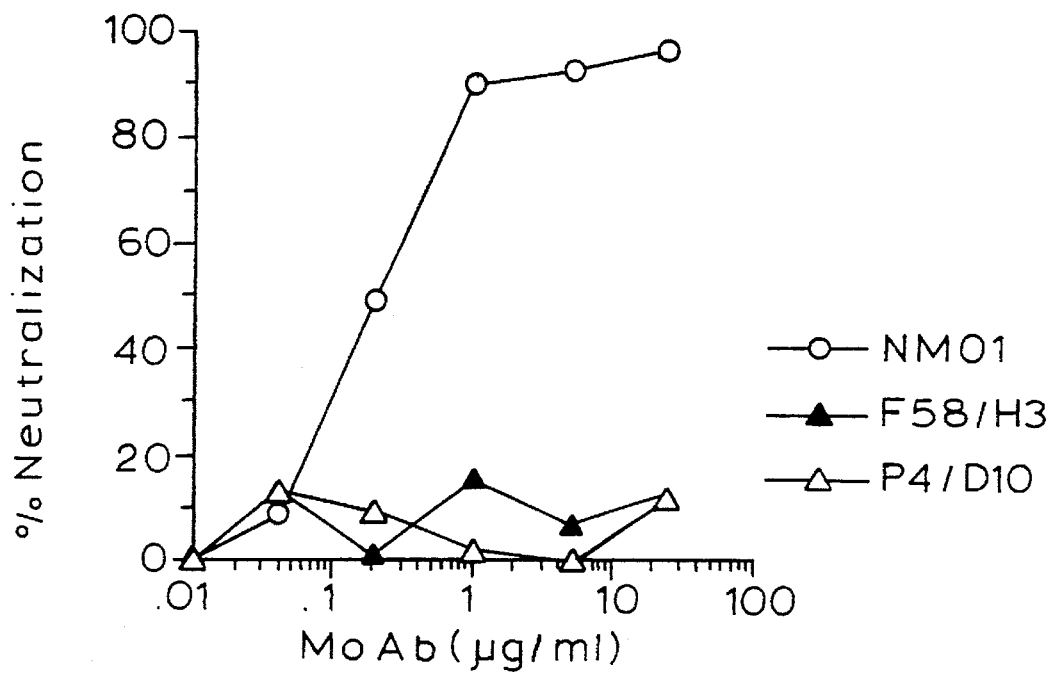
Figure 6B:
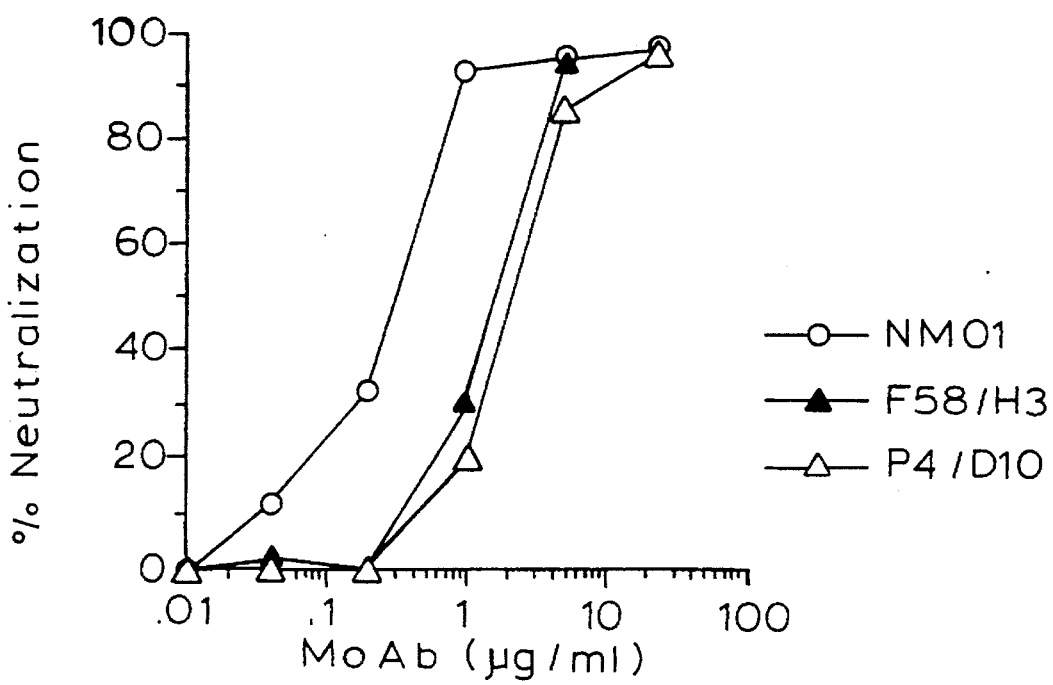
Figure 7A:
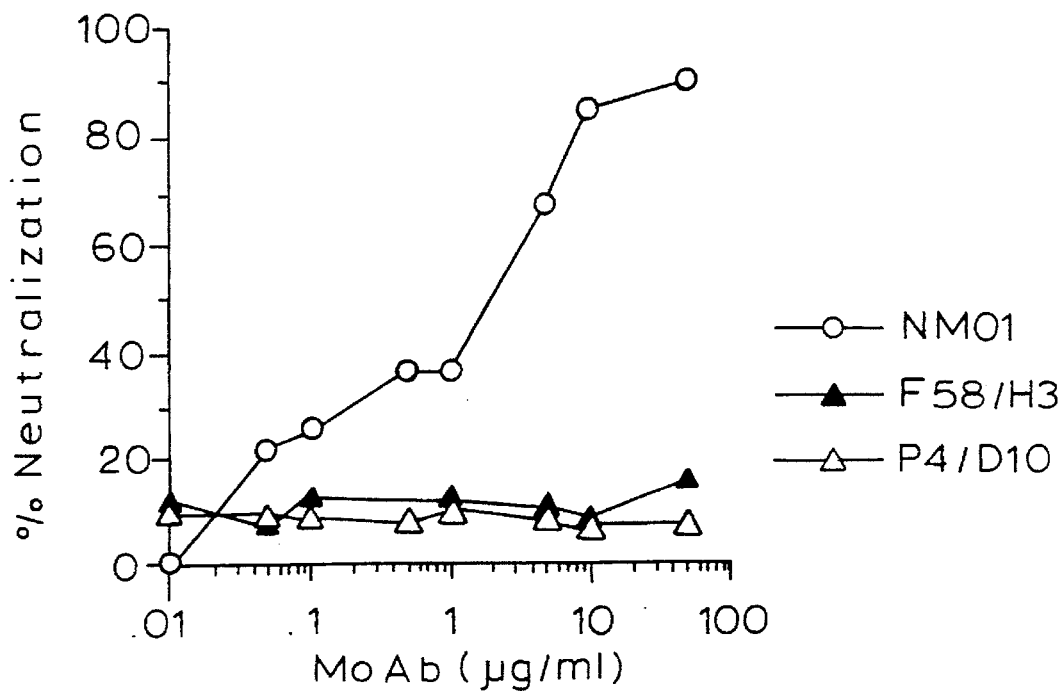
Figure 7B:
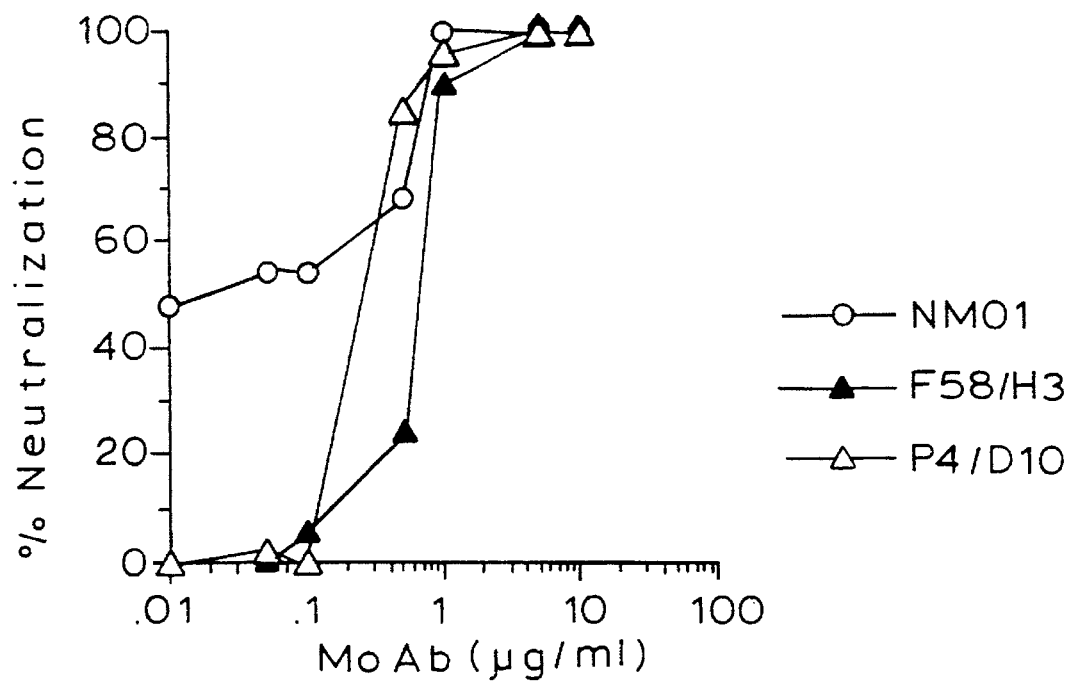

The ability of monoclonal antibodies F58/H3 and P4/D10 to neutralize infection of H9 cells by live HIV-1 strains MN and $III_B$ was also measured by reverse transcriptase assay and by p24 assay as described above for monoclonal antibody NM-01. The results of the assays are presented in FIGS. 6A to 6B and 7A to 7B. In the RT assay monoclonal antibody NM-01 was again found to completely neutralize infectivity of live MN virus at concentrations of 10–100 μg/ml and the use of the antibody at a concentration of <1 μg/ml resulted in 50% inhibition of viral infectivity ($ID_{50}$) (see open circles in FIG. 6A). These findings were in contrast to the lack of detectable neutralization with monoclonal antibodies F58/H3 and P4/D10 (see closed and open triangles in FIG. 6A). In the RT assay using live $III_B$ virus, monoclonal antibody NM-01 neutralized the virus at an $ID_{50}$ of approximately 0.1 μg/ml (open circles in FIG. 6B). Monoclonal antibodies F58/H3 and P4/D10 neutralized $III_B$ less effectively than monoclonal antibody NM-01 (see FIG. 6B) with $IC_{50}$s of about 1.1 and 1.2 μg/ml, respectively. Similar results were obtained for the three monoclonal antibodies using HIV-1 MN and $III_B$ in the p24 assay (see FIGS. 7A and 7B).

Example 5

Neutralization of live HIV-1 infectivity as demonstrated by reverse transcriptase and p24 assays was extended by studying the effects of monoclonal antibody NM-01 in MT-2 assays utilizing live MN and $III_B$ virus and in syncytium formation assays utilizing live MN, $III_B$ and RF virus.

A. MT-2 Assay

Figure 8:
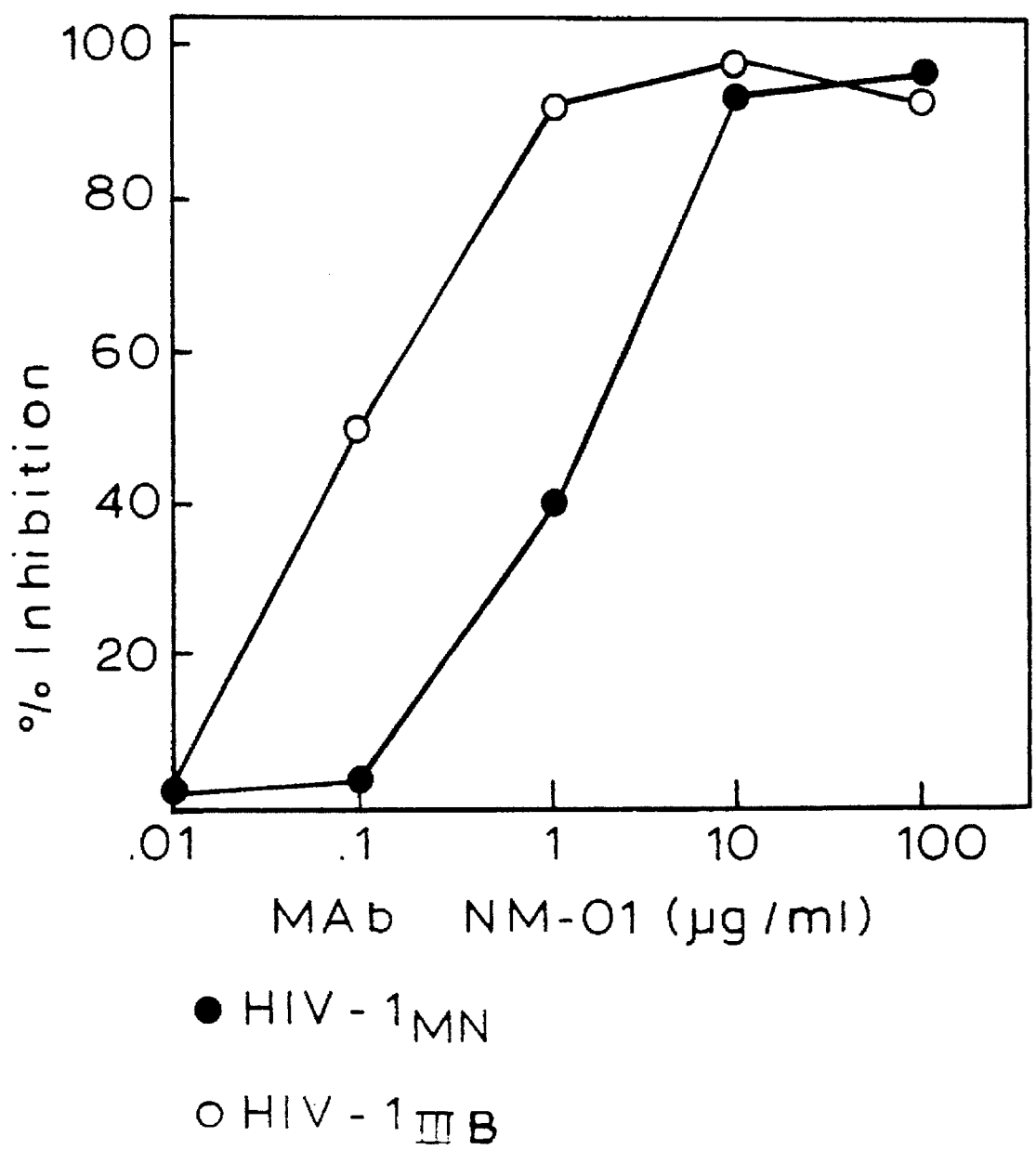

The MT-2 assay was performed as described in Richman, *AIDS Research and Reference Reagent Program*, Courier No. 90-01, pp. 6–9 (1990) with certain modifications. Live MN and $III_B$ virus were incubated with dilutions of monoclonal antibody NM-01 for 1.5 hours at 4° C. in 96- well plates. MT-2 cells (8×$10^5$) were added to the wells and the plates were incubated for 3 days at 37° C. MTT dye reduction according to Mosmann, *J. Immunol. Meth.*, 65, pp. 55–63 (1983) and Pauwels et at., *J. Virol. Meth.*, 20, pp. 55–63 (1983) was then performed to determine cell viability. Results of the MT-2 assay confirm the results of the RT and p24 assays and are presented in FIG. 8 wherein the open circles track values for $III_B$ (100 $TCID_{50}$) and closed circles track values for MN (40 $TCID_{50}$).

Monoclonal antibody NM-01 neutralized the infectivity of live MN and $III_B$ isolates at $ID_{50}$s of 2.0 and 0.1 μg/ml, respectively.

B. Syncytium Formation Assay

Figure 9A:
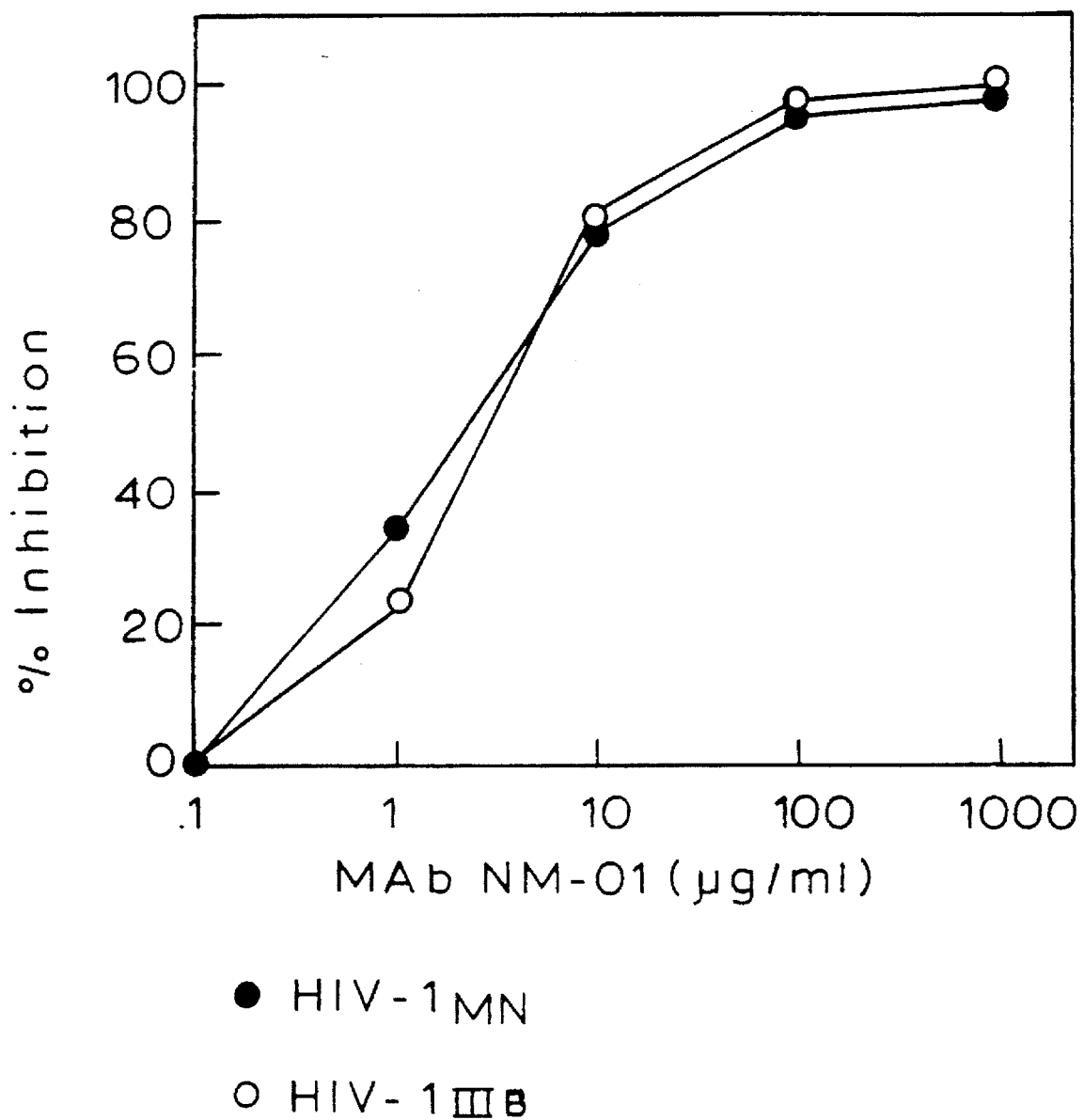

The binding inhibition assay was a modification of that described previously in Johnson and Walker, Eds., *Techniques in HIV-1 Research*, Stockton Press, New York, N.Y., pp. 92–97 (1990). Briefly, H9 cells chronically infected with either MN or III$_B$ virus were incubated with dilutions of monoclonal antibody NM-01 for 1 hour at 37° C. C8166 cells were then added to each well and incubated for 2 hours at 37° C. Syncytia greater than three lymphocyte cell diameters were counted and compared to that obtained for control infected H9 cells treated in the absence of antibody. Results of the syncytium formation assay also confirm the results of the RT and p24 assays and are presented in FIG. 9A wherein open circles track values for III$_B$ (100 TCID$_{50}$) and closed circles track values for MN (40 TCID$_{50}$). Monoclonal antibody NM-01 inhibited syncytium formation by MN-infected H9 cells at an ID$_{50}$ of 2 µg/ml, and by III$_B$-infected H9 cells at an ID$_{50}$ of 3 µg/ml.

Figure 9B:
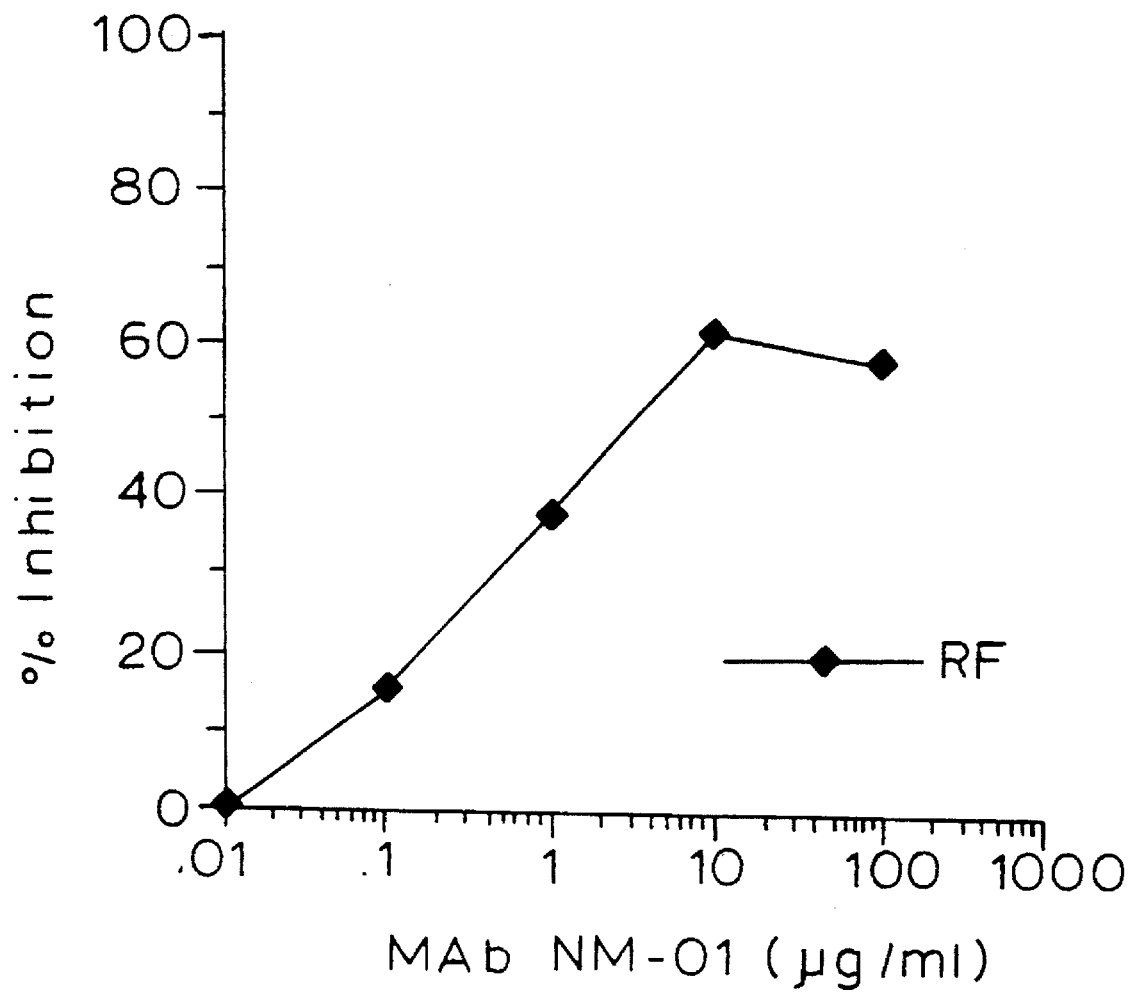

Corresponding syncytium formation inhibition results are presented for monoclonal antibody BAT123 in Table III of WO 88/09181. While 25 µg monoclonal antibody NM-01 inhibits about 85% of syncytium formation by MN-infected cells, 25 µg of BAT123 is reported to inhibit 51%, and while 25 µg NM-01 inhibits about 85% of syncytium formation by III$_B$-infected cells, BAT123 is reported to inhibit 77.8%. 25 µg BAT123 is also reported to inhibit syncytium formation by RF-infected cells by 51%. Monoclonal antibody NM-01 also inhibits syncytium formation by RF-infected cells (see FIG. 9B). In the assay described in the foregoing paragraph, a concentration of 25 µg NM-01 inhibits about 59% of syncytium formation by RF-infected cells. Monoclonal antibody NM-01 inhibited syncytium formation by RF-infected cells at an ID$_{50}$ of 4 µg/ml.

Taken together, the results of the reverse transcriptase, p24, MT-2 and syncytia formation assays of Examples 4 and 5 indicate that monoclonal antibody NM-01 neutralizes binding and infectivity of diverse HIV-1 strains at concentrations less than 10 µg/ml.

Example 6

In order to confirm that monoclonal antibody NM-01 blocks infectivity of HIV-1 MN and III$_B$ by binding to a portion of the gp120 V$_3$ loop, V$_3$ loop peptides were tested for the ability to block neutralization with the antibody.

Figure 10:
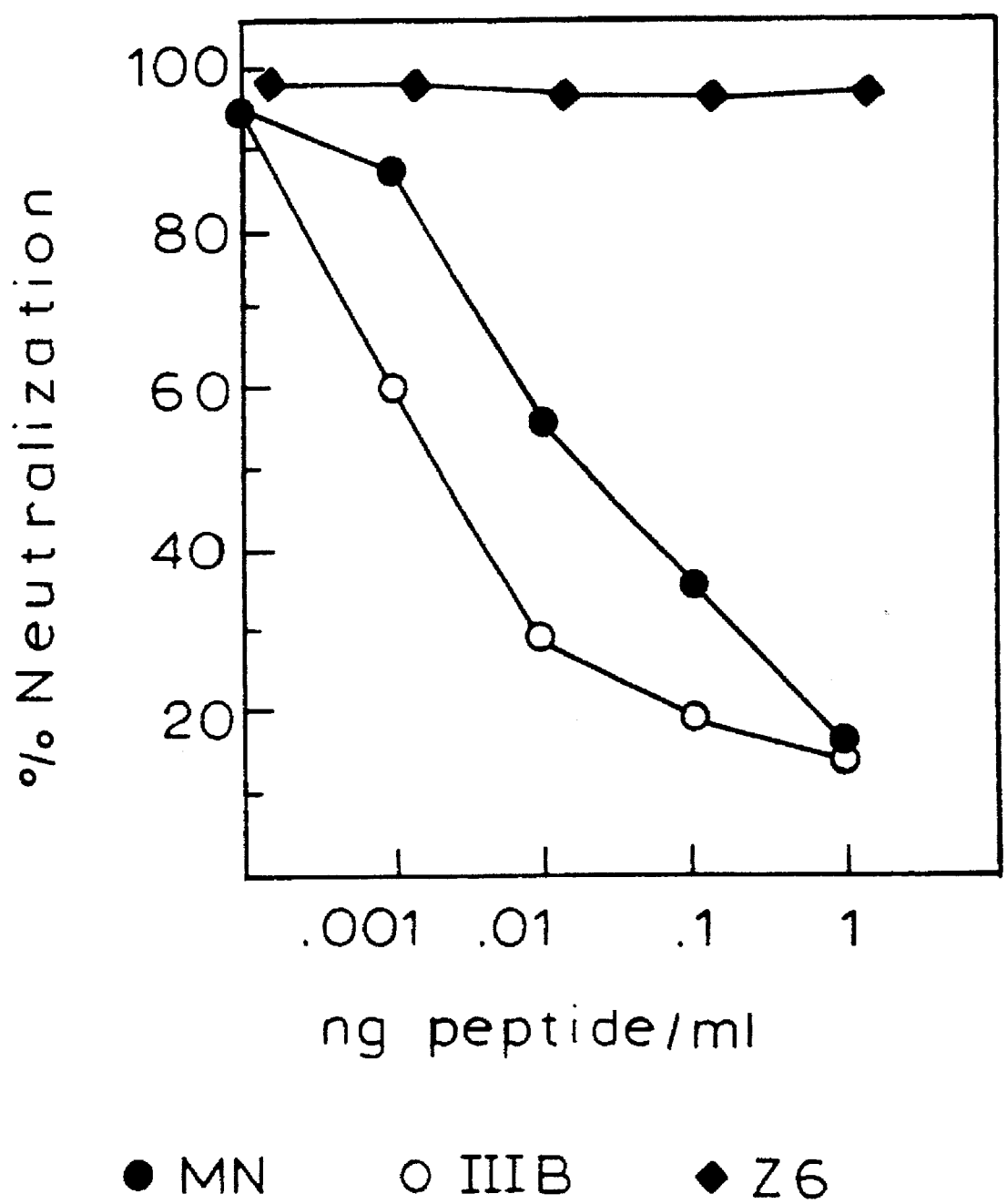
FIG. 10 graphically reports the results of an assay for determination of peptide blockage of neutralization of infectivity for an antibody of the invention.

Monoclonal antibody NM-01 was incubated with the varying concentrations of peptides corresponding to the V$_3$ loops of the MN, III$_B$ and Z6 strains (the sequences of the peptides are given in Table 4, above) for 30 minutes at 37° C. before adding 100 TCID$_{50}$ of live III$_B$ virus. H9 cells were then added for 1 hour and RT activity was determined after growth of the cells in complete medium for 7 days as described in Example 4. The results of the assay are presented in FIG. 10.

While monoclonal antibody NM-01 completely neutralized III$_B$ infectivity at the lowest concentrations of peptide, this effect was progressively blocked by preincubation with increasing concentrations of MN (closed circle) and III$_B$ (open circle) loop peptides. There was no detectable effect with similar concentrations of the peptide corresponding to the V$_3$ loop of the Z6 strain (closed diamond) which does not have the sequence of amino acids recognized by monoclonal antibody NM-01. These results indicate that monoclonal antibody NM-01 blocks infectivity of HIV-1 by reacting with a specific portion of the gp120 V$_3$ domain.

Example 7

Studies were also carried out to determine whether the monoclonal antibody NM-01 can activate the complement pathway and potentially destroy HIV-1 virions. Rabbit serum was used as a source of complement.

Lysis of HIV-1 *with Monoclonal Antibody NM-01 and Complement*

H9 cells infected with the HIV-1 III$_B$ strain were washed in cytotoxicity medium (Cedarlane Lab. Ltd.). The cells were resuspended in cytotoxicity medium either in the absence or in the presence of 40 µg/ml monoclonal antibody NM-01. After incubation for 2 hours at 4° C., rabbit complement (lowotox-MA; Cedarlane Lab. Ltd.) was added at a dilution of 1:6. The cell suspension was incubated at 4° C. for 20 minutes and then 37° C. for 45 minutes. The cells were doubly fixed with 2% glutaraldehyde/0.1M phosphate buffer and 1% osmium tetroxide/0.1M phosphate buffer. After embedding in epoxy resin, thin sections were cut and doubly stained with uranyl acetate and lead citrate. FIGS. 11A to 11B, 12A to 12F and 13A to 13F are representative electron micrographs of the thin sections.

Figure 11A:
FIGS. 11A to 11B, 12A to 12F, and 13A to 13F are electron micrographs of HIV-1 particles which were treated with a combination of a monoclonal antibody of the invention and complement.
Figure 11B:
Figure 12A:
Figure 12B:
Figure 12C:
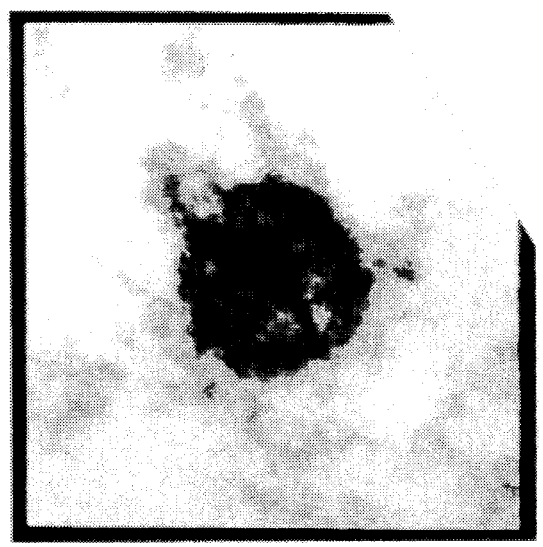
Figure 12F:
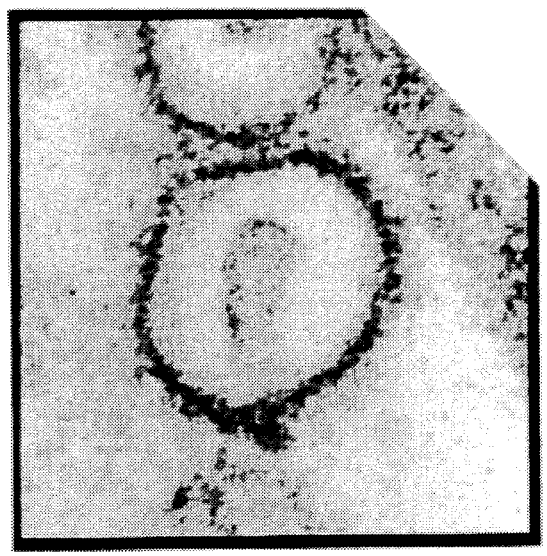
Figure 12E:
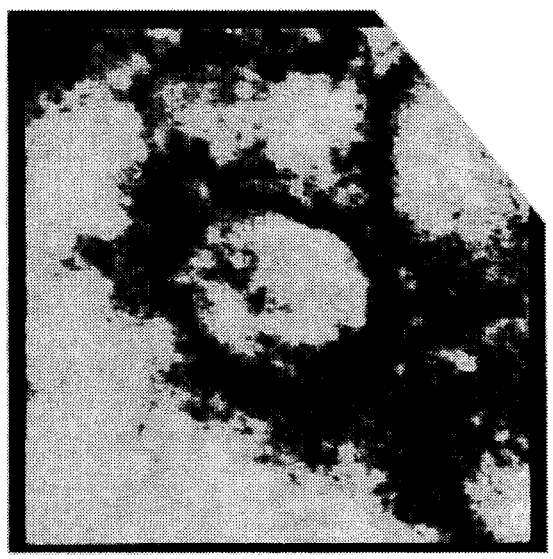
Figure 12D:
Figure 13C:
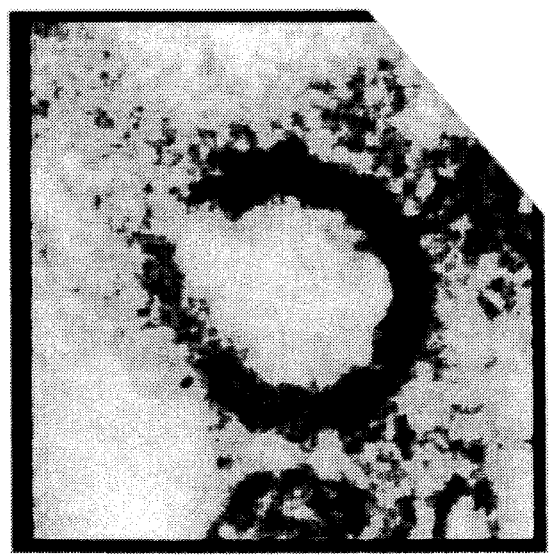
Figure 13B:
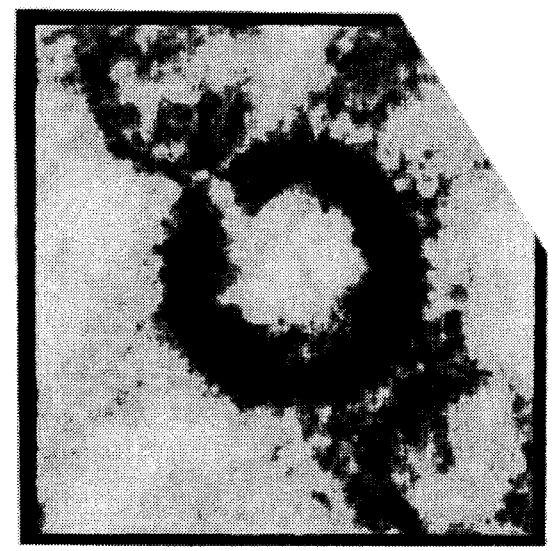
Figure 13A:
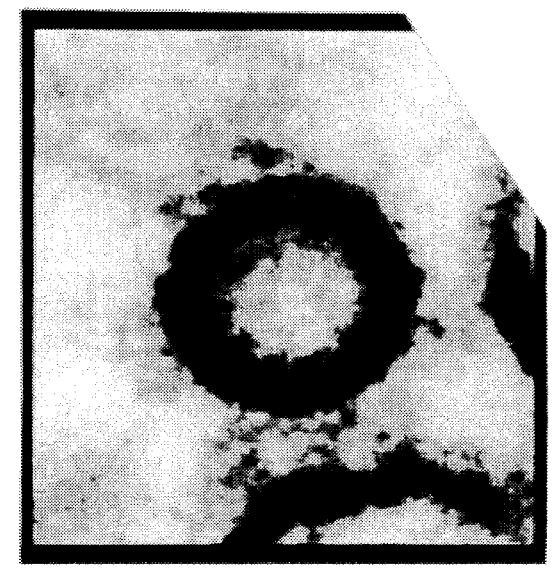
Figure 13F:
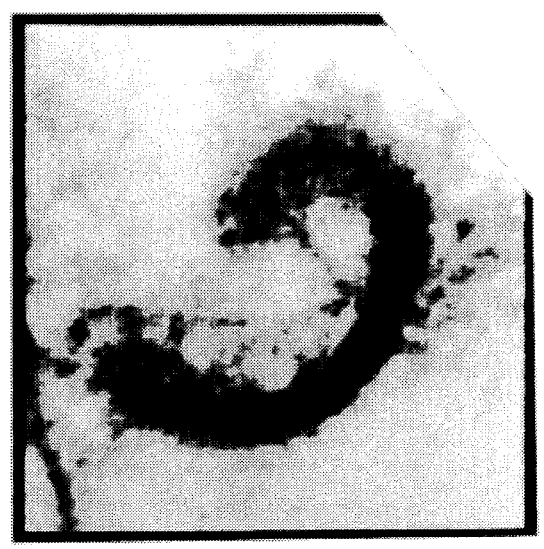
Figure 13E:
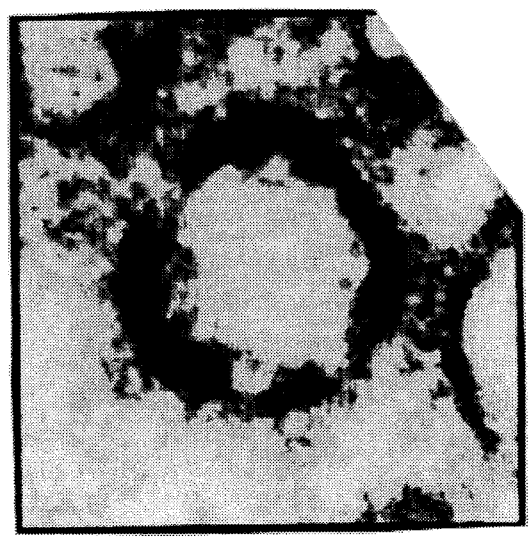
Figure 13D:
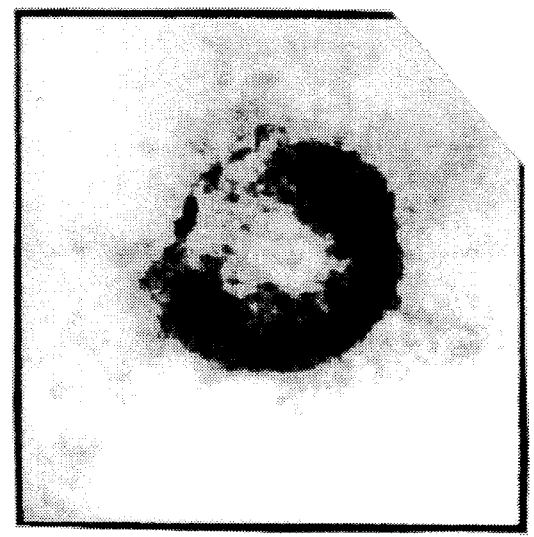

Rabbit serum alone (FIG. 11B) and monoclonal antibody NM-01 alone had no detectable effect on morphology of HIV-1. Exposure of HIV-1 to monoclonal antibody NM-01 with complement was associated with the appearance of numerous viral particles with disrupted envelopes and loss of the electron dense core (FIG. 11A). Representative preparations exhibited approximately 90% disrupted virions, the majority of which had loss of the internal core. The remaining 10% of virions were intact or had partially disrupted outer envelopes. Higher magnification revealed that disruption of HIV-1 occurred by direct lysis as illustrated in the series of micrographs of the lysis of mature and incomplete viral particles in FIGS. 12A to 12F and 13A to 13F, respectively.

Example 8

The combination of monoclonal antibody NM-01 and complement was next analyzed to determine its effect on HIV-1 infectivity.

Determination of Tissue Culture Infectivity Dose

HIV-1$_{IIIB}$-infected H9 cells were washed twice in cytotoxicity medium (Cedarlane Lab. Ltd.) and then resuspended in cytotoxicity medium containing 2 µg/ml monoclonal antibody NM-01 or control IgG$_{2b}$. After incubation at 4° C. for 2 hours, samples were aliquoted and either rabbit complement or heat-inactivated rabbit serum (Cedarlane Lab. Ltd.) was added at a dilution of 1:6. The cells were incubated at 4° C. for 20 minutes and then 37° C. for 45 minutes, washed with medium, resuspended in 50%FBS/RPMI 1640 medium and shaken. The supernatant of viral isolate was diluted 10-fold and then serially diluted 2 times before addition of 25 µl to H9 cells (1×10$^5$/25 µl). After incubation for 3 hours at 37° C., the exposed cells were diluted with 10% FBS/RPMI 1640 medium and maintained at 37° C. Viral infection was determined after 6 days by reverse transcriptase assays. The tissue culture infectivity dose for 50% of H9 cell aliquots (TCID$_{50}$) was determined by the dilution that exhibited 50% infection. Table 5 sets out the results of the experiments.

TABLE 5

| NM-01 | Complement | TCID$_{50}$ | | |
|---|---|---|---|---|
| | | Expt. 1 | Expt.2 | Expt. 3 |
| – | – | 1:2560 | 1:510 | 1:10240 |
| – | + | 1:5260 | 1:510 | 1:10240 |
| + | – | 1:320 | 1:128 | 1:1280 |
| + | + | 1:20 | 1:16 | 1:80 |

While monoclonal antibody NM-01 alone is capable of neutralizing infectivity of HIV-1$_{IIIB}$, treatment with both monoclonal antibody NM-01 and complement decreased infectivity of HIV-1 nm over 10-fold. A similar effect was also seen when human complement (in the form of human serum) was administered with monoclonal antibody NM-01. These findings indicate that exposure of HIV-1 to both monoclonal antibody NM-01 and complement is associated with a significant decrease in viral infectivity, and further support a role for monoclonal antibody NM-01 mediated complement-dependent virolysis in HIV-1 therapy. See also, Nakamura et al., *AIDS RESEARCH AND HUMAN RETROVIRUSES*, 9(7), pp. 619–626 (1993) which is incorporated by reference herein.

Example 9

The DNA sequences of the variable regions of the heavy and light chain of monoclonal antibody NM-01 were cloned by PCR using cDNA generated from hybridoma HB 10726 cytoplasmic RNA as template. The variable region DNAs were then each inserted into M13mp18/mp19 (Pharmacia, Milton Keynes, UK) and sequenced. The DNA and deduced amino acid sequences of the NM-01 heavy and light chain variable regions are set out in SEQ ID NOs: 15 and 16 and SEQ ID NOs: 17 and 18, respectively. Nucleotides 1–21 and 334–363 of SEQ ID NO: 15 correspond to the PCR primers used to amplify NM-01 light chain sequences and nucleotides 1–27 and 385–402 of SEQ ID NO: 17 correspond to the PCR primers used to amplify NM-01 heavy chain sequences. Resequencing of the variable regions of monoclonal antibody NM-01 resulted in the sequences set out in SEQ ID NOs: 19 and 20 and SEQ ID NOs: 21 and 22, which are the DNA and deduced amino acid sequence of the heavy chain variable region and the DNA and deduced amino acid sequence of the light chain variable region, respectively. The NM-01 light chain variable region (VK) amino acid sequence was determined to be the most homologous to the Kabat murine kappa subgroup III and the NM-01 heavy chain variable region (VH) amino acid sequence was determined to be a member of the Kabat murine heavy chain subgroup IA.

The first 120 residues of the amino acid sequences of the NM-01 heavy (SEQ ID NO: 20) and light chain (SEQ ID NO: 22) variable regions are also set out in FIGS. 14 and 15, respectively, wherein the boxed amino acids are the complementarity determining regions (CDRs) of the antibody which determine the binding specificity of the antibody. The CDRs identified in FIGS. 14 and 15 are shifted in relation to the CDRs indicated in the prior International Patent Application No. PCT/U.S.92/07111 to bring them in line with CDR definitions of Kabat et at., *Sequences of Proteins of Immunological Interest*, 5th Edition, U.S. Department of Health and Human Services, U.S. Government Printing Office (1991). In the FIGS. 14 and 15, each heavy or light chain amino acid sequence is compared to the corresponding amino acid sequences (SEQ ID NO: 23 and 24) of the heavy and light chain variable regions of monoclonal antibody BAT123 as reported in Liou et at., Supra, and to the corresponding amino acid sequences (SEQ ID NOs: 25 and 26) of the heavy and light chain variable regions of monoclonal antibodies F58/H3 and P4/D10 obtained from the ECACC. The variable region amino acid sequences of monoclonal antibodies F58/H3 and P4/D10 were found to be identical.

The heavy chain variable region of NM-01 differs from that of BAT-123 by forty-six amino acids out of a total of one hundred twenty. The light chain variable regions of these two antibodies differ by twenty-three amino acids. Significantly, the three CDRs in the heavy chain (V-H) of the NM-01 molecule are about 41 to 90% different in sequence from those of BAT-123, while the sequences of the three CDRs in the light chain (V-L) vary by about 29 to 47% compared to NM-01.

The heavy chain variable region of NM-01 differs from that of F58/H3 and P4/D10 by one hundred three amino acids out of a total of one hundred twenty while the light chain variable regions differ by three amino acids. The three CDRs in the heavy chain (V-H) of the NM-01 molecule are about 86 to 100% different in sequence from those of F58/H3 and P4/D10, while the sequences of the three CDRs in the light chain (V-L) vary by about 13 to 19%.

Analysis of the primary structure of NM-01 in comparison to the primary structures of BAT123, F58/H3 and P4/D10 therefore establishes that NM-01 is a novel antibody.

Example 10

Based on the DNA sequence information presented in SEQ ID NOs: 19 and 21, chimeric and humanized/reshaped versions of the NM-01 antibody were prepared. To generate a chimeric version of NM-01 the methods of Ofiandi et at., *Proc. Natl. Acad. Sci. USA*, 86, pp. 3833–3837 (1989) were employed. Humanized versions were prepared by methods similar to the CDR-grafting methods of Tempest et al., *BIO/TECHNOLOGY*, 9, pp. 266–271, (1991) and Riechmann et al., *Nature*, 322, pp. 323–327 (1988).

A. Chimeric Antibody Production

The NM-01 variable regions were cloned in two stages into mammalian expression vectors to allow production of a chimeric antibody with murine variable regions and human constant regions. First, a fully-sequenced VH or VK was amplified from the NM-01 M13mp18/mp19 clones described in Example 9 using primers specific for the 5' and 3' ends of the variable region gene and incorporating restriction sites to allow transfer of the resulting amplified fragment to the vector M13VHPCR1 or M13VKPCR1 (Orlandi et at., supra). This placed the variable region behind a promoter and signal peptide gene in the correct context for splicing onto a constant region gene. In the second stage, M13 inserts comprising sequences encoding the promoter, signal peptide and variable region (VH or VK) were excised from RF DNA and cloned into a mammalian expression vector respectively containing a human IgG 1 (vector pSV-gpt) or a kappa (vector pSV-hyg) constant region gene as appropriate.

Plasmids encoding the chimeric NM-01 light and heavy chains were then cotransfected into YB2/0 rat myeloma cells (ATCC CRL 1662) which were then selected for the presence of the xanthine guanine phosphoribosyl transferase (gpt) gene found on the heavy chain expression vector. Supernatant was screened for the presence of human IgG and cells secreting antibody were expanded. The chimeric antibody was designated NM-01 MuVH/MuVK.

B. Humanized Antibody Production

CDR-grafting was performed by site-directed mutagenesis of human variable region templates. The human variable region genes selected for CDR-grafting of the NM-01 CDRs were NEWH VH [Saul et al., *J, Biol. Chem,*, 253, pp.

585–597 (1978)] and REI VK [Epp et al., *Eur. J, Biochem.*, 45, pp. 513–524 (1974)].

In addition to the murine CDRs, the four murine amino acid residues prior to the first CDR at positions 27–30 of FIG. 16 and the murine arginine at position 73 in FIG. 16 (Kabat position 71) were included in the humanized NM-01 VH (designated HuVH). The four residues prior to the first CDR, while not hypervariable, have been shown to affect the hypervariable loop conformation by Chothia et al., *J. Mol. Biol.*, 196, pp. 901–917 (1987). The residue at Kabat position 71 has been shown to pack between the loops of CDRs 1 and 2 and to be important in determining the conformation of CDR 2 [Tramontano et al., *J. Mol., Biol.*, 215, pp. 175–182 (1990)].

Two versions of the NM-01 HuVK were made including a CDR-grafted version (HuVK) and a variant CDR-grafted (HuVKF) version having the murine phenylalanine at position 75 in FIG. 17. The side chain of the amino acid at this position has been shown to affect the conformation of CDR 1 (Chothia et al., supra) and inclusion of the murine residue has positively affected the binding ability of other humanized antibodies. See, for example, Foote et al., *J. Mol. Biol.*, 224, pp. 487–499 (1992).

The DNA and deduced amino acid sequences of the NM-01 HuVH, HuVK and HuVKF are respectively set out in SEQ ID NOs: 27 and 28; 29 and 30; and 31 and 32. The NM-01 humanized variable regions were generated from the M13 phage containing the human heavy or light chain variable region gene as follows.

M13 phage containing the human heavy or light chain variable region genes were grown in *E. coli* RZ1032 (durung) to give single-stranded template DNA containing uracil in place of thymine. One half µg template DNA was mixed with 1 pmol of an oligonucleotide which anneals to the M13 template downstream of the insert DNA. Then mutagenizing oligonucleotides encoding murine residues were annealed to the template in 20 µl of 40 mM Tris-HCl pH 7.5, 20 mM MgCl$_2$, 50 mM NaCl by heating to 80° C. for 5 minutes and cooling slowly to room temperature.

For the initial heavy chain variable region PCR reaction, the mutagenizing oligonucleotides utilized were:
VH Oligo CDR 1 (SEQ ID NO: 33)
5' CTGTCTCACC CAGTGCCAGC AATAACTACT ACTTGTGATG GAGAAGCCAG ACAC 3'
wherein the oligonucleotide is the reverse complement of DNA encoding the amino acids VSGF SITSSSYCWHWVRQ (amino acids 24–41 of SEQ ID NO: 28 and sequence HuVH in FIG. 16) and the underlined amino acids are the murine residues introduced into the template variable region sequence;
VH Oligo CDR 2 (SEQ ID NO: 34)
5' CATTGTCACT CTGCTTFrGA TGGATGGACT ATAGTCTATT
GAACCTTCAT AACATATGCG TCC(A/C)ATCCAC TCAAGA 3'
wherein the oligonucleotide is the reverse complement of DNA encoding the amino acids LEW(I/M) CIRICYEGSIDYSPSIKSRVTM (amino acids 47–71 of SEQ ID NO: 28 and sequence HuVH in FIG. 16) and the underlined amino acids are the murine residues introduced into the template variable region sequence; and
VH Oligo CDR 3 (SEQ ID NO: 35)
5' CCAGTAGTCC ATAGAGGTCG TAGTACCATG GTTT-TCTCTT
G(C/A)ACAATAAT AGAC 3'
wherein the oligonucleotide is the reverse complement of DNA encoding the amino acids VYYC(A/S) RENHGTTTSMDYW (amino acids 94–111 of SEQ ID NO: 28 and sequence HuVH in FIG. 16) and the underlined amino acids are the murine residues introduced into the template variable region sequence.

The human template utilized for the light chain variable region mutagenesis actually encoded framework regions which were related but not identical to REI and the mutagenesis reaction eliminated these discrepancies (utilizing oligonucleotides not described) as well as introducing the NM-01 CDRs. The only discrepancy to be discussed specifically herein is at position 71 of the template which encoded a phenylalanine residue not present in the REI sequence. This residue was retained in the NM-01 HuVKF (see amino acid 75 of HuVKF in FIG. 17) but was changed to the REI residue in the NM-01 HuVK (see amino acid 75 of HuVK in FIG. 17) using the oligonucleotide REI Y71 the sequence of which is set out below.
VK Oligo REI Y71 (SEQ ID NO: 36)
5' ATGGTGAAGG TGTAGTCGGT ACCGC 3'
wherein the oligonucleotide is the reverse complement of DNA encoding the amino acids GTDYTFT (amino acids 72–78 of SEQ ID NO: 32 and sequence HuVK in FIG. 17). This primer was not included in the mutagenesis reaction which generated the NM-01 HuVKF.

For both the HuVK and HuVKF light chain variable regions, the murine NM-01 CDR 1 and the template CDR 1 were identical, so alteration of CDR 1 was not required. Limited differences between the mouse and template CDRs 2 and 3 required alteration of the template CDRs 2 and 3 and the mutagenizing oligonucleotides utilized were:
VK Oligo CDR 2 (SEQ ID NO: 37)
5' AGGTTGGATG CAACGTAGAT CAGCAG 3'
wherein the oligonucleotide is the reverse complement of DNA encoding the amino acids LLIYVASN (amino acids 50–57 of SEQ ID NO: 30 and sequence HuVK in FIG. 17) and the underlined amino acids are the murine residues introduced into the template variable region sequence and
VK Oligo CDR 3 (SEQ ID NO: 38)
5' CCGAACGTGA GCGGATCTTC ATTATITFGC TGGCAGTA 3'
wherein the oligonucleotide is the reverse complement of DNA encoding the amino acids YCQQNNEDPLTF (amino acids 91–102 of SEQ ID NO: 30 and sequence HuVK in FIG. 17) and the underlined amino acids are the murine residues introduced into the template variable region sequence.

To generate the NM-01 HuVH, VH oligos CDR1, CDR2 and CDR3 were annealed to the human NEWH template. To generate the NM-01 HuVK, VK oligo REI Y71, VK oligo CDR2 and VK oligo CDR3 were annealed to the human template DNA. To generate the NM-01 HuVKF, VK oligo CDR2 and VK oligo CDR3 were annealed. Then, in the same buffer, dATP, dCTP, dGTP and dTTP were added to 250 µM final concentration, DTT was added to 7 mM, ATP was added to 1 mM, and 0.5 units T7 DNA polymer are (United States Biochemical, Cleveland, Ohio) and 0.5 units T4 DNA ligase (Life Technologies, Paisley, UK) were added. The 30 µl reaction was incubated at room temperature for 1 hour and then the DNA was ethanol precipitated. To nick the parental template strand, the DNA was dissolved in 50 µl 60 mM Tris HCl pH 8.0, 1 mM EDTA, 1 mM DTT, 0.1 mg/ml BSA containing 1 unit uracil DNA glycosylase (Boehringer Mannheim, Lewis, Sussex, UK) and incubated at 37° C. for 1 hour before NaOH was added to 0.2M and incubation was continued at room temperature for 5 minutes. The DNA was again ethanol precipitated to remove the fragmented parental DNA. The mutant DNA was then dissolved in 20 µlTE and the variable region insert was amplified by PCR using M13 forward and reverse primers. The PCR reaction mixture contained 2 µl mutant DNA, 0.5 µM of each primer, 250 µM of each dATP, dCTP, dGTP and dTTP, 10 mM Tris HCl pH 8.3, 50 mM KCl, 1.5 mM $MgCl_2$, 0.01% Tween-20, 0.01% gelatin, 0.01%NP40 and 2 units Thermalase (IBI, Cambridge, UK) in 50 μl. Amplification was achieved with 15 cycles of 94° C., 30 seconds; 50° C., 30 seconds; 72° C., 1 minute; ending with 72° C., 5 minutes. The product DNAs were cloned into M13mp19 as HindIII-BamHI fragments and representative clones were sequenced. Initially, for the heavy chain, only partial routants with murine CDRs 1 and 3 were obtained. To obtain routants with a murine CDR2, the above reactions were repeated using the partially mutated DNA as template and the VH oligo CDR2. The resulting product DNAs were cloned into M13mp19 as HindIII-BamHI fragments and representative clones were sequenced.

HindIII-BamHI fragments encoding the correct NM-01 HuVH, HuVK and HuVKF were then respectively cloned into expression vectors upstream of sequences encoding the human IgG1 (vector pSV-gpt) or the kappa (vector pSV-hyg) constant region gene as appropriate. The resulting vectors were co-electroporated into YB2/0 or NSO cells (ECACC 85110503) to generate cell lines producing fully humanized NM-01 antibody (HuVH/HuVK, produced by the YB2/0 cell line deposited as ECACC 93082022; HuVH/HuVKF, produced by the YB2/0 cell line deposited as ECACC 93082019) or were individually electroporated along with vectors encoding the appropriate chimeric NM-01 heavy or light chains described above to generate cell lines producing mix-and-match antibodies where one of the chains was chimeric (e.g., MuVH/HuVKF). Antibodies were purified by protein A agarose affinity chromatography.

Four other versions of humanized NM-01 antibody were generated by the methods described above. The first HuVHM/HuVK (produced by the YB2/0 cell line ECACC 93082020) and the second HuVHM/HuVKF (produced by the YB2/0 cell line deposited as 93082021) include a methionine at position 48 of the HuVH. The third version HuVHS/HuVK (produced by the YB2/0 cell line deposited as ECACC 93082023) and the fourth version HuVHS/HuVKF (produced by the YB2/0 cell line deposited as ECACC 93082018) include a serine at position 93 of the HuVH. These humanized antibodies had similar antigen binding properties to those of the NM-01 HuVH/HuVK antibody or the NM-01 HuVH/HuVKF antibody, depending on the light chain included. The antigen binding properties of NM-01 HuVH/HuVK and NM-01 HuVH/HuVKF are described below.

C. Chimeric and Humanized Antibody Activity

Binding of the humanized NM-01 antibodies to gp120 was evaluated in comparison to binding of murine NM-01 in a competition assay. Plates were coated with recombinant gp120 (American Biotechnologies Inc., Cambridge, Mass.)(5 ng/well) and blocked with 5% normal goat serum (Life Technologies). Dilutions (10–1000 ng/100 μl) of humanized NM-01 antibodies, chimeric NM-01 antibody, murine NM-01 antibody or a negative control humanized antibody were added per well and the plates were incubated at 37° C. for 30 minutes. Biotinylated murine NM-01 antibody (500 ng/50 μl PBS per well) was added and incubation was continued for 1 hour. The plates were washed with PBS–0.05% Tween 20. HRPO-streptavidin (Sera-Lab Limited, Crawley Down, Sussex, UK; 40 ng/100 μl PBS per well) was added and plates were incubated for 30 minutes. The plates were then washed and incubated in the presence of o-phenyldiamine for 5 minutes or until color developed. Absorbances were read at 492 nm.

Humanized NM-01 antibody HuVH/HuVK was as efficient/active as the murine NM-01 antibody in blocking the binding of labelled murine NM-01 antibody to gp120, while humanized NM-01 antibody HuVH/HuVKF was approximately four-fold more active than the murine antibody. Chimeric NM-01 antibody was less active than the murine NM-01 antibody.

The chimeric and humanized NM-01 antibodies were also evaluated for HIV-1 neutralization activity by RT, p24 and syncytium inhibition assays. The assays, performed essentially as described in the foregoing examples, were as follows.

Figure 18:
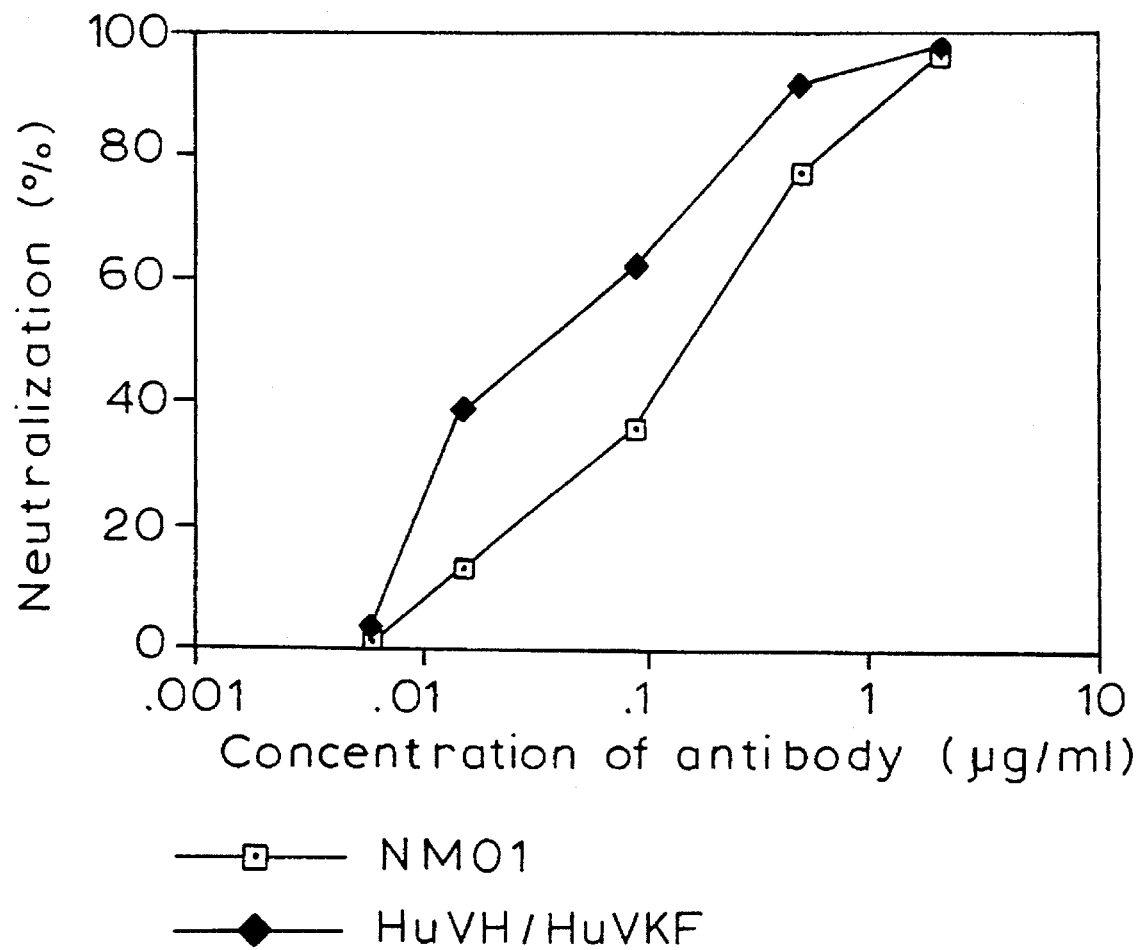
FIGS. 18, 19, 20, 21 and 22 graphically report the results of the screening by reverse transcriptase, p24, MT-2 and syncytia formation assays, respectively, of the biological activity of chimefie and humanized antibodies of the invention.
Figure 19:
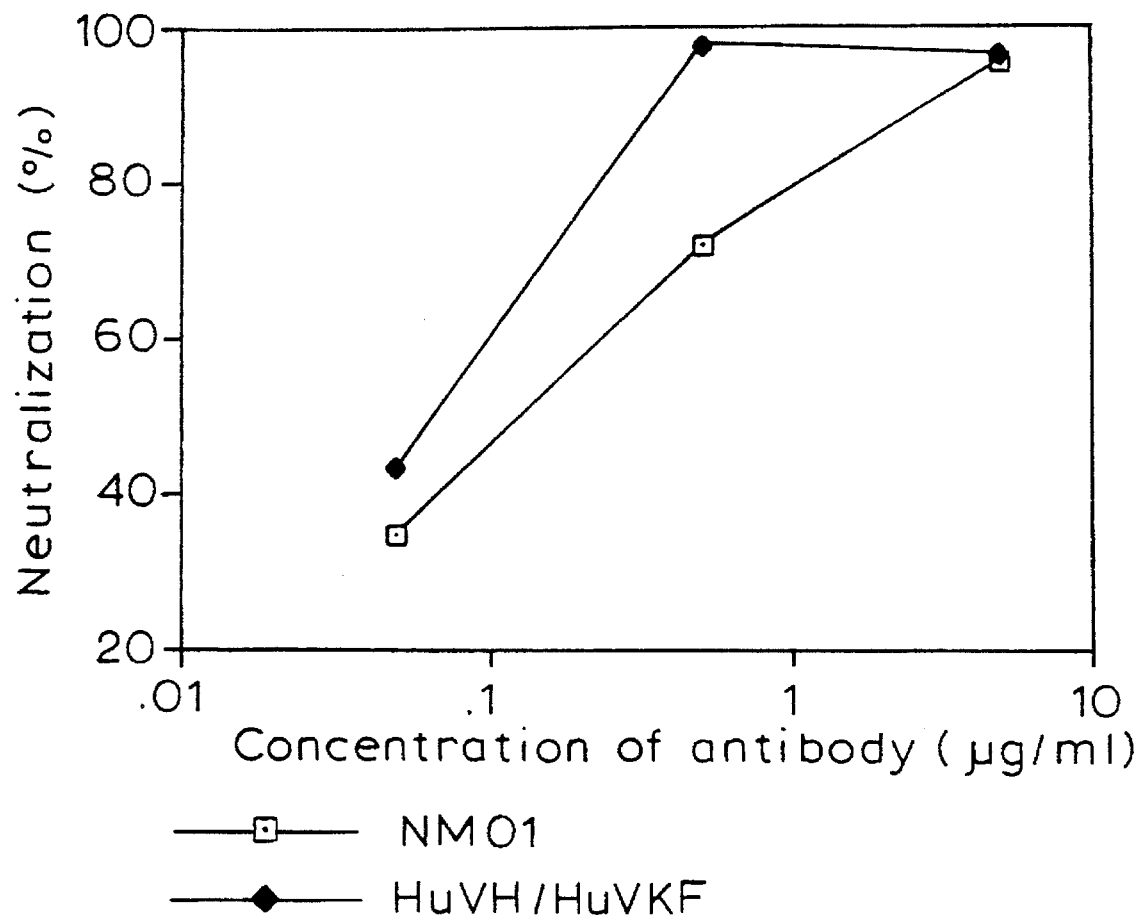

In the RT assay, antibodies were serially diluted in RPMI 1640 medium with 15% fetal bovine serum. Dilutions of the antibody were incubated with 100 tissue culture 50% infective doses ($TCID_{50}$) of MN or $III_B$ virus in 96-well plates for 2 hours at 4° C. H9 cells ($2.5 \times 10^5$ cells) were then added to each well and the plate was incubated for another 1 hour at 37° C. The H9 cell suspension was then diluted in 2 ml RPM11640 medium/15% fetal bovine serum and incubated in a 24-well plate at 37° C. Virus production was determined by RT assay on day 7. Results of the assay are presented in FIGS. 18 (MN) and 19 ($III_B$).

Figure 20:
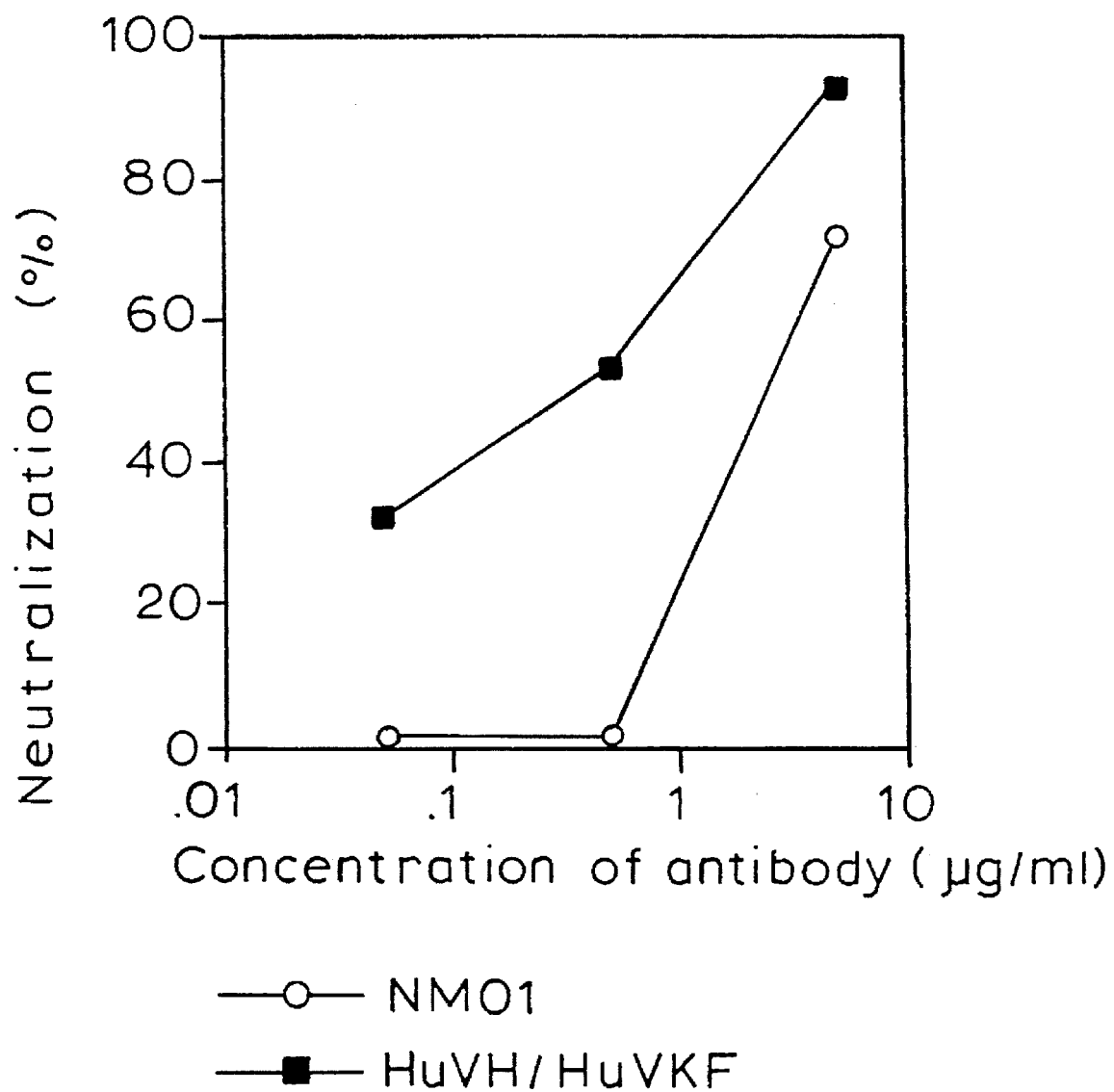
Figure 21:
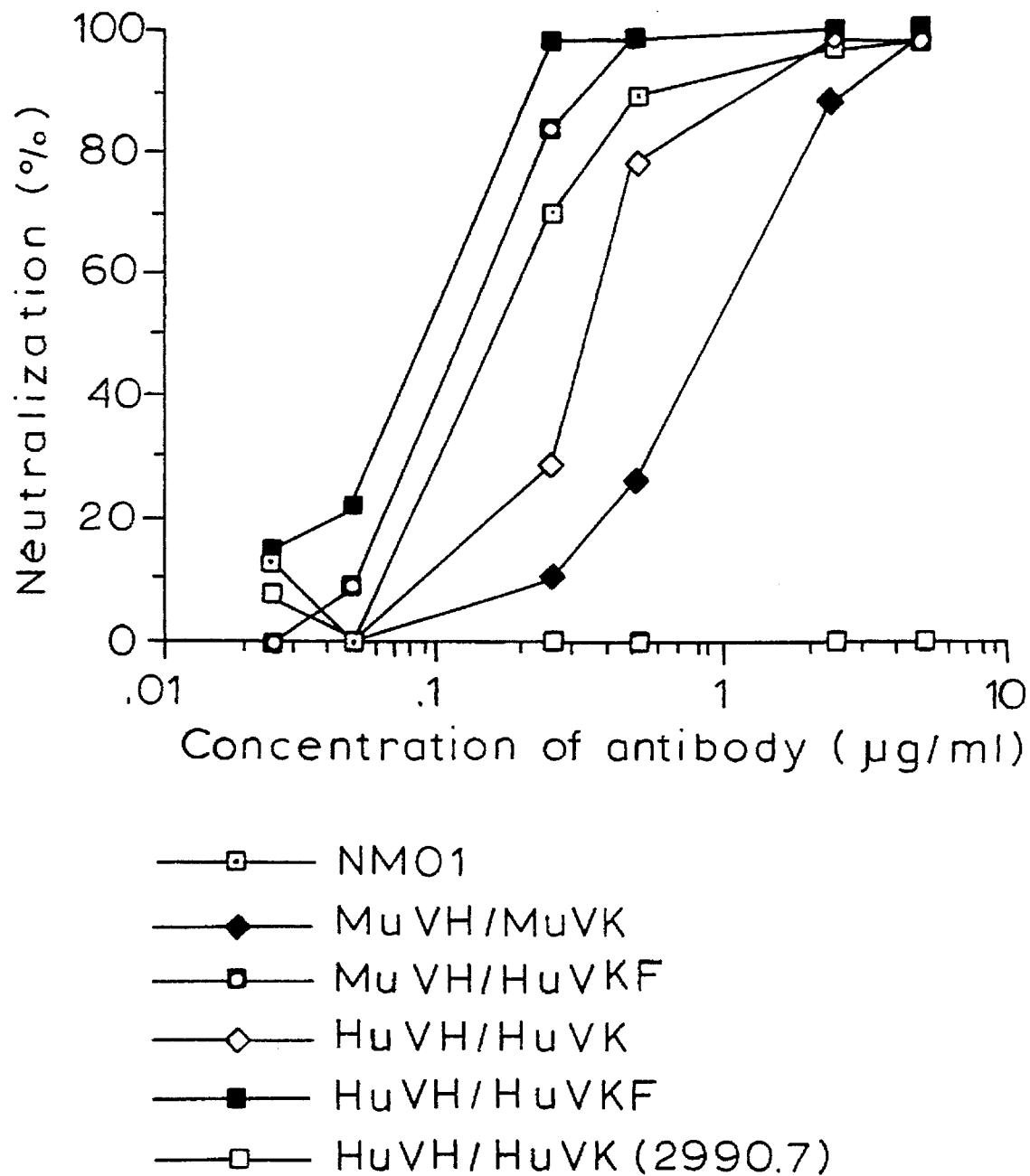

In the p24 assay, H9 cells were incubated for 6 to 8 days with the MN or $III_B$ virus ($100 \times TCID_{50}$) and monoclonal antibody. The presence of p24 antigen in the tissue culture supernatant was then quantitated by the HIV-1 p24 core profiled enzyme-linked immunosorbent assay (ELISA), using the method described by the manufacturer (Du Pont-NEN). Briefly, the antigen-antibody complex was probed with a horseradish peroxidase (HRP) conjugate. The end product was quantitated by the intensity of the yellow color, which is directly proportional to the amount of captured HIV-1 p24 core antigen. Color development was read at 450 nm, using a microplate ELISA reader and the results of the assay are presented in FIGS. 20 (MN) and 21 ($III_B$) wherein toonotional antibody 2990.7 is a negative control.

Figure 22:
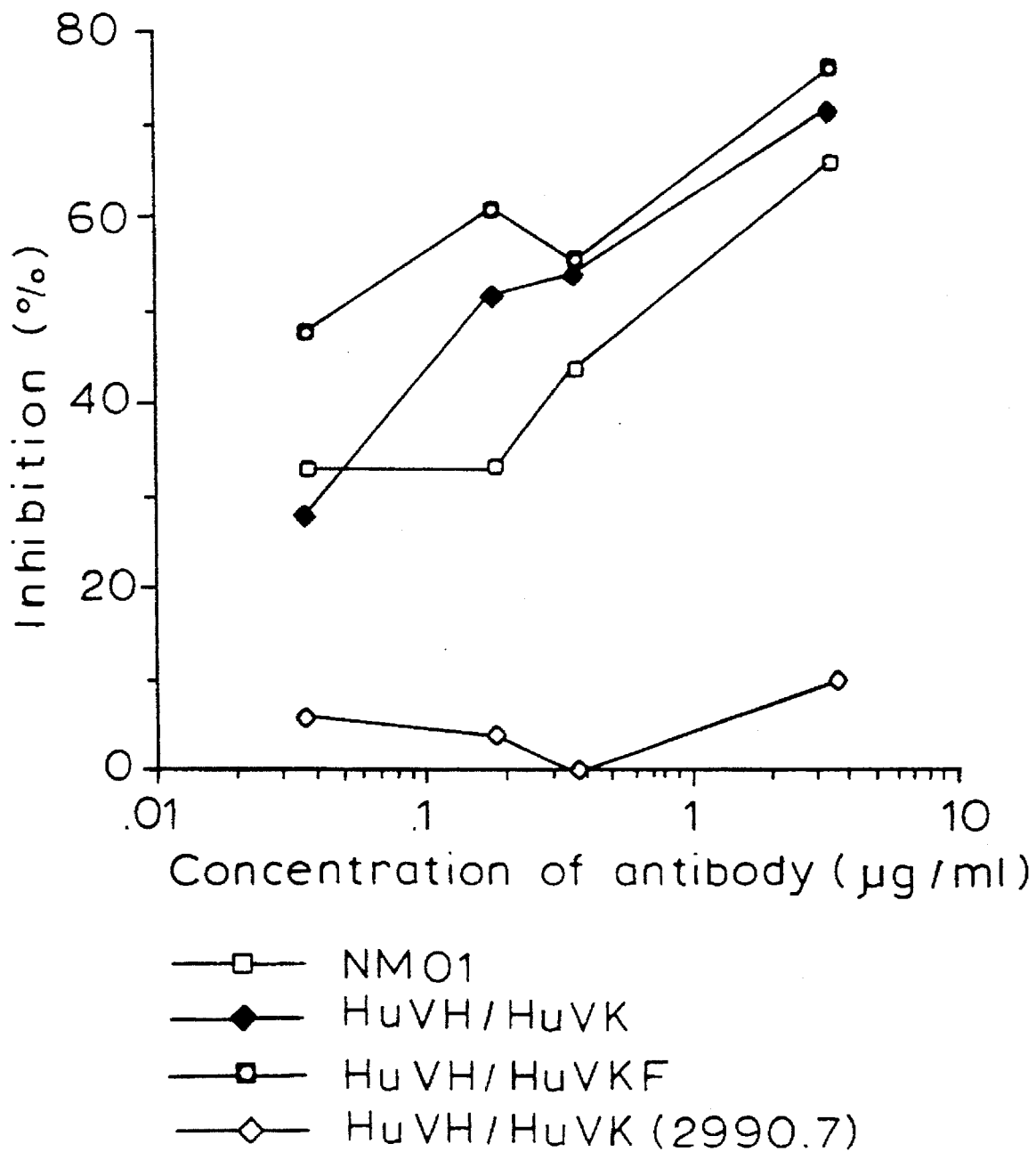

Lastly, in the syncytium assay, H9 cells chronically infected with either MN virus were incubated with dilutions of monoclonal antibody NM-01 for 1 hour at 37° C. Cells from the indicator cell line C8166 were then added ($3 \times 10^4$ cells/well) and the plate was incubated for an additional 2 to 12 hours at 37° C. Syncytium greater than three lymphocyte cell diameters were counted and compared to that obtained for control infected H9 cells in the absence of antibody. FIG. 22 presents the results of the assay wherein antibody 2990.7 is a negative control.

The results of the three assays demonstrate that the humanized NM-01 antibody HuVH/HuVKF was equally effective or more effective than murine NM-01 monoclonal antibody in neutralizing the MN and $III_B$ isolates of HIV-1.

While the present invention has been described in terms of preferred embodiments, it is understood that variations and improvements will occur to those skilled in the art. Therefore, it is intended that the appended claims cover all such equivalent variations which come within the scope of the invention as claimed.

---

I claim:

1. An NM01 monoclonal antibody characterized by the ability to specifically bind to the amino acids G-P-G-R (SEQ ID NO: 1) of HIV-1 gp120 or gp160 protein and the ability to neutralize in vitro the infection of H9 cells by live HIV-1 strains MN and III$_B$ as determined by reverse transcriptase, p24, MT-2 and syncytia formation assays, the antibody being further characterized by comprising a heavy chain variable region consisting of the amino acid sequence set out in SEQ ID NO: 20 and a light chain variable region consisting of the amino acid sequence set out in SEQ ID NO: 22.

2. An NM01 monoclonal antibody characterized by the ability to specifically bind amino acids G-P-G-R (SEQ ID. No:1) of HIV-1 gp120 or gp160 protein and the ability to neutralize in vitro infection of H9 cells by live HIV-1 strains MN and III$_B$ as determined by reverse transcriptase, p24, MT-2 and syncytia formation assays.

3. The antibody of claim 1 or claim 2 which is produced by hybridoma cell line ATCC HB 10726.

4. The antibody of claim 1 or claim 2 comprising murine NM01 variable regions and human constant regions.

5. A CDR-grafted antibody comprising the complementarity determining regions of the antibody of claim 1 or claim 2.

6. An antibody fragment which retains the antigen-binding properties of the NM01 antibody of claim 1 or claim 2, wherein said antibody fragment is selected from the group consisting of a Fab fragment and a F(ab')2 fragment.

7. A composition comprising the antibody of claim 1 or claim 2 and an acceptable carrier.

8. Hybridoma cell line ATCC HB 10726.

\* \* \* \* \*

UNITED STATES PATENT AND TRADEMARK OFFICE
CERTIFICATE OF CORRECTION

PATENT NO.     : 5,558,865
DATED          : September 24, 1996
INVENTOR(S)    : Tsuneya Ohno It is certified that error appears in the above-identified patent and that said Letters Patent is hereby corrected as shown below:

OTHER PUBLICATIONS,
Column 1, page 2,
Line 3, "Cooper" should begin a new paragraph.

Column 2, page 2,
Line 44, under Orlandi *et al.*, replace "Po;ymerase" with -- Polymerase --.

Column 2, page 3,
Line 25, under Waldmann, replace "1657, (1991)" with -- 1657-1662 (1991) --.
Line 27, replace "Hird *et al.* Genes and Cancer Carney and Sikora p. 183 ed (1990)" with -- Hird *et al., Genes & Cancer*, Carney & Sikora (eds), John Wiley & Sons, Ltd., 183-189 (1990) --.
Line 29, replace "Harris *et al.* TibTech vol. 11 p. 42 (1993)" with -- Harris & Emery, *TIBTEC*, 42-44 (Feb. 1993) --.
Line 30, replace "Morrison et al. Clin. Chem. 34/9 1668-(1988)." with -- Morrison *et al., Clin. Chem.*, 34:1668-1675 (1998) --.
Line 31, replace "Queen et al. PNAS vol. 86 p. 10029 (1989)" with -- Queen *et al., Proc. Nat'l. Acad. Sci. (USA)*, 86:10029-10033 (1989) --.

Column 1,
Line 17, replace "in vivo" with -- *in vivo* --.
Line 18, replace "Cell" with -- Cell --.
Line 46, replace "USA" with -- *USA* --.
Line 64, replace "gp 120" with -- gp120 --.

Column 2,
Line 4, replace "USA" with -- *USA* --.
Line 5, replace "USA" with -- *USA* --.
Line 6, replace "USA" with -- *USA* --.
Line 7, replace "USA" with -- *USA* --.
Line 7, replace "V3" with $V_3$ --.
Line 9, replace "V3" with $V_3$ --.
Line 15, replace "V3" with $V_3$ --.
Line 17, replace "supra" with -- supra --.
Line 19, replace "USA" with -- *USA* --.
Line 20, replace "supra" with -- supra --.
Line 22, replace "S-turn" with -- B turn --.
Line 24, replace "USA" with -- *USA* --.

UNITED STATES PATENT AND TRADEMARK OFFICE
CERTIFICATE OF CORRECTION

PATENT NO. : 5,558,865
DATED : September 24, 1996
INVENTOR(S) : Tsuneya Ohno

It is certified that error appears in the above-identified patent and that said Letters Patent is hereby corrected as shown below:

Column 3,
Line 12, replace "USA" with -- *USA* --.
Line 21, replace "J. Immunol." with -- *J. Immunol.* --.
Line 57, replace "toonotional" with -- monoclonal --.

Column 4,
Line 27, replace "hi-specific" with -- bi-specific --.
Line 33, replace "gp 120" with -- gp120 --.
Line 34, replace "gp 160" with -- gp160 --.
Line 35, replace "in vitro" with -- *in vitro* --.
Line 58, replace "Md." with -- Maryland --.
Line 67, replace "SP4OJG" with -- SP4 OJG --.

Column 5,
Line 11, replace "HIV-1$_{m-b}$" with -- HIV-1$_{IIIB}$ --.
Line 51, replace "chimefie" with -- chimeric --.

Column 6,
Line 27, replace "Godcling" with -- Godding --.
Line 42, replace "Tris-Hcl" with -- Tris-HCI --.

Column 7,
Line 10, replace "piper" with -- pipet --.
Line 12, replace "piper" with -- pipet --.
Line 24, replace "piperring" with -- pipetting --.
Line 37, replace "$1.6 \times 10^4 M$" with -- $1.6 \times 10^{-5} M$ --.

Column 8,
Line 55, replace "an Cl" with -- and --.

Column 9,
Line 60, replace "dam" with -- data --.

UNITED STATES PATENT AND TRADEMARK OFFICE
CERTIFICATE OF CORRECTION

PATENT NO. : 5,558,865
DATED : September 24, 1996
INVENTOR(S) : Tsuneya Ohno

It is certified that error appears in the above-identified patent and that said Letters Patent is hereby corrected as shown below:

Column 10,
Line 19, replace "13-mercaptoethanol" with -- β-mercaptoethanol --.
Line 31, replace "monclonal" with -- Monoclonal --.
Line 47, replace "WO91/11198" with -- 91/11198 --.
Line 50, replace "Mass." with -- MA --.
Line 51, replace "Mass." with -- MA --.

Column 11,
Line 2, replace "Calif." with -- CA --.
Line 51, replace "gp 120" with -- gp120 --.

Column 12,
Line 16, replace "Mass." with -- MA --.
Line 48, replace "gp 120" with -- gp120 --.
Line 49, replace "supra" with -- supra --.
Line 50, please delete "and III$_B$-like".
Line 53, replace "supra" with -- supra --.
Line 65, replace "P4;/D10" with -- P4/D10 --.

Column 13,
Line 26, replace "100°1" with -- 100 μl --.
Line 47, replace "monoclonal" with -- Monoclonal --.
Line 57, replace "USA" with -- *USA* --.
Line 65, replace "μ/ml" with -- μg/ml --.

Column 16,
Line 1, replace "Lysis of HIV-1" with -- *Lysis of HIV-1* --.
Line 8, replace "lowotox-MA" with -- low-tox-MA --.

Column 17,
Line 4, replace "HIV-1$_{nm}$" with -- HIV-1$_{IIIB}$ --.
Line 10, replace "NM-01 mediated" with -- NM-01-mediated --.
Line 12, replace "AIDS RESEARCH AND HUMAN RETRO VIRUSES" with -- *AIDS RESEARCH AND HUMAN RETRO VIRUSES* --.
Line 50, replace "PCT/U.S.92/07111" with -- PCT/WO92/07111 --.
Line 59, replace "supra" with -- supra --.

UNITED STATES PATENT AND TRADEMARK OFFICE
CERTIFICATE OF CORRECTION

PATENT NO.    : 5,558,865
DATED         : September 24, 1996
INVENTOR(S)   : Tsuneya Ohno It is certified that error appears in the above-identified patent and that said Letters Patent is hereby corrected as shown below:

Column 18,
Line 26, replace "Ofiandi" with -- Orlandi --.
Line 44, replace "supra" with -- supra --.
Line 50, replace "IgG 1" with -- IgG1 --.

Column 19,
Line 1, replace "Eur" with -- *Eur* --.
Line 19, replace "supra" with -- supra --.
Line 30, replace "(dur ung)" with -- (dut̄ unḡ) --.
Line 51, replace "CTGCTTFrGA" with -- CTGCTTTTGA --.
Line 57, replace 'CIRICYEGSIDYSPSIKSRVTM" WITH -- GRICYEGSIDYSPSIKSRVTM --.
Line 62, replace "5' CCAGTAGTCC ATAGAGGTCG TAGTACCATG G TITTCTCTT"
with -- 5' CCAGTAGTCC ATAGAGGTCG TAGTACCATG GTTTTCTCTT --.
Line 67, replace "RENHGTTTSMDYW" with -- RENHGTTTSMDYW --.

Column 20,
Line 36, replace 5' CCGAACGTGA GCGGATCTTC ATTATITFGC TGGAGTA 3'"
with -- 5' CCGAACGTGA GCGGATCTTC ATTATTTTGC TGGCAGTA 3'--.
Line 52, replace "polymer are" with -- polymerase --.
Line 53, replace "Ohio" with -- OH --.

Column 21,
Line 8, replace "routants" with -- mutants --.
Line 9, replace "routants" with -- mutants --.
Line 52, replace "Mass." with -- MA --.

Column 22,
Line 24, replace "1555 Fetal" with -- 15% fetal --.
Line 40, replace "toonotional" with -- monoclonal --.

UNITED STATES PATENT AND TRADEMARK OFFICE
CERTIFICATE OF CORRECTION

PATENT NO. : 5,558,865
DATED : September 24, 1996
INVENTOR(S) : Tsuneya Ohno

It is certified that error appears in the above-identified patent and that said Letters Patent is hereby corrected as shown below:

Column 49,
Line 25, replace "in vitro" with -- *in vitro* --.
Line 27, replace "P24." with -- P24, --.
Line 30, replace "SEO" with -- SEQ --.
Line 36, replace "in vitro" with -- *in vitro* --.

Signed and Sealed this

Twentieth Day of November, 2001

Attest:

NICHOLAS P. GODICI
Attesting Officer    Acting Director of the United States Patent and Trademark Office

SEQUENCE LISTING ( 1 ) GENERAL INFORMATION:

( i i i ) NUMBER OF SEQUENCES: 38

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

Gly Pro Gly Arg
  1

( 2 ) INFORMATION FOR SEQ ID NO:2:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

Cys Thr Arg Pro Asn Trp Asn Lys Arg Lys Arg Ile His Ile Gly
  1              5                    10                  15

( 2 ) INFORMATION FOR SEQ ID NO:3:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

Arg Ile His Ile Gly Pro Gly Arg Ala Phe Tyr Thr Thr Lys Asn
  1              5                    10                  15

( 2 ) INFORMATION FOR SEQ ID NO:4:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

Tyr Thr Thr Lys Asn Ile Ile Gly Thr Ile Arg Gln Ala His Cys
  1              5                    10                  15

( 2 ) INFORMATION FOR SEQ ID NO:5:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

Arg Ile His Ile Gly Pro Gly Arg Ala Phe Tyr Thr Thr Lys Asn
  1              5                    10                  15

( 2 ) INFORMATION FOR SEQ ID NO:6:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

```
Ile Arg Ile Gly Pro Gly Arg Ala Phe Val Thr Ile Gly Lys
1               5                   10
```

( 2 ) INFORMATION FOR SEQ ID NO:7:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

```
Cys Asn Thr Arg Lys Ser Ile Lys Gly Pro Gly Arg Val Ile Tyr Ala
1               5                   10                  15
Thr Gly Gln
```

( 2 ) INFORMATION FOR SEQ ID NO:8:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

```
Cys His Thr Arg Lys Arg Val Thr Leu Gly Pro Gly Arg Val Trp Tyr
1               5                   10                  15
Thr Thr Gly Glu
                20
```

( 2 ) INFORMATION FOR SEQ ID NO:9:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

```
Cys Asn Thr Lys Lys Gly Ile Ala Ile Gly Pro Gly Arg Thr Leu Tyr
1               5                   10                  15
Ala Arg Glu Lys
                20
```

( 2 ) INFORMATION FOR SEQ ID NO:10:

( i ) SEQUENCE CHARACTERISTICS:
        ( A ) LENGTH: 23 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:10:

```
Cys Asn Thr Arg Gln Ser Thr Pro Ile Gly Leu Gly Gln Ala Leu Tyr
1               5                   10                  15
```

```
         Thr Thr Arg Gly Arg Thr Lys
                     20
```

( 2 ) INFORMATION FOR SEQ ID NO:11:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:11:

```
Cys Asn Ile Arg Gln Arg Thr Ser Ile Gly Leu Gly Gln Ala Leu Tyr
1               5                   10                  15

Thr Thr Lys Thr Arg Ser
            20
```

( 2 ) INFORMATION FOR SEQ ID NO:12:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:12:

```
Cys Asn Thr Arg Gln Arg Thr Pro Ile Gly Leu Gly Gln Ser Leu Tyr
1               5                   10                  15

Thr Thr Arg Ser Arg Ser
            20
```

( 2 ) INFORMATION FOR SEQ ID NO:13:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:13:

```
Arg Ile Thr Lys Gly Pro Gly Arg Val Ile Val Ala Thr Gly Gln
1               5                   10                  15
```

( 2 ) INFORMATION FOR SEQ ID NO:14:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:14:

```
Cys Asn Thr Arg Lys Ser Ile Thr Lys Gly Pro Gly Arg Val Ile Tyr
1               5                   10                  15

Ala Thr Gly Gln
            20
```

( 2 ) INFORMATION FOR SEQ ID NO:15:

( i ) SEQUENCE CHARACTERISTICS:
        ( A ) LENGTH: 402 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
    ( A ) NAME/KEY: CDS
    ( B ) LOCATION: 1..402

( x i ) SEQUENCE DESCRIPTION: SEQ ID NO:15:

| | | | | | | | | | | | | | | | | |
|---|---|---|---|---|---|---|---|---|---|---|---|---|---|---|---|---|
| GAG | GTC | CAG | CTG | CAG | GAG | TCT | GGA | CCT | GCT | GTC | ATC | AAG | CCA | TCA | CAG | 48 |
| Glu | Val | Gln | Leu | Gln | Glu | Ser | Gly | Pro | Ala | Val | Ile | Lys | Pro | Ser | Gln | |
| 1 | | | | 5 | | | | | 10 | | | | | 15 | | |
| TCA | CTG | TCT | CTC | ACC | TGC | ATA | GTC | TCT | GGA | TTC | TCC | ATC | ACA | AGT | AGT | 96 |
| Ser | Leu | Ser | Leu | Thr | Cys | Ile | Val | Ser | Gly | Phe | Ser | Ile | Thr | Ser | Ser | |
| | | | 20 | | | | | 25 | | | | | 30 | | | |
| AGT | TAT | TGC | TGG | CAC | TGG | ATC | CGC | CAG | CCC | CCA | GGA | AAG | GGG | TTA | GAG | 144 |
| Ser | Tyr | Cys | Trp | His | Trp | Ile | Arg | Gln | Pro | Pro | Gly | Lys | Gly | Leu | Glu | |
| | | 35 | | | | | 40 | | | | | 45 | | | | |
| TGG | ATG | GGG | CGC | ATA | TGT | TAT | GAA | GGT | TCA | ATA | GAC | TAT | AGT | CCA | TCC | 192 |
| Trp | Met | Gly | Arg | Ile | Cys | Tyr | Glu | Gly | Ser | Ile | Asp | Tyr | Ser | Pro | Ser | |
| | 50 | | | | | 55 | | | | | 60 | | | | | |
| ATC | AAA | AGC | CGC | AGC | ACC | ATC | TCC | AGA | GAC | ACA | TCT | CTG | AAC | AGA | TTC | 240 |
| Ile | Lys | Ser | Arg | Ser | Thr | Ile | Ser | Arg | Asp | Thr | Ser | Leu | Asn | Arg | Phe | |
| 65 | | | | | 70 | | | | | 75 | | | | | 80 | |
| TTT | ATC | CAG | CTG | AGT | TCT | GTG | ACA | AAT | GAG | GAC | ACT | GCC | ATG | TAT | TAC | 288 |
| Phe | Ile | Gln | Leu | Ser | Ser | Val | Thr | Asn | Glu | Asp | Thr | Ala | Met | Tyr | Tyr | |
| | | | | 85 | | | | | 90 | | | | | 95 | | |
| TGT | TCC | AGG | GAA | AAC | CAT | GGT | ACT | ACG | ACC | TCT | ATG | GAC | TAC | TGG | GGT | 336 |
| Cys | Ser | Arg | Glu | Asn | His | Gly | Thr | Thr | Thr | Ser | Met | Asp | Tyr | Trp | Gly | |
| | | | 100 | | | | | 105 | | | | | 110 | | | |
| CAA | GGA | ACC | TCA | GTC | ACC | GTC | TCC | TCA | GCC | AAA | ACA | ACA | CCC | CCA | TCA | 384 |
| Gln | Gly | Thr | Ser | Val | Thr | Val | Ser | Ser | Ala | Lys | Thr | Thr | Pro | Pro | Ser | |
| | | 115 | | | | | 120 | | | | | 125 | | | | |
| GTC | TAT | CCA | CTG | GAA | CCT | | | | | | | | | | | 402 |
| Val | Tyr | Pro | Leu | Glu | Pro | | | | | | | | | | | |
| 130 | | | | | | | | | | | | | | | | |

( 2 ) INFORMATION FOR SEQ ID NO:16:

( i ) SEQUENCE CHARACTERISTICS:
        ( A ) LENGTH: 134 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

| | | | | | | | | | | | | | | |
|---|---|---|---|---|---|---|---|---|---|---|---|---|---|---|
| Glu | Val | Gln | Leu | Gln | Glu | Ser | Gly | Pro | Ala | Val | Ile | Lys | Pro | Ser | Gln |
| 1 | | | | 5 | | | | | 10 | | | | | 15 | |
| Ser | Leu | Ser | Leu | Thr | Cys | Ile | Val | Ser | Gly | Phe | Ser | Ile | Thr | Ser | Ser |
| | | | 20 | | | | | 25 | | | | | 30 | | |
| Ser | Tyr | Cys | Trp | His | Trp | Ile | Arg | Gln | Pro | Pro | Gly | Lys | Gly | Leu | Glu |
| | | 35 | | | | | 40 | | | | | 45 | | | |
| Trp | Met | Gly | Arg | Ile | Cys | Tyr | Glu | Gly | Ser | Ile | Asp | Tyr | Ser | Pro | Ser |
| | 50 | | | | | 55 | | | | | 60 | | | | |
| Ile | Lys | Ser | Arg | Ser | Thr | Ile | Ser | Arg | Asp | Thr | Ser | Leu | Asn | Arg | Phe |
| 65 | | | | | 70 | | | | | 75 | | | | | 80 |
| Phe | Ile | Gln | Leu | Ser | Ser | Val | Thr | Asn | Glu | Asp | Thr | Ala | Met | Tyr | Tyr |
| | | | | 85 | | | | | 90 | | | | | 95 | |
| Cys | Ser | Arg | Glu | Asn | His | Gly | Thr | Thr | Thr | Ser | Met | Asp | Tyr | Trp | Gly |
| | | | 100 | | | | | 105 | | | | | 110 | | |
| Gln | Gly | Thr | Ser | Val | Thr | Val | Ser | Ser | Ala | Lys | Thr | Thr | Pro | Pro | Ser |
| | | 115 | | | | | 120 | | | | | 125 | | | |
| Val | Tyr | Pro | Leu | Glu | Pro | | | | | | | | | | |
| 130 | | | | | | | | | | | | | | | |

( 2 ) INFORMATION FOR SEQ ID NO:17:

( i ) SEQUENCE CHARACTERISTICS:
        ( A ) LENGTH: 363 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: CDS
        ( B ) LOCATION: 1..363

( x i ) SEQUENCE DESCRIPTION: SEQ ID NO:17:

```
GAC  ATT  GTG  CTG  ACC  CAA  TCT  CCA  GCT  TCT  TTG  GCT  GTG  TCT  CTA  GGG       48
Asp  Ile  Val  Leu  Thr  Gln  Ser  Pro  Ala  Ser  Leu  Ala  Val  Ser  Leu  Gly
 1                   5                        10                       15

CAG  AGG  GCC  ACC  ATA  TCC  TGC  AGA  GCC  AGT  GAA  AGT  GTT  GAT  AGT  TAT       96
Gln  Arg  Ala  Thr  Ile  Ser  Cys  Arg  Ala  Ser  Glu  Ser  Val  Asp  Ser  Tyr
                20                       25                       30

GGC  AAT  AGT  TTT  ATG  CAC  TGG  TAC  CAG  CAG  AAA  CCA  GGA  CAG  TCA  CCC      144
Gly  Asn  Ser  Phe  Met  His  Trp  Tyr  Gln  Gln  Lys  Pro  Gly  Gln  Ser  Pro
           35                       40                       45

AAA  CTC  CTC  ATC  TAT  GTT  GCA  TCC  AAC  CTA  GAA  TCT  GGG  GTC  CCT  GCC      192
Lys  Leu  Leu  Ile  Tyr  Val  Ala  Ser  Asn  Leu  Glu  Ser  Gly  Val  Pro  Ala
      50                       55                       60

AGG  TTC  AGT  GGC  AGT  GGG  TCT  AGG  ACA  GAC  TTC  ACC  CTC  ACC  ATT  GAT      240
Arg  Phe  Ser  Gly  Ser  Gly  Ser  Arg  Thr  Asp  Phe  Thr  Leu  Thr  Ile  Asp
 65                       70                       75                       80

CCT  GTG  GAG  GCT  GAT  GAT  GCT  GCA  ACC  TAT  TAC  TGT  CAG  CAA  AAT  AAT      288
Pro  Val  Glu  Ala  Asp  Asp  Ala  Ala  Thr  Tyr  Tyr  Cys  Gln  Gln  Asn  Asn
                     85                       90                       95

GAG  GAT  CCG  CTC  GCG  TTC  GGT  ACT  GGG  ACC  AAG  CTG  GAG  CTG  AAA  CGG      336
Glu  Asp  Pro  Leu  Ala  Phe  Gly  Thr  Gly  Thr  Lys  Leu  Glu  Leu  Lys  Arg
               100                      105                      110

GCT  GAT  GCT  GCA  CCA  ACT  GTA  TCC  ATC                                          363
Ala  Asp  Ala  Ala  Pro  Thr  Val  Ser  Ile
          115                      120
```

( 2 ) INFORMATION FOR SEQ ID NO:18:

( i ) SEQUENCE CHARACTERISTICS:
        ( A ) LENGTH: 121 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

```
Asp  Ile  Val  Leu  Thr  Gln  Ser  Pro  Ala  Ser  Leu  Ala  Val  Ser  Leu  Gly
 1                   5                        10                       15

Gln  Arg  Ala  Thr  Ile  Ser  Cys  Arg  Ala  Ser  Glu  Ser  Val  Asp  Ser  Tyr
                20                       25                       30

Gly  Asn  Ser  Phe  Met  His  Trp  Tyr  Gln  Gln  Lys  Pro  Gly  Gln  Ser  Pro
           35                       40                       45

Lys  Leu  Leu  Ile  Tyr  Val  Ala  Ser  Asn  Leu  Glu  Ser  Gly  Val  Pro  Ala
      50                       55                       60

Arg  Phe  Ser  Gly  Ser  Gly  Ser  Arg  Thr  Asp  Phe  Thr  Leu  Thr  Ile  Asp
 65                       70                       75                       80

Pro  Val  Glu  Ala  Asp  Asp  Ala  Ala  Thr  Tyr  Tyr  Cys  Gln  Gln  Asn  Asn
                     85                       90                       95

Glu  Asp  Pro  Leu  Ala  Phe  Gly  Thr  Gly  Thr  Lys  Leu  Glu  Leu  Lys  Arg
               100                      105                      110

Ala  Asp  Ala  Ala  Pro  Thr  Val  Ser  Ile
          115                      120
```

(2) INFORMATION FOR SEQ ID NO:19:

(i) SEQUENCE CHARACTERISTICS:
        (A) LENGTH: 363 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 1..363

(xi) SEQUENCE DESCRIPTION: SEQ ID NO:19:

```
CAG ATT CAG CTT AAG GAG TCT GGA CCT GCT GTC ATC AAG CCA TCA CAG      48
Gln Ile Gln Leu Lys Glu Ser Gly Pro Ala Val Ile Lys Pro Ser Gln
  1               5                  10                  15

TCA CTG TCT CTC ACC TGC ATA GTC TCT GGA TTC TCC ATC ACA AGT AGT      96
Ser Leu Ser Leu Thr Cys Ile Val Ser Gly Phe Ser Ile Thr Ser Ser
                 20                  25                  30

AGT TAT TGC TGG CAC TGG ATC CGC CAG CCC CCA GGA AAG GGT TTA GAG     144
Ser Tyr Cys Trp His Trp Ile Arg Gln Pro Pro Gly Lys Gly Leu Glu
             35                  40                  45

TGG ATG GGG CGC ATA TGT TAT GAA GGT TCA ATA GAC TAT AGT CCA TCC     192
Trp Met Gly Arg Ile Cys Tyr Glu Gly Ser Ile Asp Tyr Ser Pro Ser
 50                  55                  60

ATC AAA AGC CGC AGC ACC ATC TCC AGA GAC ACA TCT CTG AAC AGA TTC     240
Ile Lys Ser Arg Ser Thr Ile Ser Arg Asp Thr Ser Leu Asn Arg Phe
 65                  70                  75                  80

TTT ATC CAG CTG AGT TCT GTG ACA AAT GAG GAC ACT GCC ATG TAT TAC     288
Phe Ile Gln Leu Ser Ser Val Thr Asn Glu Asp Thr Ala Met Tyr Tyr
                     85                  90                  95

TGT TCC AGG GAA AAC CAT GGT ACT ACG ACC TCT ATG GAC TAC TGG GGT     336
Cys Ser Arg Glu Asn His Gly Thr Thr Thr Ser Met Asp Tyr Trp Gly
                100                 105                 110

CAA GGA ACC TCA GTC ACC GTC TCC TCA                                 363
Gln Gly Thr Ser Val Thr Val Ser Ser
            115                 120
```

(2) INFORMATION FOR SEQ ID NO:20:

(i) SEQUENCE CHARACTERISTICS:
        (A) LENGTH: 121 amino acids
        (B) TYPE: amino acid
        (D) TOPOLOGY: linear (ii) MOLECULE TYPE: protein (xi) SEQUENCE DESCRIPTION: SEQ ID NO:20:

```
Gln Ile Gln Leu Lys Glu Ser Gly Pro Ala Val Ile Lys Pro Ser Gln
  1               5                  10                  15

Ser Leu Ser Leu Thr Cys Ile Val Ser Gly Phe Ser Ile Thr Ser Ser
                 20                  25                  30

Ser Tyr Cys Trp His Trp Ile Arg Gln Pro Pro Gly Lys Gly Leu Glu
             35                  40                  45

Trp Met Gly Arg Ile Cys Tyr Glu Gly Ser Ile Asp Tyr Ser Pro Ser
 50                  55                  60

Ile Lys Ser Arg Ser Thr Ile Ser Arg Asp Thr Ser Leu Asn Arg Phe
 65                  70                  75                  80

Phe Ile Gln Leu Ser Ser Val Thr Asn Glu Asp Thr Ala Met Tyr Tyr
                     85                  90                  95

Cys Ser Arg Glu Asn His Gly Thr Thr Thr Ser Met Asp Tyr Trp Gly
                100                 105                 110
```

Gln Gly Thr Ser Val Thr Val Ser Ser
     115             120

(2) INFORMATION FOR SEQ ID NO:21:

(i) SEQUENCE CHARACTERISTICS:
        (A) LENGTH: 363 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 1..363

(xi) SEQUENCE DESCRIPTION: SEQ ID NO:21:

```
GAC ATT GTG CTG ACC CAA TCT CCA GCT TCT TTG GCT GTG TCT CTA GGG        48
Asp Ile Val Leu Thr Gln Ser Pro Ala Ser Leu Ala Val Ser Leu Gly
 1               5                  10                  15

CAG AGG GCC ACC ATA TCC TGC AGA GCC AGT GAA AGT GTT GAT AGT TAT        96
Gln Arg Ala Thr Ile Ser Cys Arg Ala Ser Glu Ser Val Asp Ser Tyr
             20                  25                  30

GGC AAT AGT TTT ATG CAC TGG TAC CAG CAG AAA CCA GGA CAG TCA CCC       144
Gly Asn Ser Phe Met His Trp Tyr Gln Gln Lys Pro Gly Gln Ser Pro
         35                  40                  45

AAA CTC CTC ATC TAT GTT GCA TCC AAC CTA GAA TCT GGG GTC CCT GCC       192
Lys Leu Leu Ile Tyr Val Ala Ser Asn Leu Glu Ser Gly Val Pro Ala
     50                  55                  60

AGG TTC AGT GGC AGT GGG TCT AGG ACA GAC TTC ACC CTC ACC ATT GAT       240
Arg Phe Ser Gly Ser Gly Ser Arg Thr Asp Phe Thr Leu Thr Ile Asp
 65                  70                  75                  80

CCT GTG GAG GCT GAT GAT GCT GCA ACC TAT TAC TGT CAG CAA AAT AAT       288
Pro Val Glu Ala Asp Asp Ala Ala Thr Tyr Tyr Cys Gln Gln Asn Asn
                 85                  90                  95

GAG GAT CCG CTC ACG TTC GGT GCT GGG ACC AAG CTG GAG CTG AAA CGG       336
Glu Asp Pro Leu Thr Phe Gly Ala Gly Thr Lys Leu Glu Leu Lys Arg
             100                 105                 110

GCT GAT GCT GCA CCA ACT GTA TCC ATC                                   363
Ala Asp Ala Ala Pro Thr Val Ser Ile
             115                 120
```

(2) INFORMATION FOR SEQ ID NO:22:

(i) SEQUENCE CHARACTERISTICS:
        (A) LENGTH: 121 amino acids
        (B) TYPE: amino acid
        (D) TOPOLOGY: linear (ii) MOLECULE TYPE: protein (xi) SEQUENCE DESCRIPTION: SEQ ID NO:22:

```
Asp Ile Val Leu Thr Gln Ser Pro Ala Ser Leu Ala Val Ser Leu Gly
 1               5                  10                  15

Gln Arg Ala Thr Ile Ser Cys Arg Ala Ser Glu Ser Val Asp Ser Tyr
             20                  25                  30

Gly Asn Ser Phe Met His Trp Tyr Gln Gln Lys Pro Gly Gln Ser Pro
         35                  40                  45

Lys Leu Leu Ile Tyr Val Ala Ser Asn Leu Glu Ser Gly Val Pro Ala
     50                  55                  60

Arg Phe Ser Gly Ser Gly Ser Arg Thr Asp Phe Thr Leu Thr Ile Asp
 65                  70                  75                  80

Pro Val Glu Ala Asp Asp Ala Ala Thr Tyr Tyr Cys Gln Gln Asn Asn
                 85                  90                  95

Glu Asp Pro Leu Thr Phe Gly Ala Gly Thr Lys Leu Glu Leu Lys Arg
```

Ala Asp Ala Ala Pro Thr Val Ser Ile
            115                 120

( 2 ) INFORMATION FOR SEQ ID NO:23:

( i ) SEQUENCE CHARACTERISTICS:
        ( A ) LENGTH: 114 amino acids
        ( B ) TYPE: amino acid
        ( D ) TOPOLOGY: linear ( i i ) MOLECULE TYPE: protein ( x i ) SEQUENCE DESCRIPTION: SEQ ID NO:23:

Glu Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
            35                  40                  45

Met Gly Tyr Ile Ser Tyr Ser Gly Ser Thr Thr Tyr Asn Pro Ser Leu
    50                  55                  60

Lys Ser Arg Ile Ser Ile Thr Arg Asp Thr Ser Lys Asn Leu Phe Phe
65                  70                  75                  80

Leu Gln Leu Ser Ser Val Thr Ser Glu Asp Thr Ala Thr Tyr Tyr Cys
                85                  90                  95

Ala Arg Gly Ser Phe Gly Asp Trp Gly Gln Gly Thr Leu Val Thr Val
            100                 105                 110

Ser Ala ( 2 ) INFORMATION FOR SEQ ID NO:24:

( i ) SEQUENCE CHARACTERISTICS:
        ( A ) LENGTH: 120 amino acids
        ( B ) TYPE: amino acid
        ( D ) TOPOLOGY: linear ( i i ) MOLECULE TYPE: protein ( x i ) SEQUENCE DESCRIPTION: SEQ ID NO:24:

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
            35                  40                  45

Lys Leu Leu Ile Tyr Ala Ala Ser Asn Val Glu Ser Gly Ile Pro Ala
    50                  55                  60

Arg Phe Tyr Gly Ser Gly Ser Gly Thr Asp Phe Thr Asn Thr Ile His
65                  70                  75                  80

Pro Val Glu Glu Glu Asp Ala Ala Thr Tyr Tyr Cys Gln Gln Ser Ile
                85                  90                  95

Asp Asp Pro Ser Thr Phe Gly Gly Gly Thr Lys Leu Glu Ile Asp Arg
            100                 105                 110

Ala Asp Ala Ala Pro Thr Val Ser
            115                 120

( 2 ) INFORMATION FOR SEQ ID NO:25:

( i ) SEQUENCE CHARACTERISTICS:
        ( A ) LENGTH: 120 amino acids
        ( B ) TYPE: amino acid
        ( D ) TOPOLOGY: linear ( i i ) MOLECULE TYPE: protein ( x i ) SEQUENCE DESCRIPTION: SEQ ID NO:25:

| Gln | Ile | Gln | Leu | Gln | Gln | Ser | Gly | Ala | Glu | Leu | Ala | Ser | Pro | Gly | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Val | Thr | Leu | Ser | Cys | Lys | Ala | Ser | Gly | Tyr | Thr | Phe | Thr | Asp | His |
|     |     |     | 20  |     |     |     |     | 25  |     |     |     |     | 30  |     |     |

| Ile | Met | Asn | Trp | Val | Lys | Lys | Arg | Pro | Gly | Gln | Gly | Leu | Glu | Trp | Ile |
|     |     | 35  |     |     |     |     | 40  |     |     |     |     | 45  |     |     |     |

| Gly | Arg | Ile | Phe | Pro | Val | Ser | Gly | Glu | Thr | Asn | Tyr | Asn | Gln | Lys | Phe |
|     | 50  |     |     |     |     | 55  |     |     |     |     | 60  |     |     |     |     |

| Met | Gly | Lys | Ala | Thr | Phe | Ser | Val | Asp | Arg | Ser | Ser | Thr | Val | Ser |
| 65  |     |     |     |     | 70  |     |     |     |     | 75  |     |     |     | 80  |

| Met | Val | Leu | Asn | Ser | Leu | Thr | Ser | Glu | Asp | Pro | Ala | Val | Tyr | Tyr | Cys |
|     |     |     |     | 85  |     |     |     |     | 90  |     |     |     |     | 95  |     |

| Asp | Leu | Ile | Tyr | Tyr | Asp | Tyr | Glu | Glu | Asp | Tyr | Tyr | Phe | Asp | Tyr | Trp |
|     |     |     | 100 |     |     |     |     | 105 |     |     |     |     | 110 |     |     |

| Gly | Gln | Gly | Thr | Thr | Leu | Thr | Val |
|     |     | 115 |     |     |     |     | 120 |

( 2 ) INFORMATION FOR SEQ ID NO:26:

( i ) SEQUENCE CHARACTERISTICS:
        ( A ) LENGTH: 120 amino acids
        ( B ) TYPE: amino acid
        ( D ) TOPOLOGY: linear ( i i ) MOLECULE TYPE: protein ( x i ) SEQUENCE DESCRIPTION: SEQ ID NO:26:

| Asp | Ile | Val | Leu | Thr | Gln | Ser | Pro | Ala | Ser | Leu | Ala | Val | Ser | Leu | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Gln | Arg | Ala | Thr | Ile | Ser | Cys | Arg | Ala | Ser | Glu | Ser | Val | Asp | Asp | Tyr |
|     |     |     | 20  |     |     |     |     | 25  |     |     |     |     | 30  |     |     |

| Gly | Ile | Ser | Phe | Met | His | Trp | Tyr | Gln | Gln | Lys | Leu | Gly | Gln | Pro | Pro |
|     |     | 35  |     |     |     |     | 40  |     |     |     |     | 45  |     |     |     |

| Lys | Leu | Leu | Ile | Tyr | Arg | Ala | Ser | Asn | Leu | Glu | Ser | Gly | Ile | Pro | Ala |
|     | 50  |     |     |     |     | 55  |     |     |     |     | 60  |     |     |     |     |

| Arg | Phe | Ser | Gly | Ser | Gly | Ser | Gly | Thr | Glu | Phe | Thr | Leu | Thr | Ile | Asn |
| 65  |     |     |     |     | 70  |     |     |     |     | 75  |     |     |     |     | 80  |

| Pro | Val | Glu | Thr | Asp | Asp | Val | Ala | Thr | Tyr | Tyr | Cys | Gln | Gln | Ser | Asn |
|     |     |     |     | 85  |     |     |     |     | 90  |     |     |     |     | 95  |     |

| Lys | Asp | Pro | Leu | Thr | Phe | Gly | Ala | Gly | Thr | Lys | Leu | Glu | Leu | Lys | Arg |
|     |     |     | 100 |     |     |     |     | 105 |     |     |     |     | 110 |     |     |

| Ala | Asp | Ala | Ala | Pro | Thr | Val | Ser |
|     |     | 115 |     |     |     |     | 120 |

( 2 ) INFORMATION FOR SEQ ID NO:27:

( i ) SEQUENCE CHARACTERISTICS:
        ( A ) LENGTH: 826 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 261..620

( x i ) SEQUENCE DESCRIPTION: SEQ ID NO:27:

AAGCTTATGA ATATGCAAAT CCTCTGAATC TACATGGTAA ATATAGGTTT GTCTATACCA    60

```
CAAACAGAAA AACATGAGAT CACAGTTCTC TCTACAGTTA CTGAGCACAC AGGACCTCAC        120

CATGGGATGG AGCTGTATCA TCCTCTTCTT GGTAGCAACA GCTACAGGTA AGGGGCTCAC        180

AGTAGCAGGC CTGAGGTCTG GACATATATA TGGGTGACAA TGACATCCAC TTTGCCTTTC        240

TCTCCACAGG TGTCCACTCC CAG GTC CAA CTG CAG GAG AGC GGT CCA GGC           290
                         Gln Val Gln Leu Gln Glu Ser Gly Pro Gly
                          1               5                  10

CTT GTG AGA CCT AGC CAG ACC CTG AGC CTG ACC TGC ACC GTG TCT GGC          338
Leu Val Arg Pro Ser Gln Thr Leu Ser Leu Thr Cys Thr Val Ser Gly
             15                  20                  25

TTC TCC ATC ACA AGT AGT AGT TAT TGC TGG CAC TGG GTG AGA CAG CCA          386
Phe Ser Ile Thr Ser Ser Ser Tyr Cys Trp His Trp Val Arg Gln Pro
             30                  35                  40

CCT GGA CGA GGT CTT GAG TGG ATT GGA CGC ATA TGT TAT GAA GGT TCA          434
Pro Gly Arg Gly Leu Glu Trp Ile Gly Arg Ile Cys Tyr Glu Gly Ser
         45                  50                  55

ATA GAC TAT AGT CCA TCC ATC AAA AGC AGA GTG ACA ATG CTG AGA GAC          482
Ile Asp Tyr Ser Pro Ser Ile Lys Ser Arg Val Thr Met Leu Arg Asp
         60                  65                  70

ACC AGC AAG AAC CAG TTC AGC CTG AGA CTC AGC AGC GTG ACA GCC GCC          530
Thr Ser Lys Asn Gln Phe Ser Leu Arg Leu Ser Ser Val Thr Ala Ala
 75                  80                  85                  90

GAC ACC GCG GTC TAT TAT TGT GCA AGA GAA AAC CAT GGT ACT ACG ACC          578
Asp Thr Ala Val Tyr Tyr Cys Ala Arg Glu Asn His Gly Thr Thr Thr
                 95                 100                 105

TCT ATG GAC TAC TGG GGC CAA GGG TCC TTG GTC ACC GTC TCC                  620
Ser Met Asp Tyr Trp Gly Gln Gly Ser Leu Val Thr Val Ser
             110                 115                 120

TCAGGTGAGT CCTTACAACC TCTCTCTTCT ATTCAGCTTA AATAGATTTT ACTGCATTTG        680

TTGGGGGGGA AATGTGTGTA TCTGAATTTC AGGTCATGAA GGACTAGGGA CACCTTGGGA        740

GTCAGAAAGG GTCATTGGGA GCCCGGGCTG ATGCTGACAG ACATCCTCAG CTCCCGGACT        800

TCATGGCCAG AGATTTATAG GGATCC                                             826
```

( 2 ) INFORMATION FOR SEQ ID NO:28:

( i ) SEQUENCE CHARACTERISTICS:
        ( A ) LENGTH: 120 amino acids
        ( B ) TYPE: amino acid
        ( D ) TOPOLOGY: linear ( i i ) MOLECULE TYPE: protein ( x i ) SEQUENCE DESCRIPTION: SEQ ID NO:28:

```
Gln Val Gln Leu Gln Glu Ser Gly Pro Gly Leu Val Arg Pro Ser Gln
 1               5                  10                  15

Thr Leu Ser Leu Thr Cys Thr Val Ser Gly Phe Ser Ile Thr Ser Ser
             20                  25                  30

Ser Tyr Cys Trp His Trp Val Arg Gln Pro Pro Gly Arg Gly Leu Glu
         35                  40                  45

Trp Ile Gly Arg Ile Cys Tyr Glu Gly Ser Ile Asp Tyr Ser Pro Ser
     50                  55                  60

Ile Lys Ser Arg Val Thr Met Leu Arg Asp Thr Ser Lys Asn Gln Phe
 65                  70                  75                  80

Ser Leu Arg Leu Ser Ser Val Thr Ala Ala Asp Thr Ala Val Tyr Tyr
             85                  90                  95

Cys Ala Arg Glu Asn His Gly Thr Thr Thr Ser Met Asp Tyr Trp Gly
         100                 105                 110

Gln Gly Ser Leu Val Thr Val Ser
     115                 120
```

(2) INFORMATION FOR SEQ ID NO:29:

(i) SEQUENCE CHARACTERISTICS:
        (A) LENGTH: 632 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 261..593

(xi) SEQUENCE DESCRIPTION: SEQ ID NO:29:

```
AAGCTTATGA ATATGCAAAT CCTCTGAATC TACATGGTAA ATATAGGTTT GTCTATACCA        60

CAAACAGAAA AACATGAGAC CACAGTTCTC TCTACAGTTA CTGAGCACAC AGGACCTCAC       120

CATGGGATGG AGCTGTATCA TCCTCTTCTT GGTAGCAACA GCTACAGGTA AGGGGCTCAC       180

AGTAGCAGGC TTGAGGTCTG ACATATATA  TGGGTGACAA TGACATCCAC TTTGCCTTTC       240

TCTCCACAGG TGTCCACTCC GAC ATC CAG ATG ACC CAG AGC CCA AGC AGC           290
                      Asp Ile Gln Met Thr Gln Ser Pro Ser Ser
                       1               5                  10

CTG AGC GCC AGC GTG GGT GAC AGA GTG ACC ATC ACC TGT AGA GCC AGT         338
Leu Ser Ala Ser Val Gly Asp Arg Val Thr Ile Thr Cys Arg Ala Ser
                 15              20                  25

GAA AGT GTT GAT AGT TAC GGC AAT AGT TTT ATG CAC TGG TAC CAG CAG         386
Glu Ser Val Asp Ser Tyr Gly Asn Ser Phe Met His Trp Tyr Gln Gln
             30                  35                  40

ACG CCA GGT AAG GCT CCA AAG CTG CTG ATC TAC GTT GCA TCC AAC CTA         434
Thr Pro Gly Lys Ala Pro Lys Leu Leu Ile Tyr Val Ala Ser Asn Leu
         45                  50                  55

GAA TCT GGT GTG CCA AGC AGA TTC AGC GGT AGC GGT AGC GGT ACC GAC         482
Glu Ser Gly Val Pro Ser Arg Phe Ser Gly Ser Gly Ser Gly Thr Asp
     60                  65                  70

TAC ACC TTC ACC ATC AGC AGC CTC CAG CCA GAG GAC ATC GCC ACC TAC         530
Tyr Thr Phe Thr Ile Ser Ser Leu Gln Pro Glu Asp Ile Ala Thr Tyr
 75                  80                  85                  90

TAC TGC CAG CAA AAT AAT GAA GAT CCG CTC ACG TTC GGC CAA GGG ACC         578
Tyr Cys Gln Gln Asn Asn Glu Asp Pro Leu Thr Phe Gly Gln Gly Thr
                 95                 100                 105

AAG CTG CAA ATC ACA CGTGAGTAGA ATTTAAACTT TGCTTCCTCA GTTGGATCC          632
Lys Leu Gln Ile Thr
             110
```

(2) INFORMATION FOR SEQ ID NO:30:

(i) SEQUENCE CHARACTERISTICS:
        (A) LENGTH: 111 amino acids
        (B) TYPE: amino acid
        (D) TOPOLOGY: linear (ii) MOLECULE TYPE: protein (xi) SEQUENCE DESCRIPTION: SEQ ID NO:30:

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Glu Ser Val Asp Ser Tyr
             20                  25                  30

Gly Asn Ser Phe Met His Trp Tyr Gln Gln Thr Pro Gly Lys Ala Pro
         35                  40                  45

Lys Leu Leu Ile Tyr Val Ala Ser Asn Leu Glu Ser Gly Val Pro Ser
     50                  55                  60

Arg Phe Ser Gly Ser Gly Ser Gly Thr Asp Tyr Thr Phe Thr Ile Ser
 65                  70                  75                  80
```

Ser Leu Gln Pro Glu Asp Ile Ala Thr Tyr Tyr Cys Gln Gln Asn Asn
                85                  90                      95

Glu Asp Pro Leu Thr Phe Gly Gln Gly Thr Lys Leu Gln Ile Thr
            100                 105                 110

(2) INFORMATION FOR SEQ ID NO:31:

(i) SEQUENCE CHARACTERISTICS:
        (A) LENGTH: 632 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 261..593

(xi) SEQUENCE DESCRIPTION: SEQ ID NO:31:

```
AAGCTTATGA ATATGCAAAT CCTCTGAATC TACATGGTAA ATATAGGTTT GTCTATACCA        60

CAAACAGAAA AACATGAGAC CACAGTTCTC TCTACAGTTA CTGAGCACAC AGGACCTCAC       120

CATGGGATGG AGCTGTATCA TCCTCTTCTT GGTAGCAACA GCTACAGGTA AGGGGCTCAC       180

AGTAGCAGGC TTGAGGTCTG GACATATATA TGGGTGACAA TGACATCCAC TTTGCCTTTC       240

TCTCCACAGG TGTCCACTCC GAC ATC CAG ATG ACC CAG AGC CCA AGC AGC           290
                        Asp Ile Gln Met Thr Gln Ser Pro Ser Ser
                         1           5                      10

CTG AGC GCC AGC GTG GGT GAC AGA GTG ACC ATC ACC TGT AGA GCC AGT         338
Leu Ser Ala Ser Val Gly Asp Arg Val Thr Ile Thr Cys Arg Ala Ser
                 15              20                  25

GAA AGT GTT GAT AGT TAC GGC AAT AGT TTT ATG CAC TGG TAC CAG CAG         386
Glu Ser Val Asp Ser Tyr Gly Asn Ser Phe Met His Trp Tyr Gln Gln
             30                  35                  40

ACG CCA GGT AAG GCT CCA AAG CTG CTG ATC TAC GTT GCA TCC AAC CTA         434
Thr Pro Gly Lys Ala Pro Lys Leu Leu Ile Tyr Val Ala Ser Asn Leu
         45                  50                  55

GAA TCT GGT GTG CCA AGC AGA TTC AGC GGT AGC GGT AGC GGT ACC GAC         482
Glu Ser Gly Val Pro Ser Arg Phe Ser Gly Ser Gly Ser Gly Thr Asp
 60                  65                  70

TTC ACC TTC ACC ATC AGC AGC CTC CAG CCA GAG GAC ATC GCC ACC TAC         530
Phe Thr Phe Thr Ile Ser Ser Leu Gln Pro Glu Asp Ile Ala Thr Tyr
 75                  80                  85                  90

TAC TGC CAG CAA AAT AAT GAA GAT CCG CTC ACG TTC GGC CAA GGG ACC         578
Tyr Cys Gln Gln Asn Asn Glu Asp Pro Leu Thr Phe Gly Gln Gly Thr
                 95                  100                 105

AAG CTG CAA ATC ACA CGTGAGTAGA ATTTAAACTT TGCTTCCTCA GTTGGATCC          632
Lys Leu Gln Ile Thr
             110
```

(2) INFORMATION FOR SEQ ID NO:32:

(i) SEQUENCE CHARACTERISTICS:
        (A) LENGTH: 111 amino acids
        (B) TYPE: amino acid
        (D) TOPOLOGY: linear (ii) MOLECULE TYPE: protein (xi) SEQUENCE DESCRIPTION: SEQ ID NO:32:

Asp Ile Gln Met Thr Gln Ser Pro Ser Ser Leu Ser Ala Ser Val Gly
 1               5                   10                  15

Asp Arg Val Thr Ile Thr Cys Arg Ala Ser Glu Ser Val Asp Ser Tyr
             20                  25                  30

Gly Asn Ser Phe Met His Trp Tyr Gln Gln Thr Pro Gly Lys Ala Pro

```
                              35                        40                          45
Lys  Leu  Leu  Ile  Tyr  Val  Ala  Ser  Asn  Leu  Glu  Ser  Gly  Val  Pro  Ser
          50                        55                        60

Arg  Phe  Ser  Gly  Ser  Gly  Ser  Gly  Thr  Asp  Phe  Thr  Phe  Thr  Ile  Ser
65                       70                        75                         80

Ser  Leu  Gln  Pro  Glu  Asp  Ile  Ala  Thr  Tyr  Tyr  Cys  Gln  Gln  Asn  Asn
                         85                        90                      95

Glu  Asp  Pro  Leu  Thr  Phe  Gly  Gln  Gly  Thr  Lys  Leu  Gln  Ile  Thr
               100                      105                      110
```

( 2 ) INFORMATION FOR SEQ ID NO:33:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:33:

```
CTGTCTCACC  CAGTGCCAGC  AATAACTACT  ACTTGTGATG  GAGAAGCCAG  ACAC                54
```

( 2 ) INFORMATION FOR SEQ ID NO:34:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:34:

```
CATTGTCACT  CTGCTTTTGA  TGGATGGACT  ATAGTCTATT  GAACCTTCAT  AACATATGCG          60

TCCMATCCAC  TCAAGA                                                              76
```

( 2 ) INFORMATION FOR SEQ ID NO:35:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:35:

```
CCAGTAGTCC  ATAGAGGTCG  TAGTACCATG  GTTTCTCTT   GMACAATAAT  AGAC                54
```

( 2 ) INFORMATION FOR SEQ ID NO:36:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:36:

```
ATGGTGAAGG  TGTAGTCGGT  ACCGC                                                   25
```

( 2 ) INFORMATION FOR SEQ ID NO:37:

( i ) SEQUENCE CHARACTERISTICS:
        ( A ) LENGTH: 26 base pairs
        ( B ) TYPE: nucleic acid
        ( C ) STRANDEDNESS: single (D) TOPOLOGY: linear (ii) MOLECULE TYPE: DNA (xi) SEQUENCE DESCRIPTION: SEQ ID NO:37:

AGGTTGGATG CAACGTAGAT CAGCAG　　　　　　　　　　　　　　　　　　　　　26

(2) INFORMATION FOR SEQ ID NO:38:

(i) SEQUENCE CHARACTERISTICS:
(A) LENGTH: 38 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:38:

CCGAACGTGA GCGGATCTTC ATTATTTGC TGGCAGTA　　　　　　　　　　　　　　38